United States Patent
Kitajewski et al.

(10) Patent No.: US 6,379,925 B1
(45) Date of Patent: Apr. 30, 2002

(54) ANGIOGENIC MODULATION BY NOTCH SIGNAL TRANSDUCTION

(75) Inventors: Jan Kitajewski, Ridgewood, NJ (US); Hendrik Uyttendaele, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/467,997

(22) Filed: Dec. 20, 1999

Related U.S. Application Data

(63) Continuation of application No. PCT/US98/13050, filed on Jun. 18, 1998, which is a continuation-in-part of application No. 08/878,351, filed on Jun. 18, 1997, now abandoned.

(51) Int. Cl.[7] .................. C12P 21/02; C07H 21/04; C12N 1/00; C12N 1/19; C12N 1/21
(52) U.S. Cl. .................. 435/69.1; 435/243; 435/252.3; 435/254.2; 435/320.1; 435/325; 435/410; 536/23.5
(58) Field of Search .................. 536/23.5; 435/320.1, 435/325, 243, 410, 252.3, 254.2, 69.1

(56) References Cited

PUBLICATIONS

Bettenhausen, B., et al. (1995) "Transient and restricted expression during mouse embryogenesis of Dll, a murine gene closely related to Drosophila Delta," Development121: 2407–2418.
Coffman, C. R., et al. (1993) "Expression of an extracellular deletion of Xotchdiverts cell fate in xenopus embryos," Cell, 73: 659–671.
Fortini, M.E., et al. (1993) "An activated notch receptor blocks cell–fate commitment in the developing drosophila eye," Nature 365: 555–557.
Fortini, M. E. and Artavanis–Tsakonas, S., (1994) "The suppressor of hairless protein participates in notch receptor signaling," Cel 79: 273–282.
Gallahan, D. and Callahan, R., (1987) "Mammary tumorigenesis in feral mice: identification of a new int locus in mouse mammary tumor virus (Czech II)–induced mammary tumors," J. Virol., 61: 66–74.
Jarriault, S., et al. (1995) "Signaling downstream of activated mammalian notch," Nature 377:355–358.
Jhappan, C., Gallahan, D., Stahle, C., Chu, E., Smith, G. H., Merlino, G. and Callahan, R. (1992). "Expression of an activated notch–related int –3 transgene interferes with cell differentiation and induces neoplastic transformation in mammary and salivary glands".
Genes Devel 6:345–355.
Kopan, R., Nye, J. S. and Weintraub, H. (1994) "The intracellular domain of mouse notch: a constitutively activated repressor of myogenesis directed at the basic helix––loop–helix region of MyoD". Development120: 2385–2396.

Lindsell, C. E., Shawber, C. J., Boulter, J. and Weinmaster, G. (1995). "Jagged: a mammalian ligand that activates notch1". Cell80:4 909–917.
Robbins, J., Blondel, B. J., Gallahan, D. and Callahan, R. (1992). "Mouse mammary tumor gene int–3, a member of the notch gene family transforms mammary epithelial cells"J. Virol 66: 2594–2599.
Roux, F., Durieu–Trautmann, O., Chaverot, N., Claire, M., Mailly, P., Bourre, J. M., Strosberg, A. D., and Couraud P. O. (1994) "Regulation of gamma–glutamyl transpeptidase and alkaline phosphatase activities in immortalized rat brain microvessel endothelial cells"J. Cell Physiol.159: 101–113.
Sarkar, N. H., Haga, S., Lehner, A. F., Zhao, W., Imai, S. and Moriwaki, K. (1994).
"Insertional mutation of int protooncogenes in the mammary tumors of a new strain of mice from the wild in China: normal– and tumor–tissue–specific expression of int –3 transcripts". Virology 203: 52–62.
Smith, G. H., et al. (1995) "Constitutive expression of a truncated INT–3 gene in mouse mammary epithelium impairs differentiation and functional development". Cell Growth& Differentiation6: 563–577.
Struhl, G., et al. (1993). "Intrinsic activity of the Lin–12 and Notch intracellular domains in vivo ". Cel l74: 331–345.
Sugaya et al. (1994) "Three Genes in the Human MHC Class III Region near the Junction with the Class II: Gene for Receptor of Advanced Glycosylation End Products, PBX2 Home box Gene and a Notch Homolog, Human Counterpart of Mouse Mammary Tumor Gene int–3" Genomics 23(2); 408–419. (Exhibit 1).
Sugaya et al. (1997) "Gene Organization of Human NOTCH4 and (CTG)n Polymorphism in this Human Counterpart Gene of Mouse Proto–oncogene Int3" Gene189(2): 235–244. (Exhibit 2).
Uyttendaele et al. (1996) "Notch4/int–3, a Mammary protooncogene, is an Endothelial Cell–Specific Mammalian Notch Gene" Development 122(7):2251–2259. (Exhibit 3).
Weinmaster, G., et al., (1991) "A homolog of drosphila notch expressed during mammalian development". Development113: 199–205.

(List continued on next page.)

Primary Examiner—Terry McKelvey
(74) Attorney, Agent, or Firm—John P. White; Cooper & Dunham LLP

(57) ABSTRACT

This invention provides methods of modulating angiogenesis, including promoting or inhibiting angiogenesis, e.g., in connection with treating abnormalities including hemangiomas, hemangiosarcomas, Kaposi's Sarcoma, ischemic disorders, and wounds. These methods involve administration of compounds that are selective agonists or antagonists of Notch4 protein. In addition, this invention provides an isolated nucleic acid molecule encoding a Notch4, an isolated Notch4 protein, vectors comprising an isolated nucleic acid molecule encoding a Notch4 protein, cells comprising such vectors, antibodies directed to Notch4 protein, nucleic acid probes useful for detecting nucleic acids encoding Notch4 protein, and antisense oligonucleotides complementary to any unique sequences of a nucleic acid molecule which encodes Notch4 protein.

19 Claims, 26 Drawing Sheets

OTHER PUBLICATIONS

Weinmaster, G., et al. (1992) "Notch 2: a second mammalian Noth gene", *Development* 116: 931–941.

Williams, R., et al., (1995) "Complementary and combinatorial patterns of Notch gene Family expression during early mouse development", *Mechanisms of Development*, 53: 357–368.

Zimrin, A. B., Pepper, M. S., McMahon, G. A., Nguyen, F., Montesano, R., and Maciag, T. (1996) "An antisense oligonucleotide to the notch ligand jagged enhances fibroblast growth factor–induced agiogenesis in vitro ". *J. Biol. Chem.*, No. 51 271: 32499–32502.

FIGURE 1A

```
  1  MQPQLLLLLLPLNFPVILTRELL|CGGSPEPCANGGTCLRLSRGQGICQCAPGFLGETCQFPDPCRDTQLCKNGGSCQAL
                            1                    2                            4
                                       3
 81  LPTPPSSRSPTSPLTPHFSCTCPSGFTGDRCQTHLEELCPPSFCSNGGHCYVQASGRPQCSCEPGWTGEQCQLRDFCSAN
                                                                              6
                            5
161  PCANGGVCLATYPQIQCRCPPGFEGHTCERDINECFLEPGPCPQGTSCHNTLGSYQCLCPVGQEGPQCKLRKGACPPGSC
                                                                               8
                            7
241  LNGGTCQLVPEGHSTFHLCLCPPGFTGLDCEMNPDDCVRHQCQNGATCLDGLDTYTCPCPKTWKGWDCSEDIDECEARGP
                                                                              10
                            9
321  PRCRNGGTCQNTAGSFHCVCVSGWGGAGCEENLDDCAAATCAPGSTCIDRVGSFSCLCPPGRTGLLCHLEDMCLSQPCHV
                                                                              12
                           11
401  NAQCSTNPLTGSTLCICQPGYSGSTCHQDLDECQMAQQGPSPCEHGGSCINTPGSFNCLCLPGYTGSRCEADHNECLSQP
                                                                              14
                           13
481  CHPGSTCLDLLATFHCLCPPGLEGRLCEVEVNECTSNPCLNQAACHDLLNGFQCLCLPGFTGARCEKDMDECSSTPCANG
                                                                              16
                           15
561  GRCRDQPGAFYCECLPGFEGPHCEKEVDECLSDPCPVGASCLDLPGAFFCLCRPGFTGQLCEVPLCTPNMCQPGQQCQGQ
                                          17                                  18
641  EHRAPCLCPDGSPGCVPAEDNCPCHHGHCQRSLCVCDEGWTGPECETELGGCISTPCAHGGTCHPQPSGYNCTCPAGYMG
                                                                              20
                           19
721  LTCSEEVTACHSGPCLNGGSCSIRPEGYSCTCLPSHTGRHCQTAVDHCVSASCLNGGTCVNKPGTFFCLCATGFQGLHCE
                                          21                                  22
801  EKTNPSCADSPCRNKATCQDTPRGARCLCSPGYTGSSCQTLIDLCARKPCPHTARCLQSGPSFQCLCLQGWTGALCDFPL
     23                                                    24
881  SCQKAAMSQGIEISGLCQNGGLCIDTGSSYFCRCPPGFQGKLCQDNVNPCEPNPCHHGSTCVPQPSGYVCQCAPGYEGQN
                                          25                                  26
961  CSKVLDACQSQPCHNHGTCTSRPGGFHCACPPGFVGLRCEGDVDECLDRPCHPSGTAACHSLANAFYCQCLPGHTGQRCE
```

EGF-like repeats

FIG. 3

```
              ↓  ↓↓                              ↓         ↓
Notch 1   QDVDE CDL...GANR CEHAGKCLNTLGSFECQCLQGYTGPGCE
                  *
Notch 2   EDVDE CAMAN..SNP CEHAGKCVNTDGAFHCECLKGYAGPRCE Notch 3   QDVDE CSI...GANP CEHLGRCVNTQGSFLCQCGRGYTGPRCE Notch 4   QDLDE CQMAQQGPSP CEHGGSCINTPGSFNCLCLPGYTGSRCE
          └─────────────────────────────────────────────┘
                         EGF-like repeat #11
```

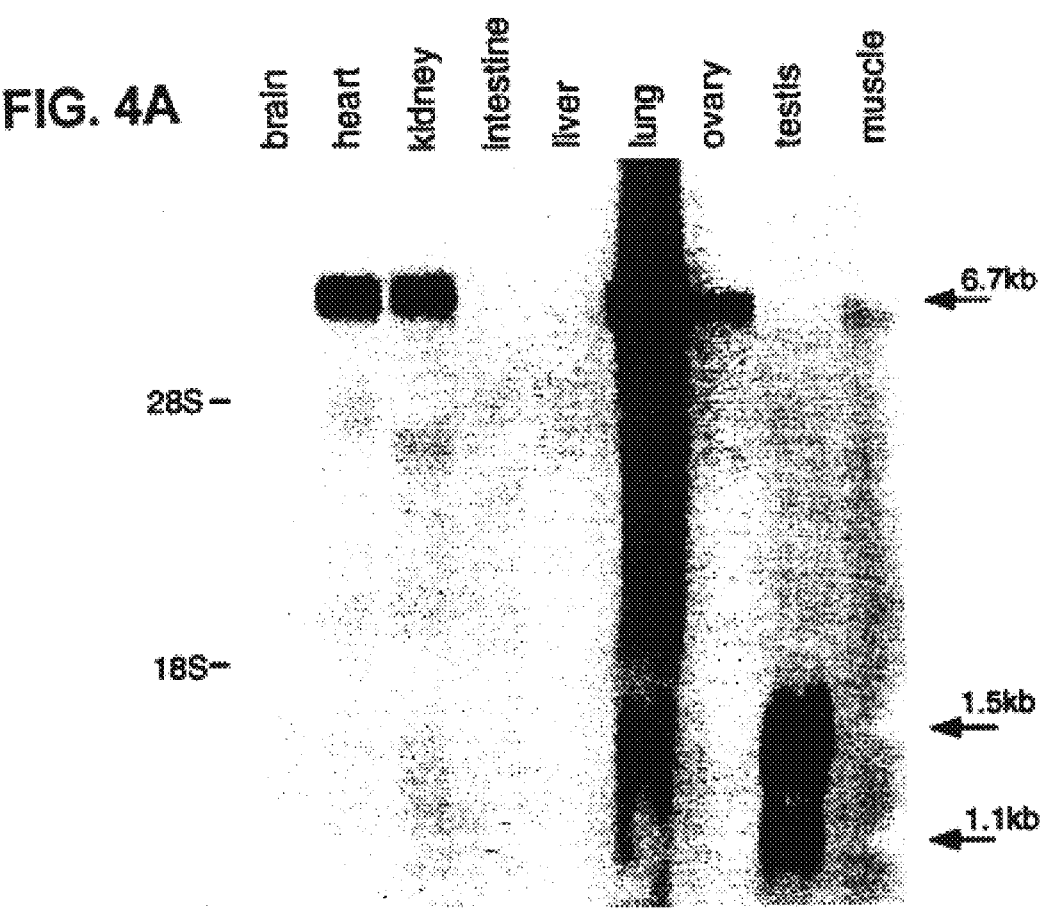
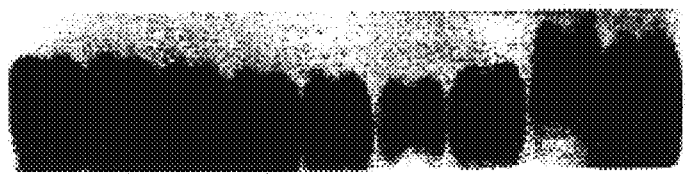

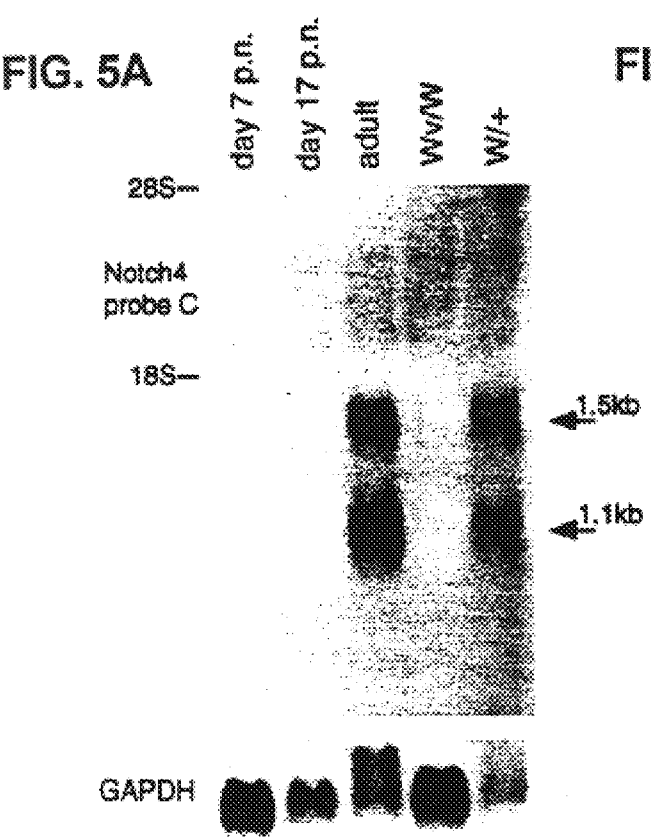

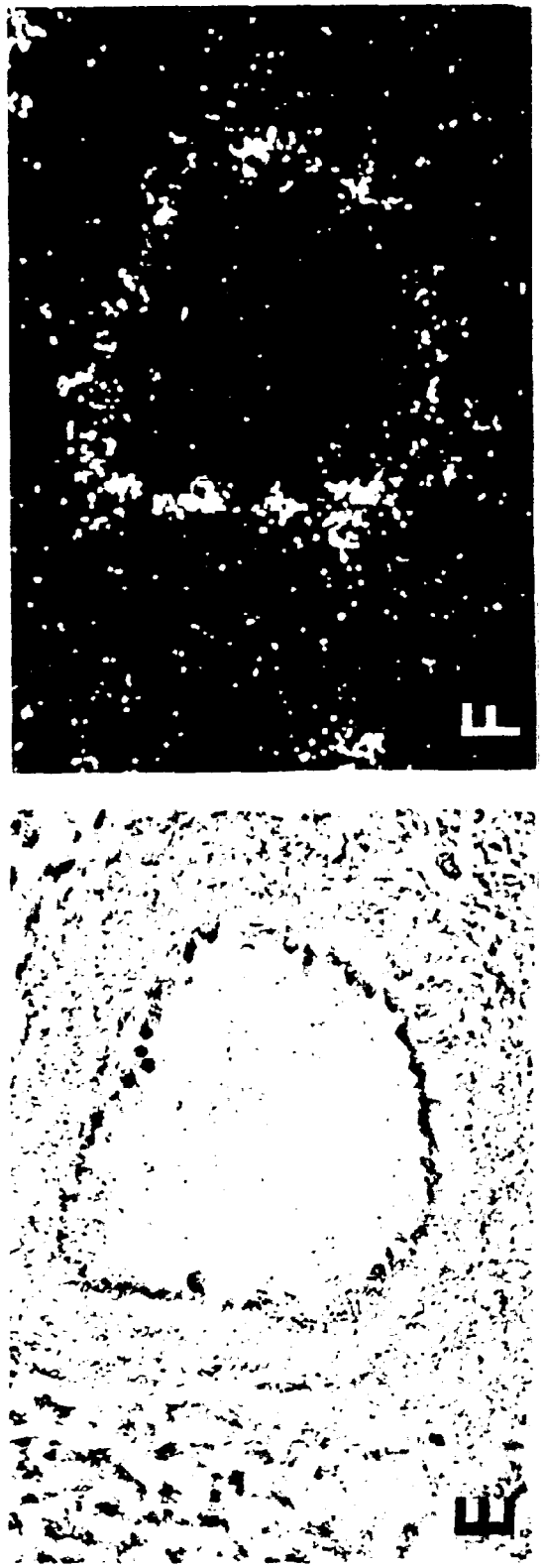

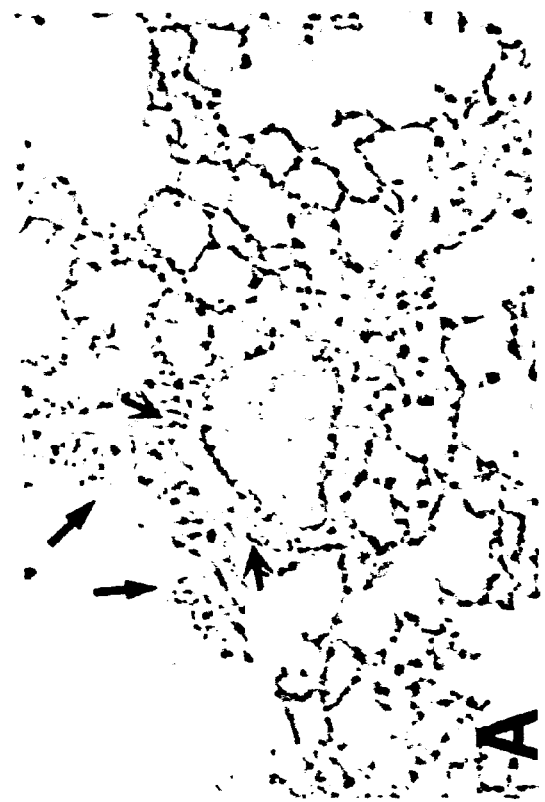

FIG. 8A FIG. 8B
FIG. 8C FIG. 8D
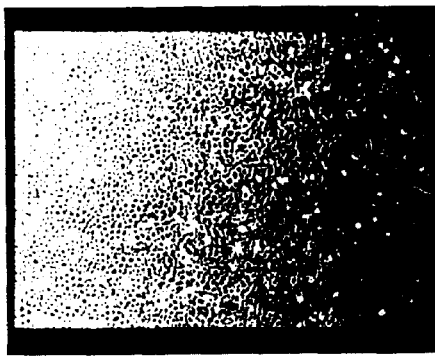 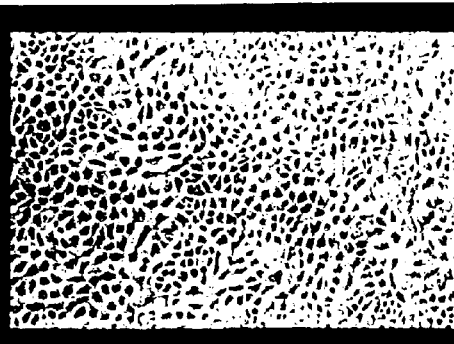

FIG. 8M FIG. 8N
FIG. 8O FIG. 8P
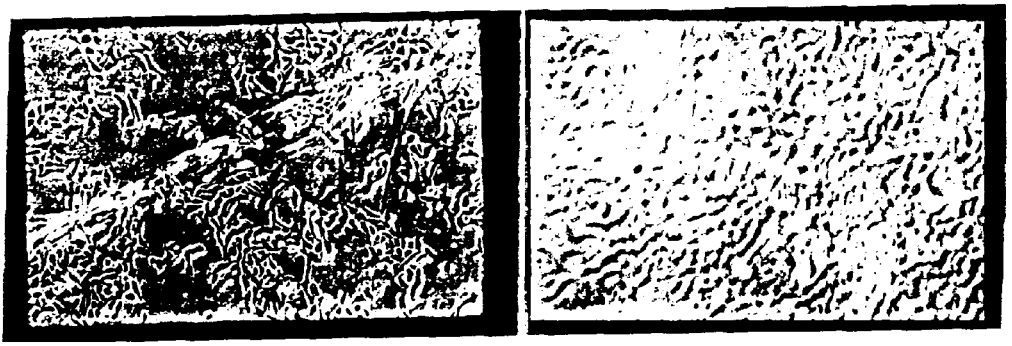

FIG. 8Q FIG. 8R
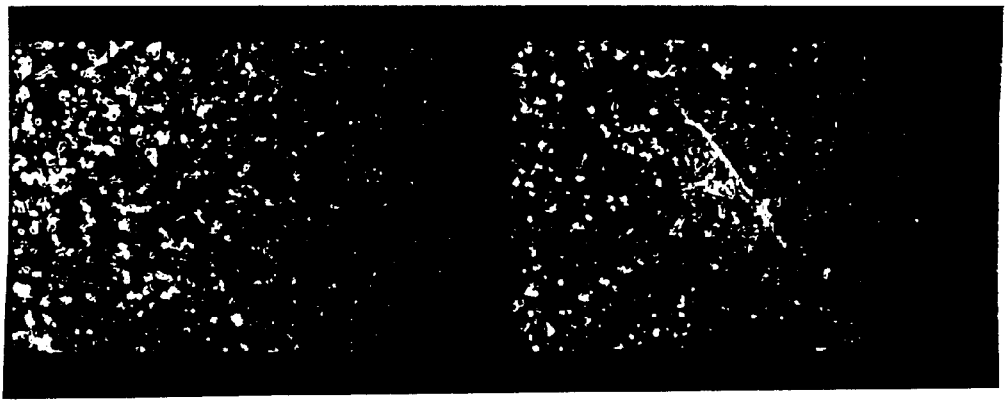
FIG. 8S FIG. 8T
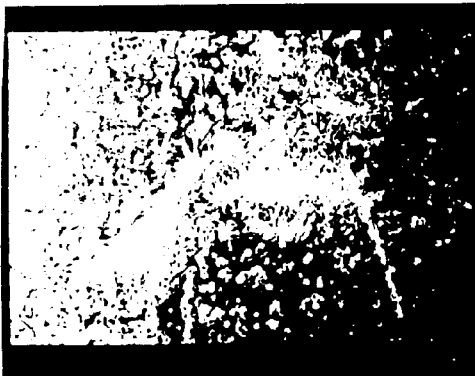 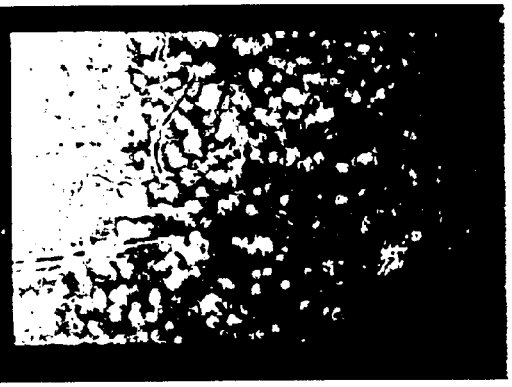

FIGURE 9A

```
   1 GGGAAAACAG GTGTGTTTCT GCCTTTTACT TCTAACTTGG AATACCTTAC CCAATCCCAG
  61 TTCTTCATCT CCTCTGAGAA GTTATAGGGT TAAAAATATT GTCTTCTTAC ATCAGCAGAT
 121 ATATGACAAG GGAAGAGATC CTTTGGTCAG CTCTAGTAAT CTGGCTTTGT CCCCCTTAGG
 181 GAATAGACTT TGGCCTGAGG GAACAGCTCA GACTGAGGCG TGCAGCAGGC TCAGGAGGAA
 241 GAAGGGCGGT AGAAGCAGAG GAAGTGGCCT TGCCTGGCCA CAAGGGCTCT GAGGGTCCCT
 301 GCCTGAAGAG GGAGAGGAGA TCCGGGCCAG GGGCAGGTGC TCTGGAATGC AGCCCCAGTT
 361 GCTGCTGCTG CTGCTCTTGC CACTCAATTT CCCTGTCATC CTGACCAGAG AGCTTCTGTG
 421 TGGAGGATCC CCAGAGCCCT GTGCCAACGG AGCCACCTGC CTGAGGCTAT CTCGGGACA
 481 AGGGATCTGC CAGTGTGCCC CTGGATTTCT GGGTGAGACT TGCCAGTTTC CTGACCCCTG
 541 CAGGGATACC CAACTCTGCA AGAATGGTGG CAGCTGCCAA GCCCTGCTCC CCACACCCCC
 601 AAGCTCCCGT AGTCCTACTT CTCCACTGAC CCCTCACTTC TCCTGCACCT GCCCCTCTGG
 661 CTTCACCGGT GATCGATGCC AAACCCATCT GAAGAGCTC TGTCCACCTT CTTTCTGTTC
 721 CAACGGGGT CACTGCTATG TTCAGGCCTC AGCCGCCCA CAGTGCTCCT GCGAGCCTGG
 781 GTGGACAGGT GAGCAATGCC AGCTCCGAGA CTTCTGCTCA GCCAACCCCT GTGCCAACGG
 841 AGGCGTGTGC CTGGCCACAT ACCCCCAGAT TCAACGAGTG CCAGTGCCGC TGTCCACCTG GGTTCGAGGG
 901 TCACACCTGT GAACGCGACA TCAACGAGTG CTTCCTGGAG CCGGACCCT GCCCTCAGGG
 961 CACCTCCTGC CATAACACCT TGGGTTCCTA CCAGTGTCTC TGCCCTGTGG GGCAGGAAGG
1021 TCCCCAGTGC AAGCTCAGGA AGGGAGCCTG CCCTCCTGGA AGCTGTCTCA ATGGGGCAC
```

FIGURE 9B

```
1081 CTGCCAGCTG GTCCCAGAGG GACACTCCAC CTTTCATCTC TGCCTCTGTC CCCAGTTT
1141 CACGGGGCTG GACTGTGAGA TGAACCCAGA TGACTGTGTC AGGCACCAGT GTCAGAACGG
1201 GGCCACCTGT CTGGATGGGC TGGATACCTA CACCTGCCCC TGCCCCAAGA CATGGAAGGG
1261 CTGGGACTGC TCTGAAGATA TAGATGAATG TGAAGCCCGG GGTCCCCCTC GCTGCAGGAA
1321 CGGTGGCACC TGCCAGAACA CAGCTGGCAG CTTTCACTGT GTGTGCCTGA GTGGCTGGGG
1381 AGGTGCAGGC TGTGAGGAGA ACCTGGATGA CTGTGCAGCT GCCACCTGTG CCCGGGATC
1441 CACCTGCATC GACCGTGTGG GCTCTTTCTC CTGCCTCTGC CCACCTGGAC GCACAGGCCT
1501 CCTGTGCCAC CTGGAAGACA TGTGTTTGAG TCAGCCGTGC CACGTGAATG CCCAGTGCAG
1561 CACCAACCCT CTGACAGGCT CCACCCTCTG CATATGCCAG CCTGGCTACT CAGGATCCAC
1621 CTGTCACCAA GATCTGGATG AGTGCCAAAT GGCCCAGCAA GGACCCAGTC CCTGCCAACA
1681 TGGGGGTCC TGCATCAACA CCCCTGGCTC CTTCAACTGC CTCTGCCTGC CTGGTTACAC
1741 GGGCTCCCGC TGTGAAGCTG ACCACAATGA GTGCCTGTCA CAGCCCTGCC ACCCAGGCAG
1801 CACCTGCCTG GACCTGCTTG CAACCTTCCA CTGCCTCTGC CCACCAGGCT TGGAAGGGAG
1861 ACTCTGTGAG GTGGAGTCA ATGAGTGCAC CTCTAATCCC TGCCTGAACC AAGCTGCCTG
1921 CCATGACCTG CTCAACGGCT TCCAGTGCCT CTGCCTTCCT GGATTCACCG GCGCCCGATG
1981 TGAGAAAGAC ATGGACAGAGT GTAGCAGCAC CCCCTGTGCC AATGGGGGC GCTGCCAGA
2041 CCAGCCTGA GCCTTCTACT GCGAGTGTCT CCCAGGCTTT GAAGGCCCAC ACTGTGAGAA
2101 AGAAGTGGAC GAATGTCTGA GTGACCCCTG TCCCGTGGGA GCCAGCTGTC TTGATCTCCC
2161 CGGAGCATTC TTCTGTCTCT GCCCTGGCTG TTTCACAGGT CAACTTTGTG AGGTTCCCTT
2221 GTGCACCCCC AACATGTGCC AACCTGGACA GCAATGCCAA GTCAGGAAC ACAGAGCCCC
2281 CTGCCTCTGC CCTGACGGAA GTCCTGGCTG TGTTCCTGCC GAGACAACT GCCCCTGTCA
2341 CCATGGCCAT TGCCAGAGAT CTGGGTGGCT CCTTGTGTGT GTGTGATGAG GGCTGGACTG GACCAGAATG
2401 CGAGACAGAA CTGGGTGGCT GCATCTCCAC ACCCTGTCC CATGGGGGGA CCTGCCACCC
2461 ACAGCCATCT GGCTACAACT GTACCTGCCC TGCAGGCTAC ATGGGGTTGA CCTGTAGTGA
2521 GGAGTGACA GCTTGTCACT CAGGGCCCTG TCTCAATGGT GGCTCCTGCA GCATCCGTCC
2581 TGAGGGCTAT TCCTGCACCT GCCTTCCAAG TCACACAGGT CGCCACTGCC AGACTGCCGT
2641 GGACCACTGT GTGTCTGCCT CGTGCCTCAA TGGGGTACC TGTGTGAACA AGCCTGCAC
2701 TTTCTTCTGC CTCTGTGCCA CTGGCTTCCA GGGGCTGCAC TGTGAGGAGA AGACTAACCC
2761 CAGCTGTGCA GACAGCCCCT GCAGGAACAA GGCAACCTGC CAAGACACAC CTCGAGGGGC
2821 CCGCTGCCTC TGCAGCCCTG GCTATACAGG AAGCAGCTGC CAGACTCTGA TAGACTGTGT
2881 TGCCCGGAAG CCCTGTCCAC ACACTGCTCG ATGCCTCCAG AGTGGCCCT CGTTCCAGTG
```

FIGURE 9C

```
2941 CCTGTGCCTC CAGGGATGGA CAGGGGCTCT CTGTGACTTC CCACTGTCCT GCCAGAAGGC
3001 CGCGATGAGC CAAGGCATAG AGATCTCTGG CCTGTGCCAG AATGGAGGCC TCTGTATTGA
3061 CACGGGCTCC TCCTATTTCT GCCGCTGCCC TCCTGGATTC CAAGGCAAGT TATGCCAGGA
3121 TAATGTGAAC CCCTGCGAGC CCAATCCCTG CCATCACGGG TCTACCTGTG TGCCTCAGCC
3181 CAGTGGCTAT GTCTGCCAGT GTGCCCCAGG CTATGAGGGA CAGAACTGCT CAAAAGTACT
3241 TGACGCTTGT CAGTCCCAGC CCTGCCACAA CCACGAACC TGTACCTCCA GGCCTGGAGG
3301 CTTCCACTGT GCCTGCCCTC CAGGCTTCGT GGGACTGCGC TGTGAGGGAG ATGTGGATGA
3361 GTGTCTGGAC CGGCCCCTGT ACCCCTCGGG CACTGCAGCT TGCCACTCTT TAGCCAACGC
3421 CTTCTACTGC CAGTGTCTGC CTGGCACAC AGGCCAGCGG TGTGAGGTGG AGATGGACCT
3481 CTGTCAGAGC CAACCCTGCT CCAATGGAGG ATCCTGTGAG ATCACAACAG GGCCACCCCG
3541 TGGCTTCACC TGTCACTGCC CCAAGGGTTT TGAAGGCCCC ACCTGCAGCC ACAAAGCCCT
3601 TTCCTGCGGC ATCCATCACT GCCACAATGG AGGCCTATGT CTGCCCTCCC CTAAGCCAGG
3661 GTCACCACCG CTCTGTGCCT GCCTCAGTGG TTTTGGGGGC CCTGACTGTC TGACACCTCC
3721 AGCTCCACCG GGCTGCGGTC CCCCCTCACC CTGCCTGCAC AATGGTACCT GCACTGAGAC
3781 CCCTGGGTTG GGCAACCCGG GCTTTCAATG CACCTGCCCT CCTGACTCTC CAGGGCCCCG
3841 GTGTCAAAGG CCAGGGGCAA GTGGGTGTGA GGGCCAGAGT GGTGATGGGA CCTGCGATGC
3901 TGGCTGCAGT GGCCCAGGAG GAGACTGGGA TGGAGGGGAC TGTTCCCTGG GGTCCCCAGA
3961 CCCCTGGAAG GGCTGTCCCC CGCATTCCCA GTGCTGGCTT CTGTTCCGGG ACGGACGGTG
4021 TCACCCGCAG TGTGACTCTG AGGAGTGTCT CTTTGATGGC TACGACTGTG AAATCCCTCC
4081 AACCTGCATC CCAGCCTATG ACCAGTACTG TTCCACAACG GGCACTGTGA
4141 GAAAGGCTGC AATAACGCTG AATGGGCTG GGACGGGGA GACTGCAGAC CAGAAGGGGA
4201 AGACTCAGAG GGGAGGCCCT CCCTGGCCCT GCTGGTGGTG CTGAGCCCCC CAGCCCTGGA
4261 TCAGCAGCTG CTTGCCCTGG CACGAGTGCT GTCCCTGACT CTGAGGGTCG GTCTCTGGGT
4321 GAGGAAGGAC AGTGAAGGCA GGAACATGGT GTTCCCCTAT CCTGGGACCC GGGCCAAAGA
4381 GGAGCTGAGT GGACTAGGG ATTCCTCTTC ATGGAAAGA CAAGCCCCTC CCACTCAGCC
4441 CCTGGGCAAG GAGACAGAGT CTCTTGGTGC AGGGTTTGTG GTAGTGATGG GAGTGGATCT
4501 GTCCCGCTGT GGTCCGGAAC ATCCTGCGTC CCGCTGCCCC TGGACTCTG GACTCCTGCT
4561 GCGCTTCCTT GCAGCAATGG CAGCAGTGGG AGCTCTGGAG GCCCCCTGC CCCCTGCCCTG CTTGACCCTT
4621 GCTGGCGGCT CACCCCTCAAG CAGGGACCAG GCCCCCTGCC AACCAGCTTC CCTGGCCAT
4681 TCTATGTTCA CCAGTGGTTG GGGTGCTTCT CCTGCCCCTT GGGCCCCTC TCGTCCTCCA
```

FIGURE 9D

```
4741  GCTCATTCGG CGACGGCGAC GAGAACATGG GGCCCTGTGG CTGCCCCCTG GTTTCATTCG
4801  AAGGCCTCAG ACACAGCAGG CACCCCACCG GCGGAGGCCC CCACTGGGCG AGGACAACAT
4861  TGGTCTTAAG GCACTGAAGC CAGAGCCCGA AGTGGATGAG GATGGAGTGG CCATGTGCTC
4921  GGGCCCTGAA GAGGGAGAGG CTGAAGAAAC AGCCTCAGCC TCCAGGTGCC AGCTTTGGCC
4981  GCTCAACAGC GGCTGTGGAG AGCTCCCCCA GGCAGCCATG CTGACCCCTC CTCAGGAGTG
5041  TGAATCGGAG GTTCTGGATG TGGACACCTG TGGACCTGAT GGGGTGACAC CCCTGATGTC
5101  AGCCGTCTTC TGTGGGGGAG TGCAGTCCAC GACTGGGGCT AGTCCACAGA GACTGGGGCT
5161  AGGAAATCTG GAACCCTGGG AACCACTGCT GGATAGAGGG GCCTGCCCCC AGGCTCACAC
5221  TGTGGGCACT GGAGAGACGC CTCTGCACCT AGCTGCCAGA TTCTCTCGGC CAACCGCTGC
5281  CCGCCGCCTC CTTGAGGCTG GAGCCAACCC CAACCAGCCA GACCGCGCTG GGGCACCCCC
5341  ACTTCACACT GCTGTGGCTG CCGACGCTCG GGAGGTTTGC CAGCTCCTAT TGGCCAGCAG
5401  ACAGACTACG GTGGACGCCC GCACAGAGA  CGGGACTACA CCTTTGATGC TGGCTGCCAG
5461  GCTGGCCGTG GAGGACCTGG TTGAAGAATT GATCGCAGCC CGAGCAGATG TAGGAGCCAG
5521  GGATAAAAGG GGAAAAACTG CACTGCACTG GCCCGCTGCT GTGAACAACG CCCGAGCCGC
5581  CCGCTCTCTC CTCCAGGCTG GAGCGGATAA AGATGCCCAG GACAGTAGGG AACAGACGCC
5641  GCTTTTCCTG GCAGCGCGCG AAGGAGCCGT GGAGGTGGGG CAGCTGTTGC TGGAGCTCGG
5701  GCCGGCCCGG GGACTGCGAG ACCAGCCCGG GCTGGCCCCA GGAGATGTGG CCCGCCAGCG
5761  CAGTCACTGG GACCTGCTAA CGCTGCTGGA AGGGGCTGGA CCGACTACGC AGGAGGCCCG
5821  TGCGCACGCA CGCACCACGC CGGGGGGCGG GTCCGCCCCG CGCTGCCGGA CGCTGTCTGC
5881  GGGAGCGCGC CCGCGCGGGG GCGAGGAAGG TCTGCAGGCT CGCACTTGGT CGGTGGACTT
5941  GGGAGCCGCG CGGGCCCGCA GGTTCTCCGC CTGCCGGAGC CGATCTGAA  GCTGCGGAGG
6001  CCCCACCACG ATCACAGGAT GACTGGCCTC GCGACTGGGT GGGCTCCCGT GAACGACGCG GGGCTAGGGC
6061  TGCGCCGATC CCGCCTCCCA GCCTGACCCC GTCCCAGAA  GCCTGCGGCT CCGCCTGCAG
6121  CTGGGTCTT  CCAGTTCACC AAGAGATTCC CTTAAACTCG CGTGGATCCC CTCAAGTTGC
6181  GGCAGCTGCG TGGAAGGAAG GAAGCGACAC GTACGAGTCT GGAAGACTCC GACTTTTAA
6241  GGCCAAAATA ACCGTTAAGC TCACTTGTCT CCCCATAGA  GTATGCACAG CAATGGGAAG
6301  AGGGTTTAGG ATGTCCGGTT GAGATAGAGC GTGATTTTCC TGGAAAATAG GGCAGCTTCA
6361  AGAGGACAAA GTTGATTTCG AGAATCCCTA AACTCTGGAA CCAAGAACTG TGGGCGAATT
6421  GGGTGTAAAA TGTTTCTTGT GTATGGTTTC CCAAAAGGAG CCTCTGCTAT CTACTGCCCA
6481  CAAGTAGCTG GCAACTATTT ATTAAGCACC TACGATGTGC CGGGTGTTGT GTAGATGAAC
6541  AGTAAGTAAC CAGTGGCCCA TCCAGCTGAT GACTCCTTGC CCTCTCTCTG CCTCCCCACA
6601  AGGACACTGG TGCAGGG
```

ANGIOGENIC MODULATION BY NOTCH SIGNAL TRANSDUCTION

This application is a continuation of PCT International Application No. PCT/US98/13050, filed Jun. 18, 1998, designating the United States of America, which is CIP of U.S. Ser. No. 08/878,351, filed Jun. 18, 1997, now abandoned the contents of which are hereby incorporated by reference into the present application.

The invention disclosed herein was made with Government support under Grant Nos. DAMD17-94-J-4410, DAMD17-94-J-4153 and DAMD17-97-1-7291 from the Department of Defense. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

The int-3 gene was originally identified based on its oncogenic effects in the mouse mammary gland. int-3 is a frequent target for insertional activation by MMTV proviral DNA in MMTV-induced mammary gland tumors (Gallahan and Callahan, 1987; Robbins et al., 1992; Sarkar et al., 1994). Tumor specific transcripts derived from the int-3 gene encode a protein homologous to the intracellular part of the Notch family of cell surface receptors. Exogenous expression of the int-3 oncoprotein has been shown to affect the growth and development of mammary epithelial cells. Over expression of the int-3 oncoprotein in a mouse mammary epithelial cells (HC11) promotes anchorage independent growth (Robbins et al., 1992). Expression of int-3 as an MMTV-LTR driven transgene in the mouse mammary gland results in abnormal development of the mammary gland and rapid development of undifferentiated mammary carcinomas (Jhappan et al., 1992). In the normal mouse mammary gland, endogenous int-3 protein has been detected in mammary stroma and epithelium (Smith et al., 1995).

Members of the Notch/lin-12 gene family were first identified in Drosophila and *Caenorhabditis elegans* through genetic analysis of mutations that alter cell fate decisions (for review see Artavanis-Tsakonas et al., 1995; Artavanis-Tsakonas and Simpson, 1991; Greenwald and Rubin, 1992). Drosophila Notch regulates multiple cell fate decisions that involve cell-cell interactions during fly development, for instance, control of cell fate decisions involving neural/epidermal specification in proneural clusters (Artavanis-Tsakonas and Simpson, 1991). The *C. elegans* lin-12 and glp-1 proteins are structurally related to Notch, and are also involved in cell fate specifications during development in the nematode (Greenwald, 1985; Yochem and Greenwald, 1989). Genetic analysis of Notch/lin-12 genes suggest that this family of genes controls binary cell fate decisions and inductive signaling that depend on cell-cell interactions (reviewed in Artavanis-Tsakonas et al., 1995; Greenwald, 1994; Greenwald and Rubin, 1992). Alternatively, Notch/lin-12 genes have been proposed to block cell differentiation, thus maintaining the competence of cells for subsequent cell-fate determination (Coffman et al., 1993; Fortini et al., 1993).

Notch/lin-12 genes encode transmembrane receptor proteins characterized by highly repeated, conserved domains. The amino terminus of Notch proteins encodes the extracellular domain and contains as many as 36 repeats of an EGF-like motif involved in ligand binding (Rebay et al., 1993), and three tandem copies of a Notch/lin-12 sequence motif of unknown function. The intracellular portion of Notch proteins is characterized by six tandem copies of a cdc10/ankyrin motif, thought to be a protein-protein interaction domain (Michaely and Bennett, 1992), and a PEST sequence motif which may represent a protein degradation signal (Rogers et al., 1986). In several systems, truncated forms of Notch/lin-12 proteins that contain an intact intracellular domain without most of the extracellular domain behave as constitutively activated receptors (reviewed in Artavanis-Tsakonas et al., 1995; Greenwald, 1994). The human Notch 1 orthologue, TAN-1, was first identified in independently isolated translocation breakpoints in acute T lymphoblastic leukemia and is predicted to encode a truncated product that has an intact intracellular domain but lacks most of the extracellular domain (Ellisen et al., 1991). Similarly, the int-3 oncoprotein encodes the intracellular domain of a Notch-like protein and thus has been proposed to act as an activated Notch receptor (Robbins et al., 1992).

Based on sequence similarity to Drosophila Notch, additional Notch-related genes have been isolated from mammals; including mouse (Franco Del Amo et al., 1993; Lardelli et al., 1994; Lardelli and Lendahl, 1993; Reaume et al., 1992), rat (Weinmaster et al., 1992; Weinmaster et al., 1991), and human (Ellisen et al., 1991; Stifani et al., 1992; Sugaya et al., 1994). To date, three Notch homologues, Notch1, Notch2, and Notch3, have been identified in the mouse and their embryonic expression patterns display partially overlapping but distinct patterns of expression that are consistent with a potential role in the formation of the mesoderm, somites, and nervous system (Williams et al., 1995). Abundant expression of Notch1, Notch2, and Notch3 is found in proliferating neuroepithelium during central nervous system development. Targeted disruption of the Notch1 gene in mice results in embryonic death during the second half of gestation (Conlon et al., 1995; Swiatek et al., 1994) and homozygous mutant embryos display delayed somitogenesis as well as widespread cell death, preferentially in neuroepithelium and neurogenic neural crest (Conlon et al., 1995; Swiatek et al., 1994).

The gene products of Drosophila Delta (Vassin et al., 1987) and Serrate (Fleming et al., 1990), and *C. elegans* Lag-2 (Henderson et al., 1994; Tax et al., 1994) and Apx-1 (Mello et al., 1994) are thought to act as ligands for Notch proteins. In the mouse, the orthologue of Delta, referred to a Dll1 (Delta-like gene 1), is expressed during embryonic development in the paraxial mesoderm and nervous system in a pattern similar to that of mouse Notch1 (Bettenhausen et al., 1995). A murine Serrate-related gene named Jagged has been identified and is partially co-expressed with murine Notch genes in the developing spinal cord (Lindsell et al., 1995).

The identification and expression analysis of a fourth murine Notch homologue is reported here. The fourth murine Notch homologue has been named Notch4 and the int-3 nomenclature has been reserved for the truncated oncogene. Although the intracellular domain of the int-3 oncoprotein shares homology with the Notch/Lin-12 protein family, a comparison of the full length Notch4 protein to that of the int-3 oncoprotein is now provided. The activated int-3 protein encodes only the transmembrane and intracellular domain of the Notch4 protein. The predicted amino acid sequence of Notch4 contains the conserved features of all Notch proteins, however Notch4 has 7 fewer EGF-like repeats compared to Notch1 and Notch2 and contains a significantly shorter intracellular domain. Notch4 is expressed primarily in embryonic endothelium and in adult endothelium and male germ cells.

This invention uses an established cell line, Rat Brain Microvessel Endothelial cells (RBE4 cells), to test Notch4 activity and to demonstrate that activated Notch4 and Notch4 ligand stimulate angiogenesis in these cells. RBE4 cells grown on collagen coated plates in the absence of bFGF or with low concentrations of bFGF (1 ng/ml), display a cobblestone morphology. In the presence of high concentration of bFGF (5 ng/ml), RBE4 cells exhibit a spindle shape morphology. When RBE4 cells reach confluency, they growth arrest and cells retain their cobblestone morphology. Post-confluent RBE4 cell cultures grown in the presence of 5 ng/ml bFGF, develop multicellular aggregates from the cobblestone monolayer. These three-dimensional structures are sprouts that extend above the monolayer and some of these sprouts will organize into curvilinear and bifurcating structures that float in the cell culture medium. The RBE4 cell sprouts and three-dimensional structures contain high activity of several enzymatic markers that are specific for differentiated microvessels. Thus, bFGF, a known angiogenic agent, induces angiogenesis of RBE4 cells which upon treatment with high concentrations of bFGF develop structures resembling capillaries (based on their morphological appearance and based on their expression of differentiated endothelial cell markers).

The Notch1 and Jagged genes have been previously described to be expressed in mouse endothelial cells.

Contrary to previous studies suggesting that Jagged and Notch inhibit angiogenesis (Zimrin et al. J Biol Chem. 1996), this invention demonstrates that activated Notch4 protein and Jagged protein contain a biological activity on RBE4 cells that is similar to the known angiogenic agent basic fibroblast growth factor (bFGF), suggesting that the above-described biological activity is an angiogenic activity.

This invention demonstrates that RBE4 cells express an endogenous Notch, since RBE4 cells that are programmed to express Jagged (a mammalian Notch ligand) have a similar phenotype when compared to RBE4 cells that express a constitutive activated Notch (int-3). This is consistent with previously published data showing that Notch4 is expressed in endothelial cells in vivo.

This invention demonstrates that RBE4 cells do not express sufficient levels of Notch4 ligand to activate the Notch4 receptor, since RBE4 cells programmed to express Notch4 do not exhibit a spindle form morphology when grown in the absence of bFGF.

This invention also demonstrates that over expression of Notch4 protein in RBE4 cells does not result in activation of the Notch4 receptor, because otherwise one would expect that these cells would have a similar phenotype to those cells that express a constitutive activated form of the Notch4 receptor.

This invention also demonstrates that bFGF mediated angiogenesis is unrelated to Notch4 mediated angiogenesis. This invention further suggests that Jagged or activated Notch4 induced activity can synergize or cooperate with bFGF.

Notch signaling is typically associated with cell fate decision. The finding that Notch activation stimulates capillary outgrowth suggests that Notch receptors must be activated to allow this process to occur. Therefore, Notch modulation provides a novel paradigm for regulating angiogenesis. Specifically, modulation of Notch signaling can be used to modulate angiogenesis either positively, by activating Notch signaling to stimulate angiogenesis or negatively, by blocking Notch signaling to block angiogenesis. This modulation would be distinct from previous proteins known to modulate angiogenesis. The induction or inhibition of angiogenesis in vivo can be used as a therapeutic means to treat a variety of diseases, including but not limited to cancer, diabetes, wound repair and arteriosclerosis.

This invention provides three major advantages over previously published paradigms. First, because Notch signaling is distinct from FGF signaling, this offers a different strategy to affect angiogenesis that may or may not be more effective then FGFs. Second, because Notch signaling establishes cell fate decision, by blocking Notch, angiogenesis may be blocked regardless of what other angiogenic factors are present. Third, Notch and FGF may be used synergistically to modulate angiogenesis.

SUMMARY OF THE INVENTION

This invention provides an isolated nucleic acid molecule, encoding a Notch4 protein. This invention provides a vector comprising the above-described nucleic acid. This invention also provides an isolated Notch4 protein.

This invention also provides a plasmid which comprises the regulatory elements necessary for expression of DNA in a mammalian cell operatively linked to the DNA encoding Notch4 protein so as to permit expression thereof.

This invention also provides a mammalian cell comprising the above-described plasmid or vector.

This invention also provides a nucleic acid probe comprising a nucleic acid of at least 12 nucleotides capable of specifically hybridizing with a unique sequence included within the sequence of a nucleic acid encoding Notch4 protein.

This invention also provides an antisense oligonucleotide having a sequence capable of specifically hybridizing to mRNA encoding Notch4 protein so as to prevent translation of the mRNA.

This invention also provides an antisense oligonucleotide having a sequence capable of specifically hybridizing to mRNA encoding activated Notch4 protein so as to prevent translation of the mRNA.

This invention provides an antisense oligonucleotide having a sequence capable of specifically hybridizing to the genomic DNA encoding a Notch4 protein or an activated Notch4 protein.

This invention provides an antibody directed to a Notch4 protein. This invention provides a pharmaceutical composition comprising an amount of the oligonucleotide effective to reduce activity of Notch4 protein by passing through a cell membrane and binding specifically with mRNA encoding Notch4 protein in the cell so as to prevent its translation and a pharmaceutically acceptable carrier capable of passing through a cell membrane.

This invention provides a pharmaceutical composition comprising an amount of an antagonist effective to reduce the activity of Notch4 protein and a pharmaceutically acceptable carrier.

This invention provides a pharmaceutical composition comprising an amount of an agonist effective to increase activity of Notch4 protein and a pharmaceutically acceptable carrier.

This invention provides the above-described pharmaceutical composition which comprises an amount of the antibody effective to block binding of a ligand to the Notch4 protein and a pharmaceutically acceptable carrier.

This invention also provides a method for determining whether a ligand can specifically bind to Notch4 protein comprising the steps of: a) contacting Notch4 protein with the ligand under conditions permitting formation of specific complexes between Notch4 protein and known Notch4 protein-binding ligands; b) determining whether complexes result from step (a), the presence of such complexes indicating that the ligand specifically binds to Notch4 protein.

This invention provides a method for determining whether a ligand can specifically bind to a Notch4 protein which comprises preparing a cell extract from cells transfected with and expressing DNA encoding the Notch4 protein, isolating a membrane fraction from the cell extract, contacting the membrane fraction with the ligand under conditions permitting binding of ligands to such Notch4 protein, detecting the presence of the ligand specifically bound to Notch4 protein, and thereby determining whether the ligand specifically binds to Notch4 protein.

This invention provides a method for determining whether a ligand is a Notch4 protein agonist which comprises contacting a cell transfected with and expressing nucleic acid encoding Notch4 protein with the ligand under conditions permitting activation of a functional Notch4 protein response by ligands known to be agonists of Notch4 protein, and detecting whether a functional increase in Notch4 protein activity occurs so as to determine whether the ligand is a Notch4 agonist.

This invention provides a method for determining whether a ligand is a Notch4 protein antagonist which comprises contacting a cell transfected with and expressing DNA encoding Notch4 protein with the ligand under conditions permitting the activation of a functional Notch4 protein, and detecting whether a functional decrease in Notch4 activity occurs so as to determine whether the ligand is a Notch4 protein antagonist.

This invention provides a method of treating an abnormality in a subject, wherein the abnormality is alleviated by the inhibition of Notch4 protein activity which comprises administering to a subject an amount of Notch4 antagonist effective to inhibit Notch4 protein activity.

This invention provides a method of treating an abnormality in a subject wherein the abnormality is alleviated by the activation of Notch4 activity which comprises administering to a subject an amount of a Notch4 agonist effective to promote Notch4 protein activity.

This invention provides a method of preparing isolated Notch4 protein which comprises: a) inserting nucleic acid encoding Notch4 protein in a suitable vector which comprises the regulatory elements necessary for expression of the nucleic acid operatively linked to the nucleic acid encoding Notch4 protein; b) inserting the resulting vector in a suitable host cell so as to obtain a cell which produces Notch4 protein; c) recovering the Notch4 protein produced by the resulting cell; and d) purifying the protein so recovered.

This invention also provides a method of modulating angiogenesis in a subject comprising administering to the subject an effective amount of agonist or antagonist of the Notch4 protein so as to promote or inhibit angiogenesis in the subject.

This invention also provides a method of promoting angiogenesis in a subject comprising administering to the subject an amount of Notch4 protein agonist effective to promote angiogenesis in the subject.

This invention also provides method of inhibiting angiogenesis in a subject comprising administering to the subject an amount of Notch4 protein antagonist effective to inhibit angiogenesis in the subject.

This invention also provides method of promoting angiogenesis comprising transducing selected cells, wherein the cells express activated Notch4 protein in an amount sufficient promote angiogenesis in the cells.

This invention provides a method of promoting angiogenesis comprising transducing selected cells which express Notch4 protein, wherein the cells express a Notch4 ligand in an amount sufficient to promote angiogenesis in the cells.

This invention provides a method of promoting angiogenesis comprising transducing selected cells, wherein the cells express a Notch4 protein and a Notch4 ligand in an amount sufficient to promote angiogenesis in the cells.

This invention provides a method of inhibiting angiogenesis comprising administering to cells expressing Notch4 protein an amount of a specific antibody effective to block binding of a ligand to Notch4 protein.

This invention provides a method of inhibiting angiogenesis comprising administering to cells expressing Notch4 protein an amount of a fragment of a specific antibody effective to block binding of a ligand to Notch4 protein.

This invention provides a method of treating an abnormality in a subject wherein the abnormality is alleviated by inhibiting angiogenesis comprising blocking Notch4 protein signaling in the subject.

This invention also provides a method of treating an abnormality in a subject wherein the abnormality is alleviated by promoting angiogenesis comprising stimulating the Notch4 signaling pathway.

BRIEF DESCRIPTION OF THE FIGURES

FIGS. 1A–1B Deduced amino acid sequence (SEQ ID NO:1) of Notch4 (GenBank accession number U43691). The boxed regions indicate the major structural elements of the Notch family of proteins, as follows: 29 epidermal growth factor (EGF)-like repeats; 3 Notch/lin12 repeats; a transmembrane domain; and 6 cdc10/ankyrin repeats. Putative glycosylation sites are underlined. A putative PEST domain is doubly underlined. The two cysteines thought to promote dimerization are marked with asterisks. The initiating methionine of the int-3 oncoprotein is in bold and marked by an arrow.

FIG. 3 Amino acid sequence comparison of EGF-like repeat #11 of mouse Notch1, 2, 3 and 4 (SEQ ID NOS:2–5, respectively). Residues conserved between the mouse Notch proteins are shaded and the putative calcium-binding sites are marked with arrows. A region within EGF-like repeat

11 of the Notch proteins containing non-conserved and variable numbers of residues is boxed. The leucine to proline mutation in Xenopus Notch that obliterates binding to Delta is marked with an asterisk (*).

FIG. 4A–4B Expression analysis of Notch4 in adult mouse tissues. (A) Northern blot using a riboprobe transcribed from the 3' UTR of Notch4 (probe D in FIG. 5). (B) The same blot reprobed with a GAPDH probe. The transcript sizes of 6.7 kb, 1.5 kb and 1.1 kb are indicated and were estimated with reference to 28S and 18S rRNA migration.

Figure 5C:
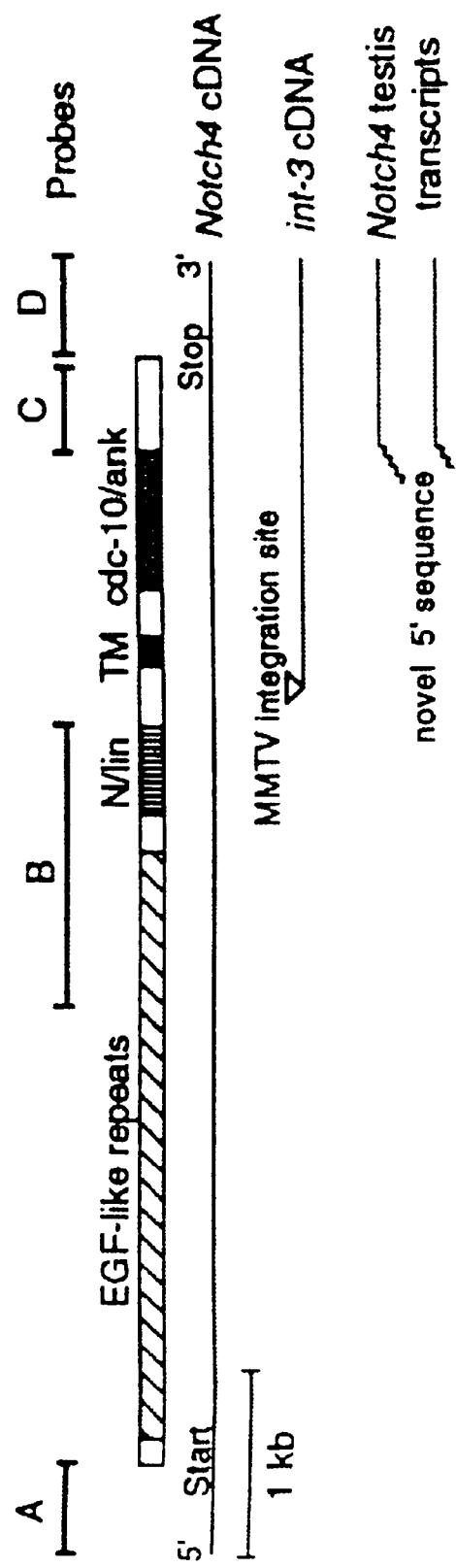

FIGS. 5A–5C Expression analysis of Notch4 testis transcripts. (A) Notch4 testis transcripts are expressed in post-meiotic germ cells. Northern blot analysis from staged and germ cell-deficient testes with probe C and a GAPDH probe. Note that GAPDH transcripts appear as two isoforms in the adult testis. RNA was isolated from testes of day 7 p.n., day 17 p.n., adult, $W^v/W$ and W/+mice, as indicated. (B) Northern blot analysis of several adult tissues with probe A, derived from the 5' UTR of Notch4 and a GAPDH probe. (C) Schematic representation of truncated Notch4 transcripts as compared to the full-length coding potential. Relative positions of probes used in the northern blot analysis are shown. Conserved elements of Notch Family proteins are indicated. The MMTV integration site reported by Robbins et al. (1992) is indicated by an arrow. Novel 5' sequences of testes cDNAs are indicated.

FIGS. 6A–6F Notch4 is expressed in embryonic endothelial cells. (A,B) Phase contrast and dark-field photomicrograph of a horizontal section of a 9 d.p.c. embryo hybridized with a cRNA probe corresponding to Notch4. Strong labeling is detectable over the anterior cardinal vein (white/black arrows). Diffuse labeling is also present throughout the developing nervous system and at higher levels over the tip of the neural folds (red arrows). (C-F) Phase and darkfields images of a horizontal section of a 13.5 d.p.c embryo hybridized for Notch4, showing the venous and arterial system anterior to the lung, including dorsal aorta arch, aortic and pulmonary tract. E and F are higher magnifications of the area framed in C. Embryonic vessels are labeled and, as shown in E and F, labeling is restricted to the endothelial cells lining the vessels. Arrows denote the gut, which does not have a detectable signal in the epithelium.

FIGS. 7A–7B Notch4 is expressed in adult lung endothelial cells. (A, B) Phase contrast and darkfield photomicrographs of an adult mouse lung hybridized with a cRNA probe corresponding to Notch4. Punctate staining is observed over the alveolar walls, which are predominantly composed of capillaries. No labeling is observed over the pseudostratified squamous epithelium (black and white arrows) nor over the smooth muscle cells (red arrows).

Figure 8E:
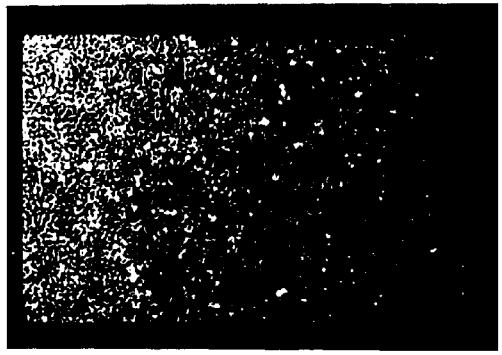
Figure 8F:
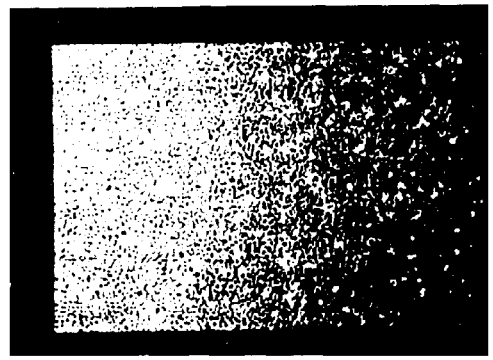
Figure 8G:
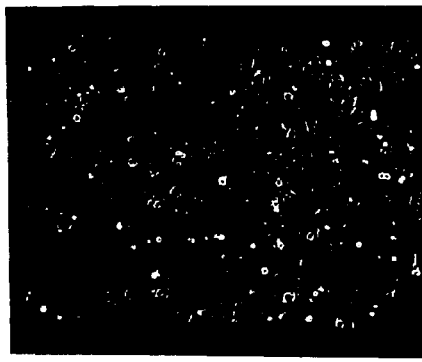
Figure 8H:
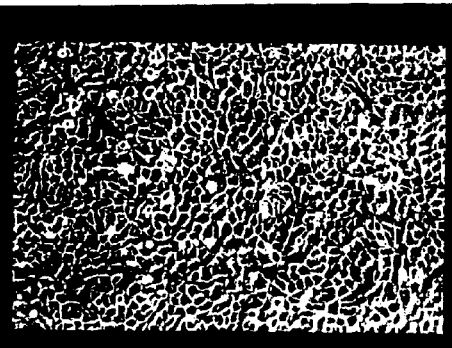
Figure 8I:
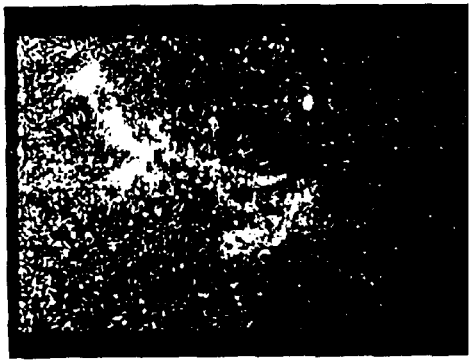
Figure 8J:
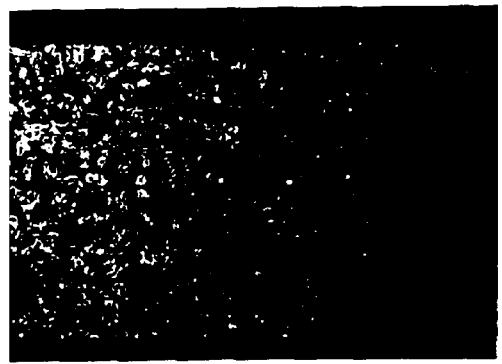
Figure 8K:
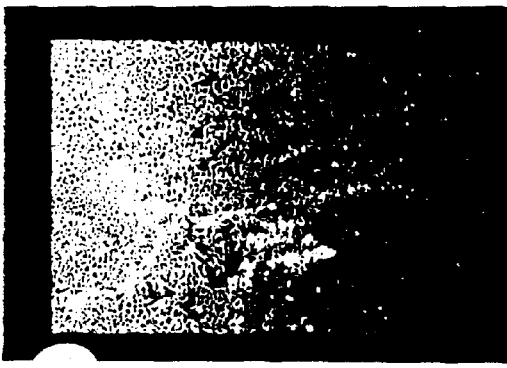
Figure 8L:
Figures 8U, 8V:
Figures 8W, 8X:
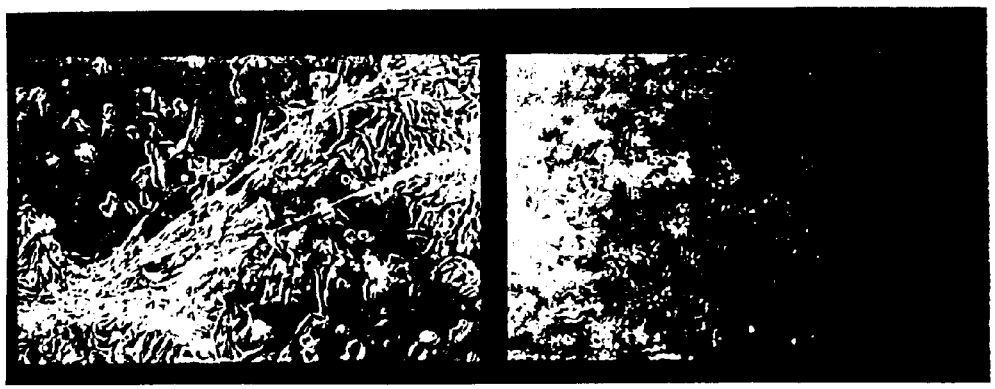
Figure 10A:
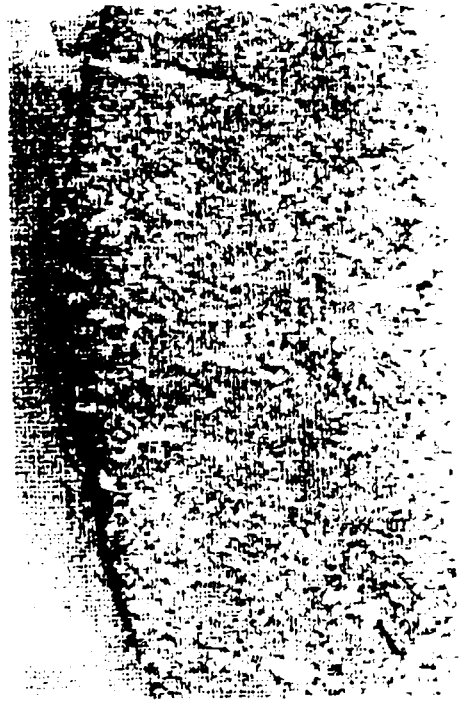
Figure 10B:
Figure 10C:
Figure 10D:
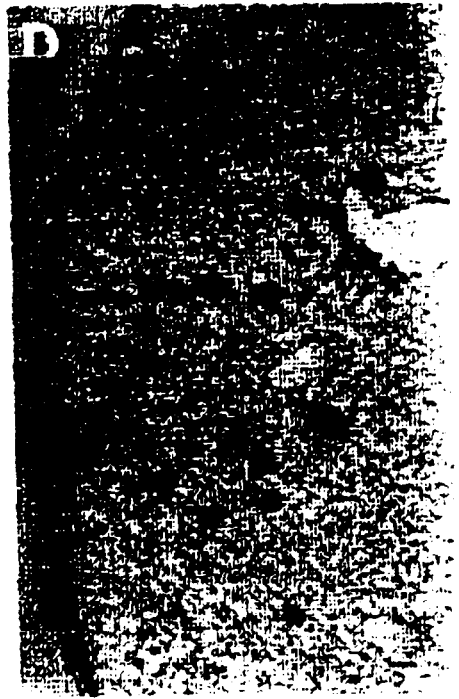
Figure 11A:
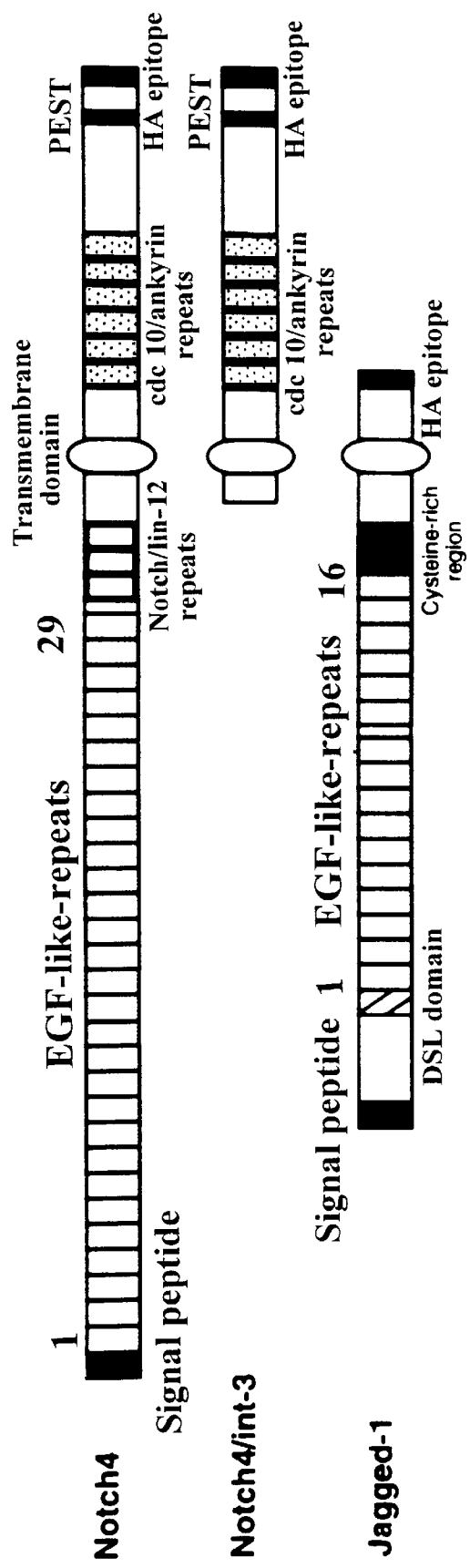
Figure 11B:
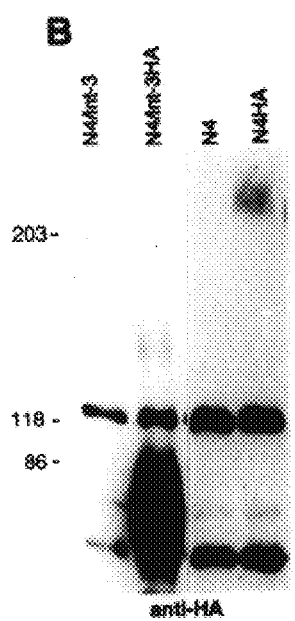
Figure 11C:
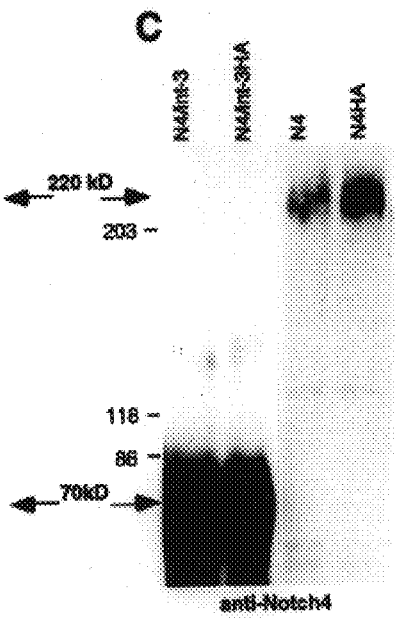
Figure 11D:
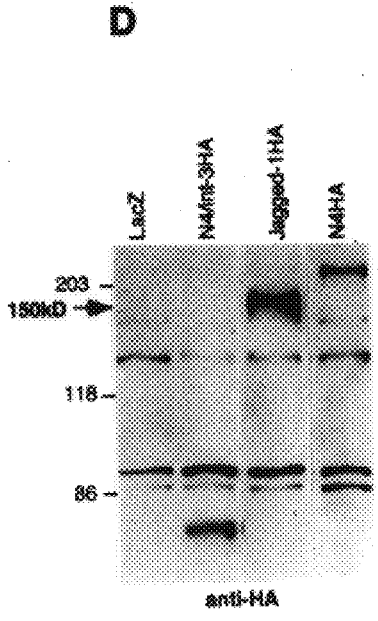
Figure 12A:
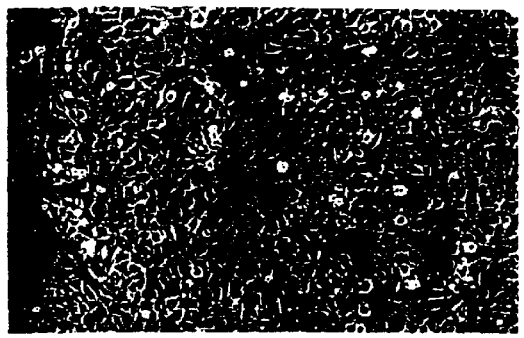
Figure 12B:
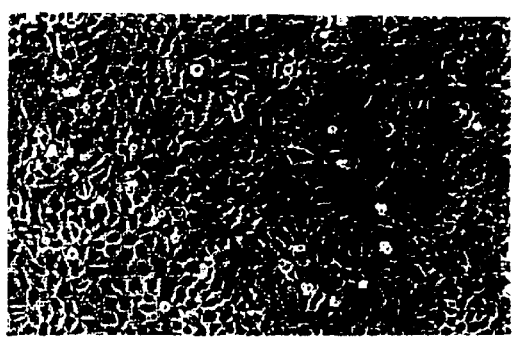
Figure 12C:
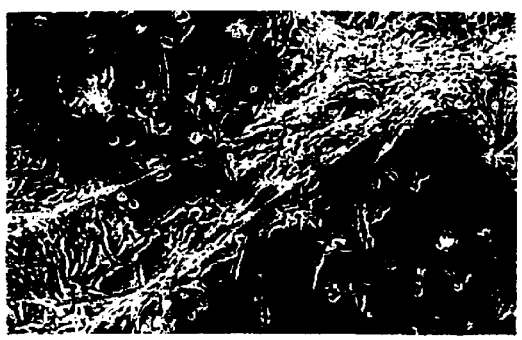
Figure 12D:
Figure 12E:
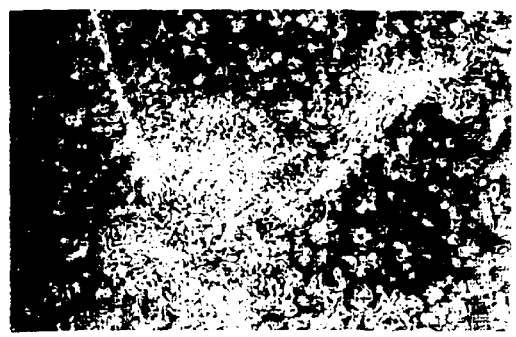
Figure 12F:

FIGS. 8A–8X RBE4 cell lines grown on collagen coated plates in the absence of bFGF. (A) RBE4/LacZ, low magnification, ⅛ sec exposure; (B) RBE4/LacZ, high magnification, ⅛ sec exposure; (C) RBE4/LacZ, low magnification, ¼ sec exposure; (D) RBE4/LacZ, high magnification, ¼ sec exposure: (E) RBE4/Notch4, low magnification, ¼ sec exposure; (F) RBE4/Notch4, low magnification, ⅛ sec exposure; (G) RBE4/Notch4, high magnification, ¼ sec exposure; (H) RBE4/Notch4, high magnification, ⅛ sec exposure; (I) RBE4/Jagged, low magnification, ¼ sec exposure; (J) RBE4/Jagged, low magnification, ⅛ sec exposure; (K) RBE4/Jagged, low magnification, ⅛ sec exposure; (L) RBE4/Jagged, low magnification, ¼ sec exposure; (M) RBE4/Jagged, high magnification, ¼ sec exposure: (N)RBE4/Jagged, high magnification, ⅛ sec exposure; (O) RBE4/Jagged, high magnification, ¼ sec exposure; (P) RBE4/Jagged, high magnification, ¼ sec exposure; (Q) RBE4/int-3, low magnification, ⅛ sec exposure; (R) RBE4/int-3, low magnification, ⅛ sec exposure; (S) RBE4/int-3, low magnification, ¼ sec exposure; (T) RBE4/int-3, low magnification, ¼ sec exposure; (U) RBE4/int-3, high magnification, ⅛ sec exposure; (V) RBE4/int-3, high magnification, ⅛ sec exposure; (W) RBE4/int-3, high magnification, ¼ sec exposure; (X) RBE4/int-3, low magnification, ¼ sec exposure.

FIGS. 9A–9D Nucleic acid sequence (SEQ ID NO:6) of Notch4 (GenBank Accession No. U43691).

FIGS. 10A–10D Immunohistochemical analysis on adult mouse kidney sections. Endothelial cells within the cortical kidney glomeruli can be detected by using either an anti-PECAM antibody (B) or an antibody was used in panel B, and both panel A and B were processed for horse radish peroxidase detection which results in a brown staining. Pre-immune serum at identical dilution was used in panel C, and both panel C and D were processed for alkaline phosphatase detection which results in a blue-purple staining. Panels C and D were counter stained with eosin.

FIGS. 11A–11D Schematic representation of the notch4, Notch4/int-3 and Jagged-1 proteins (A). Conserved domains within each proteins are indicated. Immunoblot analysis on lysates of 293 cells transiently transfected with either epitope tagged or non-epitope tagged cDNA's of Notch4/int or Notch4 (B and C) using anti-HA antibody (B) or anti-Notch4 antibody (C). Immunoblot analysis on lysates of RBE4 cells programmed to express LacZ, Notch4/int-3, Jagged-1 or Notch4 using the anti-HA antibody, demonstrates expression of each respective protein (D).

FIGS. 12A–12F RBE4 cells that are programmed to express either LacZ (A) or Notch4 (B) display a cobble stone morphology when grown on collagen coated plates. RBE4 cells programmed to express Notch4/int-3 (C and E) or Jagged-1 (D and E) display a spindle shape morphology and spontaneously form microvessel structures. Structures were more prominent in RBE-Notch4/int-3 than in RBE-Jagged-1 cell cultures (compare E to F). Photographs A to D were taken at 100×magnification whereas photographs E and F were taken at 40×magnification.

Figure 13A:
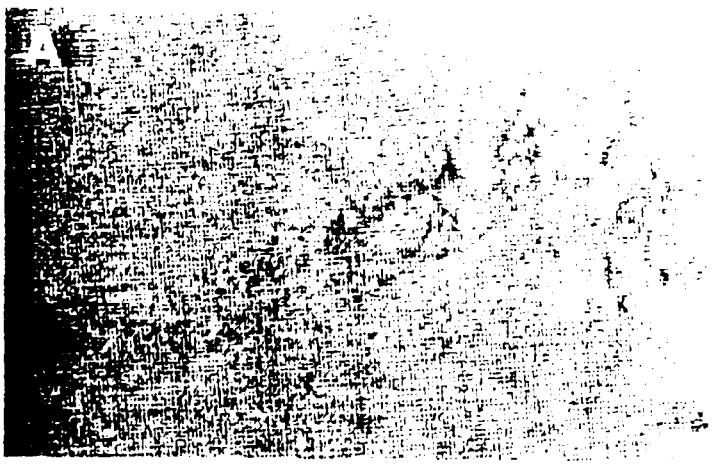
Figure 13B:
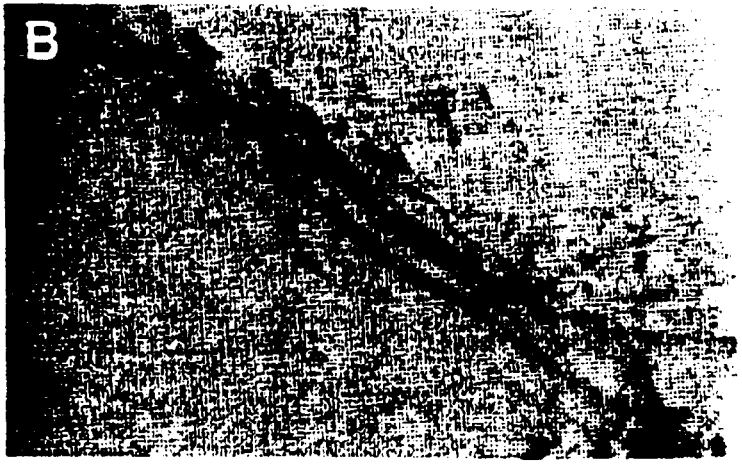
Figure 13C:
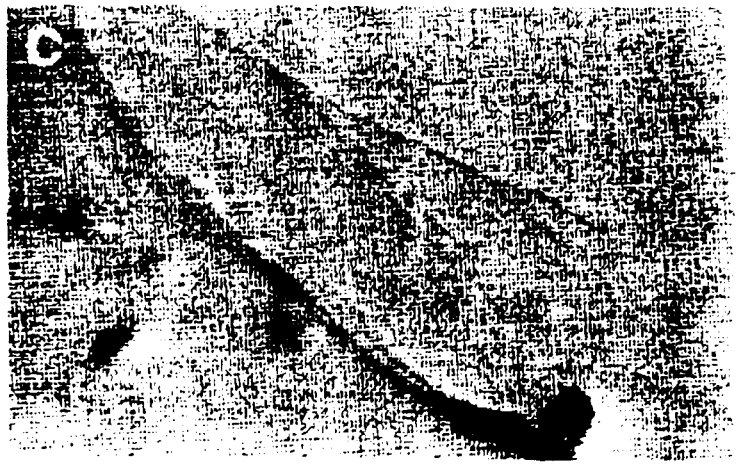

FIGS. 13A–13C Histochemical analysis of alkaline phosphatase (B) and gamma-glutamyl transpeptidase© activities in microvessel structures induced by RBE4 cells expressing Notch4/int-3 (B) or Jagged-1 (C). RBE4 cells surrounding the microvessel structures do not express either enzyme activity (B and C). Panel A is control.

Figure 14A:
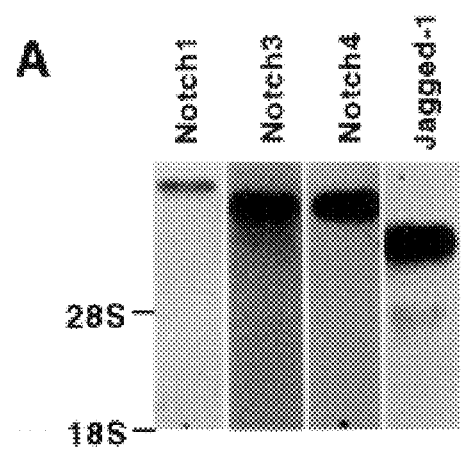
Figure 14B:
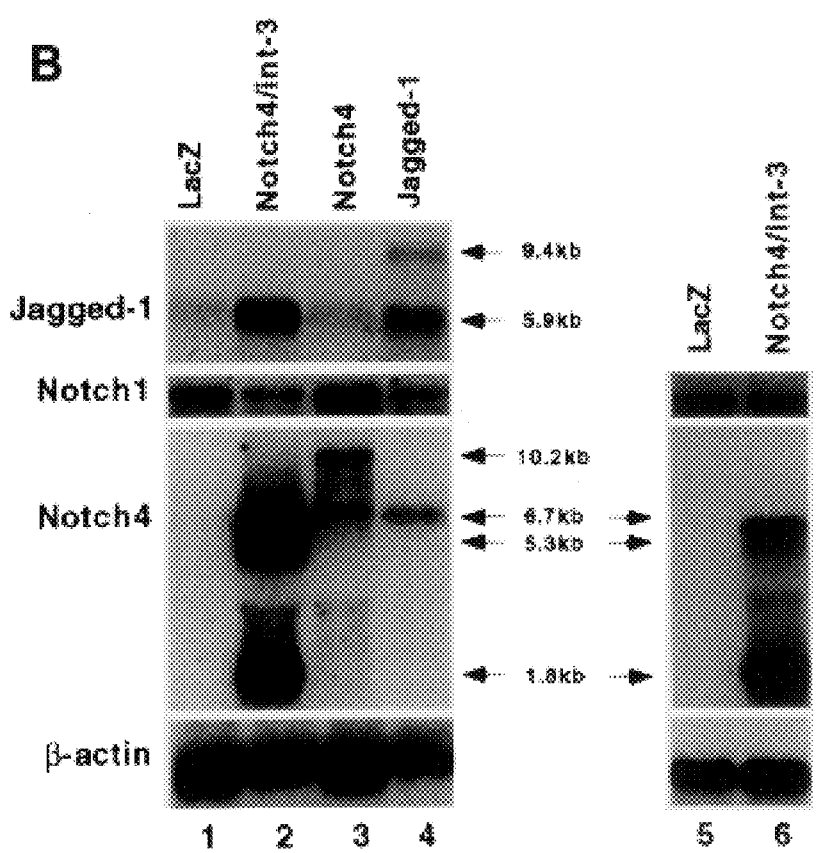

FIGS. 14A–14B Northern blot analysis on RBE4 cells. Panel A, 40 µg of total RNA (lane 2 and 4) from RBE4 cells programmed to express either LacZ, Notch4/int-3, Notch4 or Jagged-1, was hybridized to riboprobes for either Jagged-1, Notch1, Notch4 or β-actin. LTR-driven transcripts are denoted (LTR).

DETAILED DESCRIPTION OF THE INVENTION

This invention is illustrated in the Experimental Details section which follows. These sections are set forth to aid in an understanding of the invention but are not intended to, and should not be construed to, limit in any way the invention as set forth in the claims which follow thereafter.

Throughout this application, the following standard abbreviations are used to indicate specific nucleotide bases:

| | |
|---|---|
| C = cytosine | A = adenine |
| T = thymine | G = guanine |

The activity of a protein such as a Notch4 protein may be measured using any of a variety of appropriate functional assays in which activation of the protein in question results in an observable change in the level of some second messenger system.

This invention provides an isolated nucleic acid encoding Notch4 protein.

This invention provides the Notch4 nucleic acid, wherein the nucleic acid is a DNA. In an embodiment, the Notch4 nucleic acid has the nucleic acid sequence as described in FIG. 9. In an embodiment, the DNA is a cDNA. In another embodiment, the DNA is a genomic DNA. In another embodiment the DNA is synthetic DNA. In still another embodiment, the nucleic acid is RNA. In a separate embodiment, the nucleic acid encodes Notch4 protein. As used herein, Notch4 protein has the amino acid sequence as described in FIG. 1.

As used herein, Notch4 protein includes any polypeptide having Notch4 protein activity and having an amino acid sequence homologous to the amino acid sequence of Notch4. Thus, this term includes any such polypeptides whether naturally occurring and obtained by purification from natural sources or non-naturally occurring and obtained synthetically, e.g. by recombinant DNA procedures. Moreover, the term includes any such polypeptide where its sequence is substantially the same as, or identical to the sequence of any mammalian homolog of the human polypeptide, e.g. murine, bovine, porcine, etc. homologs. Additionally, the term includes mutants or other variants of any of the foregoing which retain at least some of the biological activity of nonmutants or nonvariants.

This invention also encompasses DNAs and cDNAs which encode amino acid sequences which differ from those of Notch4 protein, but which should not produce phenotypic changes. In addition, this invention also encompasses DNAs and cDNAs which hybridize to the DNA and cDNA of the subject invention. Hybridization methods are well known to those of skill in the art.

This invention provides an isolated nucleic acid encoding an activated Notch4 protein.

The nucleic acid of the subject invention also include DNA coding for polypeptide analogs, fragments or derivatives of polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids described and claimed herein are useful for the information which they provide concerning the amino acid sequence of the polypeptide and as products for the large scale synthesis of the polypeptide by a variety of recombinant techniques. The nucleic acid is useful for generating new cloning and expression vectors, transformed and transfected prokaryotic and eukaryotic host cells, and new and useful methods for cultured growth of such host cells capable of expression of the polypeptide and related products.

This invention also provides an isolated Notch4 protein. In one embodiment the Notch4 protein has the amino acid sequence as shown in FIG. 1.

This invention provides a vector comprising the above-described nucleic acid.

Vectors which comprise the isolated nucleic acid described hereinabove also are provided. Suitable vectors comprise, but are not limited to, a plasmid or a virus. These vectors may be transformed into a suitable host cell to form a host cell vector system for the production of a polypeptide having the biological activity of Notch4 protein.

This invention provides the above-described vector adapted for expression in a cell which further comprises the regulatory elements necessary for expression of the nucleic acid in the cell operatively linked to the nucleic acid encoding Notch4 protein as to permit expression thereof.

This invention provides the above-described vector adapted for expression in a bacterial cell which further comprises the regulatory elements necessary for expression of the nucleic acid in the bacterial cell operatively linked to the nucleic acid encoding Notch4 protein so as to permit expression thereof.

This invention provides the above-described vector adapted for expression in a yeast cell which comprises the regulatory elements necessary for expression of the nucleic acid in the yeast cell operatively linked to the nucleic acid encoding Notch4 protein so as to permit expression thereof.

This invention provides the above-described vector adapted for expression in a plant cell which comprises the regulatory elements necessary for expression of the nucleic acid in the insect cell operatively linked to the nucleic acid encoding Notch4 protein so as to permit expression thereof.

In an embodiment, the vector is adapted for expression in a animal cell which comprises the regulatory elements necessary for expression of the DNA in the animal cell operatively linked to the DNA encoding animal Notch4 protein so as to permit expression thereof.

This invention provides a plasmid which comprises the regulatory elements necessary for expression of DNA in a cell operatively linked to the DNA encoding Notch4 protein so as to permit expression thereof designated pBS-Notch4 (ATCC Designation No. 209121.

This plasmid (pBS-Notch4) was deposited on Jun. 12, 1997, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. U43691.

This invention provides a mammalian cell comprising the above-described plasmid or vector. In an embodiment, the mammalian cell is a Rat Brain Microvessel endothelial (RBE4) cell.

This invention provides a method of transforming host cells produced by transfecting host cells with the above-described vector.

This invention provides a nucleic acid probe comprising a nucleic acid molecule of at least 12 nucleotides capable of specifically hybridizing with a unique sequence included within the sequence of a nucleic acid molecule encoding Notch4 protein. In an embodiment, the nucleic acid is DNA.

The nucleic acid probe can either be DNA or RNA. As used herein, the phrase "specifically hybridizing" means the ability of a nucleic acid to recognize a nucleic acid sequence complementary to its own and to form double-helical segments through hydrogen bonding between complementary base pairs.

This nucleic acid of at least 12 nucleotides capable of specifically hybridizing with a sequence of a nucleic acid encoding Notch4 can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe. molecules may be produced by insertion of a DNA molecule which encodes Notch4 into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA which encodes Notch4 protein downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention also provides a nucleic acid of at least 12 nucleotides capable of specifically hybridizing with a sequence of a nucleic acid which is complementary to the mammalian nucleic acid encoding Notch4 protein. This nucleic acid may either be a DNA or RNA molecule.

This invention provides an antisense oligonucleotide having a sequence capable of specifically hybridizing to mRNA encoding Notch4 protein so as to prevent translation of the mRNA.

This invention provides an antisense oligonucleotide having a sequence capable of specifically hybridizing to the genomic DNA of Notch4 protein or activated Notch4 protein.

This invention provides an antisense oligonucleotide of Notch4 comprising chemical analogues of nucleotides.

This invention provides an antibody directed to Notch4 protein. This invention also provides an antibody directed to activated Notch4 protein.

As used herein, the term "antibody" encompasses fragments of the antibody such that fragments are capable of binding to the specific antigen. Antibody also includes polypeptides which have the antigen binding domains. Such polypeptide may contain a single chain known as single-chain antibody. As used herein, peptide encompasses both polypeptide and oligopeptide.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian PSM antigen in living animals, in humans, or in biological tissues or fluids isolated from animals or humans.

This invention provides a monoclonal antibody directed to an epitope of Notch4 present on the surface of a Notch4 receptor expressing cell.

This invention provides a pharmaceutical composition comprising an amount of the oligonucleotide effective to reduce activity of Notch4 protein by passing through a cell membrane and binding specifically with mRNA encoding Notch4 in the cell so as to prevent its translation and a pharmaceutically acceptable carrier capable of passing through a cell membrane. In an embodiment, the oligonucleotide is coupled to a substance which inactivates mRNA.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type.

This invention provides a pharmaceutical composition comprising an amount of an antagonist effective to reduce the activity of Notch4 protein and a pharmaceutically acceptable carrier.

This invention provides a pharmaceutical composition comprising an amount of an agonist effective to increase activity of Notch4 protein and a pharmaceutically acceptable carrier.

This invention provides the above-described pharmaceutical composition which comprises an amount of the antibody effective to block binding of a ligand to the Notch4 protein and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention also provides a method for determining whether a ligand can specifically bind to Notch4 which comprises contacting a cell transfected with and expressing DNA encoding Notch4 with the ligand under conditions permitting binding of ligands to Notch4, detecting the presence of any such ligand specifically bound to Notch4, and thereby determining whether the ligand specifically binds to Notch4.

This invention provides a method for determining whether a ligand can specifically bind to Notch4 protein comprising the steps of: a)contacting Notch4 protein with the ligand under conditions permitting formation of specific complexes between Notch4 protein and known Notch4 protein-binding ligands; b) determining whether complexes result from step (a), the presence of such complexes indicating that the ligand specifically binds to Notch4 protein.

In one embodiment, the Notch4 protein in step (a) described above, is reconstituted in liposomes. In another embodiment, the ligand is not previously known to be a ligand which can specifically bind to Notch4 protein.

This invention provides a method for determining whether a ligand can specifically bind to Notch4 which comprises contacting a cell transfected with and expressing DNA encoding Notch4 with the ligand under conditions permitting binding of ligands to Notch4, detecting the presence of any such ligand specifically bound to Notch4, and thereby determining whether the ligand specifically binds to Notch4, such Notch4 having substantially the same amino acid sequence shown in FIG. 1.

This invention provides a method for determining whether a ligand can specifically bind to Notch4 which comprises contacting a cell transfected with and expressing DNA encoding Notch4 with the ligand under conditions permitting binding of ligands to Notch4, detecting the presence of any such ligand specifically bound to Notch4, and thereby determining whether the ligand specifically binds to Notch4, such Notch4 being characterized by an amino acid sequence in the transmembrane region having 60% homology or higher to the amino acid sequence in the transmembrane region of Notch4 shown in FIG. 1.

This invention provides a method for determining whether a ligand can specifically bind to Notch4 which comprises preparing a cell extract from cells transfected with and expressing DNA encoding Notch4, isolating a membrane fraction from the cell extract, contacting the membrane fraction with the ligand under conditions permitting binding of ligands to such protein, detecting the presence of the ligand specifically bound to Notch4, and thereby determining whether the ligand specifically binds to Notch4.

This invention provides a method for determining whether a ligand can specifically bind to Notch4 which comprises preparing a cell extract from cells transfected with and expressing DNA encoding Notch4, isolating a membrane fraction from the cell extract, contacting the membrane fraction with the ligand under conditions permitting binding of ligands to Notch4, detecting the presence of the ligand specifically bound to Notch4, and thereby determining whether the ligand can specifically bind to Notch4, such Notch4 having substantially, the same amino acid sequence shown in FIG. 1.

This invention provides a method for determining whether a ligand is a Notch4 protein agonist which comprises contacting a cell transfected with and expressing Notch4 protein with the ligand under conditions permitting activation of a functional Notch4 protein response by ligands known to be agonists of Notch4 protein, and detecting whether a functional increase in Notch4 protein activity occurs so as to determine whether the ligand is a Notch4 protein agonist.

The term "agonist" is used throughout this application to indicate any peptide or non-peptidyl compound which increases the activity of any of the receptors/proteins of the subject invention.

This invention provides a method for determining whether a ligand is a Notch4 protein antagonist which comprises contacting a cell transfected with and expressing Notch4 protein with the ligand under conditions permitting activation of a functional Notch4 protein response by ligands known to be agonists of Notch4 protein, and detecting whether a functional decrease in Notch4 protein activity occurs so as to determine whether the ligand is a Notch4 antagonist.

The term "antagonist" is used throughout this application to indicate any peptide or non-peptidyl compound which decreases the activity of any of the receptors/proteins of the subject invention.

This invention provides a pharmaceutical composition which comprises an amount of a Notch4 protein agonist effective to increase the activity of a Notch4 protein within a cell and a pharmaceutically acceptable carrier. In an embodiment, the pharmaceutical composition of comprises a peptide fragment of Jagged protein capable of increasing the activity of Notch4 protein.

This invention also provides a pharmaceutical composition which comprises an amount of a Notch4 protein antagonist effective to decrease activity of Notch4 protein within a cell and a pharmaceutically acceptable carrier.

This invention provides a method of modulating angiogenesis in a subject comprising administering to the subject an amount of agonist or antagonist of Notch4 protein effective to promote or inhibit angiogenesis in the subject.

This invention provides a method of promoting angiogenesis in a subject comprising administering to the subject an amount of Notch4 protein agonist effective to promote angiogenesis in the subject.

This invention provides a method of inhibiting angiogenesis in a subject comprising administering to the subject an amount of Notch4 protein antagonist effective to inhibit angiogenesis in the subject.

This invention provides a method of promoting angiogenesis comprising transducing selected cells, wherein the cells express activated Notch4 protein in an amount sufficient promote angiogenesis in the cells.

This invention provides a method of promoting angiogenesis comprising transducing selected cells which express Notch4 protein, wherein the cells express a Notch4 ligand in an amount sufficient to promote angiogenesis in the cells.

This invention provides a method of promoting angiogenesis comprising transducing selected cells, wherein the cells express a Notch4 protein and a Notch4 protein ligand in an amount sufficient to promote angiogenesis in the cells. In an embodiment, the Notch4 protein ligand is Jagged protein or a peptide fragment thereof capable of increasing the activity of Notch4 protein.

This invention provides a method of inhibiting angiogenesis comprising administering to cells expressing Notch4 protein an amount of an antibody of effective to block binding of a ligand to Notch4 protein.

This invention also provides a method of inhibiting angiogenesis comprising administering to cells expressing Notch4 protein an amount of a fragment of antibody effective to block binding of a ligand to Notch4 protein.

This invention provides a method of treating an abnormality in a subject wherein the abnormality is alleviated by inhibiting angiogenesis comprising blocking Notch4 protein signaling in the subject. In an embodiment, the above-described method comprises administering to the subject an amount of an antibody effective to block binding of a ligand to Notch4 protein. In another embodiment, the above-described method of treating an abnormality in a subject comprises administering to the subject an amount of a fragment of an antibody effective to block binding of a ligand to Notch4 protein. In another embodiment, the abnormality is a solid tumor, hemangioma, hemangiosarcoma or Kaposi's Sarcoma.

This invention provides a method of treating an abnormality in a subject wherein the abnormality is alleviated by promoting angiogenesis comprising stimulating the Notch4 signaling pathway. In an embodiment, the above-described method of treatment comprises transducing selected cells within the subject, wherein the cells express activated Notch4 protein. In another embodiment, the above-described method of treatment comprises transducing selected cells within the subject expressing a Notch4 protein such that the cells express a Notch4 protein ligand. In another embodiment, the above-described method of treatment comprises transducing selected cells within the subject such that the cells express a Notch4 protein and a Notch4 protein ligand. In an embodiment, the ligand is Jagged protein or a peptide fragment thereof capable of increasing the activity of Notch4 protein.

In an embodiment, the abnormality is an ischemic disorder, gangrene, diabetes ulceratis, chronic ulceration, Cerebral Autosomal Dominant Arteriopathy with Subcortical Infarcts and Leukoencephalopathy (CADASIL), Vascular Dementia or a wound.

This invention provides a method of detecting expression of Notch4 by detecting the presence of mRNA coding for Notch4 which comprises obtaining total mRNA from the cell and contacting the mRNA so obtained with the above-described nucleic acid probe under hybridizing conditions, detecting the presence of mRNA hybridized to the probe, and thereby detecting the expression of Notch4 by the cell.

This invention provides a method of detecting the presence of Notch4 on the surface of a cell which comprises contacting the cell with the antibody capable of binding to Notch4 under conditions permitting binding of the antibody to the receptor, detecting the presence of the antibody bound to the cell, and thereby detecting the presence of Notch4 on the surface of the cell.

Experimental Details

First Series of Experiments

Materials and Methods

Isolation and Sequencing of Notch4 cDNA Clones

A 1680 bp fragment was amplified by PCR from adult mouse testis cDNA (RT-PCR) using specific primers (5' primer: CGTCCTGCTGCGCTTCCTTGCA [(Seq. I.D. No.)] (SEQ ID NO:7) and 3' primer CCGGTGCCTAGTTCAGATTTCTTA) (SEQ ID NO: 8) designed from the int-3 cDNA sequence (Robbins et al., 1992). This cDNA fragment corresponds to the previously cloned int-3 oncogene. Two consecutive 5' RACE reactions (5'-Amplifinder RACE kit, Clonetech®) using testis and lung cDNA were done to obtain cDNA clones located 5' of the int-3 oncogene. The above described cDNAs were cloned into Bluescript KS (Stratagene®) and the TA cloning vector (Invitrogen®) and used to generate probes to screen a lung cDNA library (Clonetech®). Briefly, nitrocellulose membranes (Schleicher&Schuell) were hybridized in a solution containing 50% Formamide, 3×SSC, 100 mM Tris-HCl (ph 7.4), 5×Denhardt's solution, 0.2% SDS, and 0.1 mg/ml salmon sperm DNA at 42° C. for 14 hours. Filters were then washed in 1×SSC and 0.5% SDS at room temperature followed by washes at 65° C. Positive clones were purified and sequenced to confirm overlapping regions. Novel 5' restriction fragments of these newly isolated clones were used in consecutive screens in order to obtain the full length Notch4 cDNA. All the above described clones were sequenced using the dideoxy termination method (Sanger) with an automatic DNA sequencer (Applied Biosystems®). Sequence data from both strands were obtained for the entire Notch4 cDNA and were analyzed and assembled using computer software (MacVector®).

Northern Blot Analysis

Total RNA was isolated from adult CD-1 mouse tissues and Northern blot hybridization analysis was performed. 20 μg of total RNA was electrophoresed on a 1% agarose gel containing 6% formaldehyde. After electrophoresis RNAs were transferred to a nylon membrane (Duralon-UV membranes®, Stratagene®) by capillary blotting. $^{32}$p-radiolabeled riboprobes were transcribed (Maxiscript® in vitro transcription kit, Ambion®) from Notch4 cDNA clones encoding the 5' or 3' UTR (untranslated region) or ORF (open reading frame). The 3' UTR Notch4 cDNA clone was isolated by RT-PCR and a 440 bp restriction fragment of this cDNA was used as riboprobe. Hybridization solution contained 60% Formamide, 5×SSC, 5×Denhardt's solution, 1% SDS, 20 mM NaH$_2$PO4 (pH 6.8), 0.1 mg/ml salmon sperm DNA, 100 ug/ml yeast tRNA, 10 ug/ml poly-A mRNA and 7% dextran sulfate and was done for 14 hours at 65° C. Washing solution contained 2×SSC and 1% SDS and was done at room temperature and 50° C. for 15 minutes each, followed by a 2 hour wash at 80° C. with a solution containing 0.2×SSC and 1% SDS. Membranes were exposed on X-ray film (X-OMAT AR, Kodak®). The integrity of the RNA, as well as comparable amounts of RNA were tested by rehybridization with a GAPDH probe.

In situ Hybridization

Staged embryos ranging from 9 days to birth were obtained from timed breedings of CD-1 mice. Morning of the vaginal plugs was counted as 0.5 days post coitum (p.c.). Preparation of tissue and subsequent procedures for in situ hybridization were done as previously described (Marazzi and Buckley, 1993; Sassoon and Rosenthal, 1993). After hybridization and procedures, sections were dehydrated rapidly and processed for standard autoradiography using NTB-2 Kodak® emulsion and exposed for two weeks at 4 °C. Analysis was carried out using both light and dark field optics on a Leica® DA microscope. To avoid potential cross-hybridization with homologous RNAs, an antisense $^{35}$S-labeled RNA probe corresponding to the 3' UTR of Notch4 was used. Probes were used at a final concentration of 9×10$^4$ dpm/ml.

Results

Isolation and Analysis of Notch4 cDNA Clones

The int-3 mammary oncogene encodes a truncated protein that is highly homologous to the intracellular part of the Notch receptor proteins. The full length int-3 gene, referred to as Notch4, had been proposed to encode a novel member of the Notch protein family (Robbins et al., 1992). To prove this hypothesis, cDNAs containing the complete coding potential of the Notch4 gene have been cloned. Using primers derived from the published sequence of the int-3 oncogene, RT-PCR was used to isolate a 2.4 kb int-3 cDNA encoding the putative intracellular portion of the receptor. To obtain cDNA clones encompassing the full coding potential of the normal int-3 gene, cDNAs were isolated by 5' RACE and by screening a mouse lung cDNA library. A total of 37 overlapping cDNA clones were analyzed and sequenced to obtain a 6677 bp cDNA sequence. This sequence encodes one long open reading frame of 1964 amino acids, starting with an initiator methionine at nucleotide 347 and terminating with a stop codon at nucleotide 6239. The 6677 bp cDNA corresponds in size to that of Notch4 transcripts detected by Northern blot analysis; thus, this suggests that the cloned cDNA represents the full length Notch4 gene.

Several differences (insertions, deletions, and single nucleotide changes) were found between the nucleotide sequence of Notch4 reported here and the previously published int-3 nucleotide sequence (Robbins et al., 1992). These differences alter the reading frame in several locations within the intracellular domain and may be a result of differences in sequence analysis or possibly mutations found in the tumor derived int-3 transcript (Robbins et al., 1992) that are not found in the Notch4 gene. The nucleotide sequence of mouse Notch4 has been deposited with Genbank under the Accession number U43691.

Analysis of the Notch4 Deduced Amino Acid Sequence

Analysis of the deduced amino acid sequence of Notch4 reveals the presence of conserved domains shared by all Notch proteins (see FIG. 1). Notch4 contains EGF-like repeats, Notch/lin-12 repeats, a transmembrane domain, cdc10/ankyrin repeats and a putative PEST domain. The overall homology between Notch4 and other Notch proteins was determined using GCG (Bestfit, gap weight 3.0, length weight 0.1). The Notch4 protein is approximately 60% similar and 43% identical to other vertebrate Notch proteins, and 58% similar and 40% identical to Drosophila Notch. Lower homologies were found when compared to the *C. elegans* lin-12 and glp-1 proteins (49% similar and 29% identical).

Two hydrophobic regions in the Notch4 protein sequence were identified by hydropathy analysis (Kyte Doolittle algorithm, data not shown). An N-terminal region contains 19 hydrophobic residues that could function as a signal peptide sequence (FIG. 1) and a putative signal peptidase cleavage site was identified at residue 20. A second hydrophobic region from amino acid residues 1441 to 1465 is of sufficient length (25 amino acids) to behave as a membrane spanning domain and is immediately followed by five consecutive arginine residues that are consistent with a stop transfer signal (FIG. 1).

Figure 1B:
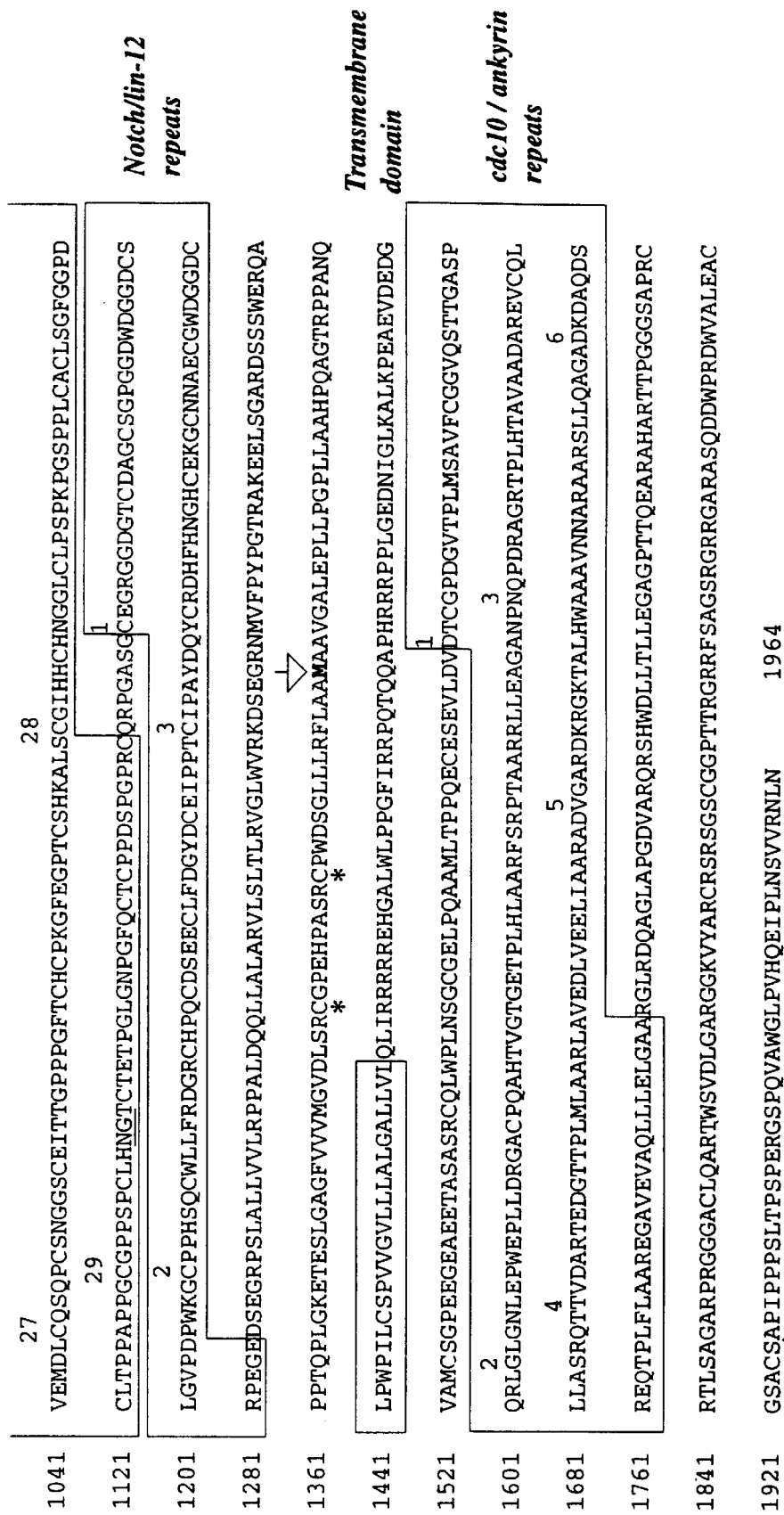
Figure 2:
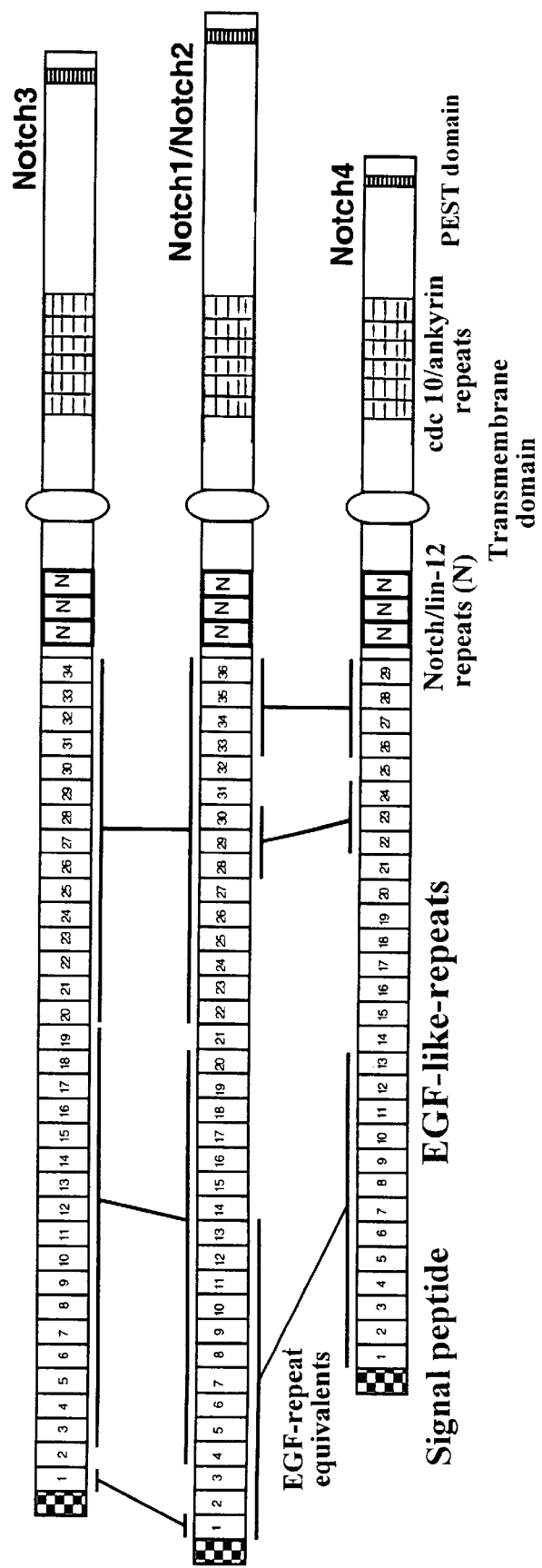
FIG. 2 Schematic structural comparison of the four murine Notch proteins. The EGF-like repeats are numbered according to their position in each different protein. Where equivalent EGF-like repeats can be identified, connecting lines are placed to compare the relationship between these repeats in different Notch proteins (see EGF-repeat equivalents). Notch4 contains seven EGF-like repeats, fewer than Notch1 and Notch2. One of the missing EGF-like repeats (#25) in Notch4 is derived from equivalent repeats #31 and #32 of Notch1/Notch2, creating a novel and hybrid EGF-like repeat. Eight of the EGF-like repeats of Notch4 (#14 to #21) have no identifiable equivalent repeats in Notch1/Notch2. The region of Notch4 from the end of the cec10/ankyrin repeats to the carboxy terminus is shorter when compared to Notch1, 2 and 3.

The extracellular domain of Notch4 contains 29 EGF-like repeats (FIGS. 1, 2), in contrast to the 36 EGF-like repeats found in murine Notch 1 (Franco Del Amo et al., 1993) and rat Notch 2 (Weinmaster et al., 1992), and to the 34 EGF-like repeats found in murine Notch 3 (Lardelli et al., 1994). EGF-like repeats are defined by a cysteine-rich consensus sequence and generally occur in analogous locations in two different Notch proteins. Since analogous repeats are more homologous to each other than to their neighboring EGF-like repeats, they have been referred to in Notch proteins as equivalent EGF-like repeats. The relationship between particular EGF-like repeats of other Notch proteins and those of the Notch4 protein was analyzed. FIG. 2 schematizes the relationship of EGF-equivalents between Notch4 and Notch1/Notch2. EGF-like repeats 1–13 of Notch4 are equivalent to EGF-like repeats 1–13 of Notch1/Notch2, EGF-like repeats 22–24 of Notch4 correspond to EGF-like repeats 28–30 of Notch1/Notch2, and EGF-like repeats 26–29 of Notch4 are equivalent to EGF-like repeats 33–36 of Notch1/Notch2. Comparison of Notch4 to other Notch proteins revealed no clear-cut identification of the seven particular equivalent EGF-like repeats that are absent in Notch4. The amino acid sequence of equivalent EGF-like repeats has diverged between different Notch homologues and orthologues (Maine et al., 1995), sometimes resulting in loss of a clear-cut equivalent repeat consensus. Six of the unassigned EGF-like repeats of Notch4 appear to be derived from EGF-like repeats 14–27 of Notch1 and Notch2 (FIG. 2). EGF-like repeat 25 of Notch4 may be a hybrid EGF-like repeats derived from parts of EGF-like repeats 31 and 32 of Notch1/Notch2 (FIG. 2). A discussion of the relationship between Notch3 and Notch1/Notch2 (shown in FIG. 2) is described in Lardelli et al., 1994.

EGF-like repeats 11 and 12 of Drosophila Notch have been shown to be necessary and sufficient for Notch to bind Delta and Serrate proteins in vitro (Rebay et al., 1991). These two equivalent EGF-like repeats are present in Notch4 (FIG. 2). The putative calcium-binding residues (Handford et al., 1991) in EGF-like repeat 11 are also conserved in Notch4 (FIG. 3). The residues between the first and second cysteine of EGF-like repeat 11 have been shown in Xenopus Notch to be important in ligand binding, and are divergent between Notch proteins (FIG. 3). In this region, Notch4 has additional residues and is unique when compared to other murine Notch proteins.

Notch4 also contains three Notch/lin-12 repeats which are approximately 53% identical to the Notch/lin-12 repeats found in other murine Notch proteins. Between the Notch/lin-12 repeats and the transmembrane domain of Notch4 are 2 cysteines a t positions 1388 and 1397 that are conserved among all Notch proteins and may promote receptor dimerization upon ligand binding (Greenwald and Seydoux, 1990).

The intracellular domain of Notch4 contains the 6 ankyrin/cdc10 repeats found in other Notch proteins. The ankyrin repeat domain of Notch4 is 48%, 52%, and 55% identical to the ankyrin repeat domains of Notch1, Notch2, and Notch3 respectively. In all Notch proteins the n umber of amino acids between the transmembrane domain and the ankyrin/cdc10 repeats is 110 residues, as it is in Notch4 (FIG. 1). Like other Notch proteins, Notch4 contains a C-terminal PEST domain, albeit of shorter length. In addition, Notch4 lacks a recognizable opa repeat (FIG. 1) such as that found in Drosophila Notch. The carboxy-terminal end of Notch proteins, beyond the ankyrin/cdc10 repeats, is the least conserved region among Notch proteins. Within this C-terminal region, Notch4 displays little homology to other Notch proteins and no significant homology to other known proteins. This C-terminal is also much shorter in Notch4 than in other Notch proteins, containing 177 residues, compared to 457 in Notch1, 437 in Notch2, and 329 in Notch3.

Expression Analysis of Notch4 in Adult Tissues

Several adult tissues were examined for the presence of Notch4 transcripts by Northern blot analysis. To minimize cross-hybridization with other mouse Notch transcripts, a riboprobe derived from the 3' UTR of Notch4 was used. In most tissues analyzed, a single hybridizing species of 6.7 kb was detected (FIG. 4), which roughly corresponds in size to the cloned Notch4 cDNA. The 6.7 kb transcript is most highly expressed in lung, at lower levels in heart and kidney, and at detectable levels in ovary and skeletal muscle. Very low levels of the 6.7 kb transcript were observed in several other adult tissues; including brain, intestine, liver, testis (FIG. 4) and spleen (data not shown). In adult testis, two abundant transcripts of 1.5 kb and 1.1 kb were observed. Thus, Notch4 expression varies widely in adult tissues. Other than in testis, transcript size variation in different tissues was not detected.

Analysis of Testis-specific Truncated Notch4 Transcripts

To determine the cell lineage specificity of Notch4 expression in the murine testis, RNA was analyzed in the germ cell deficient mouse testis (FIG. 5). Mice that carry two mutations at the white-spotting locus (W/W–v) are devoid of germ cells, but have the normal complement of somatic cell types, including Leydig, Sertoli, and peritubular myoid cells (Mintz and Russell, 1957). Heterozygous litter mates (W/+) have normal somatic and germ cell complements. Northern blot analysis of total RNA from germ cell-deficient testes (W/W–v) and testes with normal germ cells (W/+ and adult (+/+)) was done using a riboprobe derived from the 3' UTR (probe D in FIG. 5C). Transcripts of 1.5 kb and 1.1 kb were detected in RNA from the testes of adult wild-type mice and W/+ mice (FIG. 5A). However, neither transcript was detected in RNA from homozygous mutant testes, suggesting that these transcripts were likely to be specific to the germinal compartment.

Since spermatogenic differentiation undergoes a characteristic temporal progression, one can use mice testes at specific days of postnatal development to enrich for or eliminate particular germ cell types. Testes from day 7 of postnatal development (day 7 p.n.) mice contain mitotic spermatogonia while testes from day 17 p.n. mice have entered meiosis and have progressed to spermatocytes (Nebel et al., 1961). Both day 7 p.n. and day 17 p.n. testes lack post-meiotic spermatids. Total RNA from immature and adult testes was analyzed by Northern blot hybridization to determine stage-specific expression of Notch4 transcripts during male germ cell development. Both Notch4 transcripts of 1.5 kb and 1.1 kb are absent in day 7 p.n. and day 17 p.n. testis, but are present in adult testis (FIG. 5A). These results indicate that the expression of the 1.5 kb and 1.1 kb Notch4 transcripts are restricted to post-meiotic germ cells.

To determine the nature of the short Notch4 transcripts in adult mouse testis, Northern blot analysis was done using riboprobes derived from different regions of the Notch4 coding sequence, as well as from 5' and 3' UTR (FIG. 5B). A riboprobe derived from the 5' UTR (probe A in FIG. 5C) failed to hybridize to either the 1.5 kb or the 1.1 kb transcripts (FIG. 5B); whereas this probe did hybridize to the 6.7 kb transcript found in lung RNA (FIG. 5B). However, riboprobes derived from the 3' UTR (probe D in FIG. 5C) or from cDNA encoding part of the intracellular domain of Notch4 (probe C in FIG. 5C) hybridize to the testis transcripts (FIG. 5A and data not shown). Probes derived from the coding sequence of the extracellular domain of Notch4 (probe B in FIG. 5C) did not hybridize to the testes transcripts (data not shown). To characterize the transcripts expressed in the adult mouse testis, a cDNA library prepared from adult mouse testes RNA was screened using probe C of FIG. 5C. All the clones analyzed encoded the most C-terminal coding sequence and the 3' untranslated region of Notch4. Two independent clones of distinct size contained novel 5' sequences unrelated to that found in the full-length Notch4 cDNA (schematized in FIG. 5C-Notch4 testis transcripts). Based upon the Northern blot analysis described above and the sequence of the cloned testis cDNAs, it is suggested here that Notch4 transcripts are either derived from an alternate intronic promoter that is active in post-meiotic germ cells or they may be driven by the same promoter as the 6.7 kb transcript and consist of spliced products derived from a 5' untranslated region upstream of what has currently been identified. The predicted amino acid sequence of the testis Notch4 transcripts with novel 5' sequence does not contain a methionine that could function as a translation initiator; therefore, these transcripts are unlikely to encode for protein products. The testis transcripts may thus represent aberrant transcriptional events in post-meiotic germ cells, as has been described previously (Davies and Willison, 1993).

Expression Analysis of Notch4 During Development

Figure 6A:
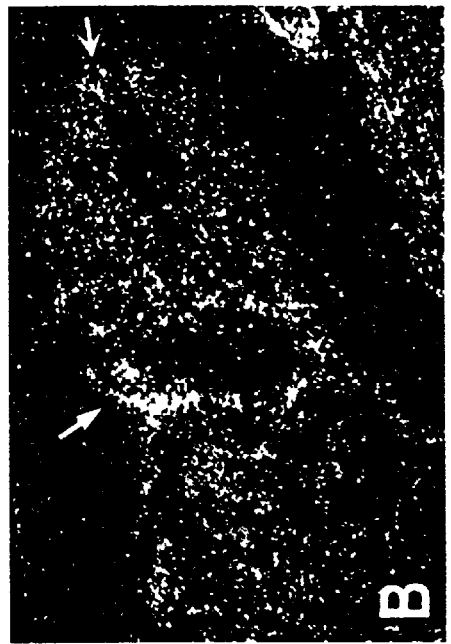
Figure 6B:
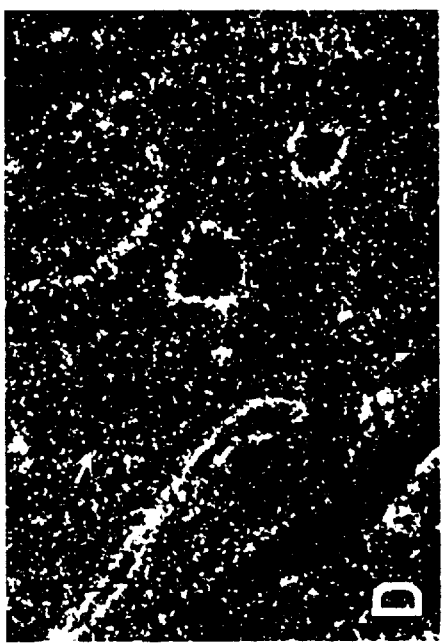
Figure 6C:
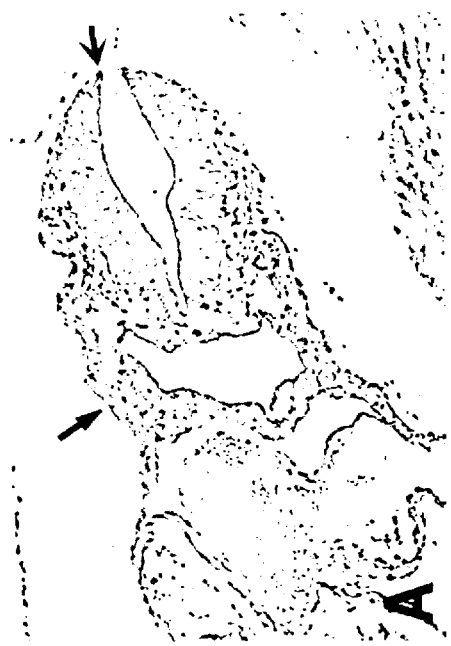
Figure 6D:
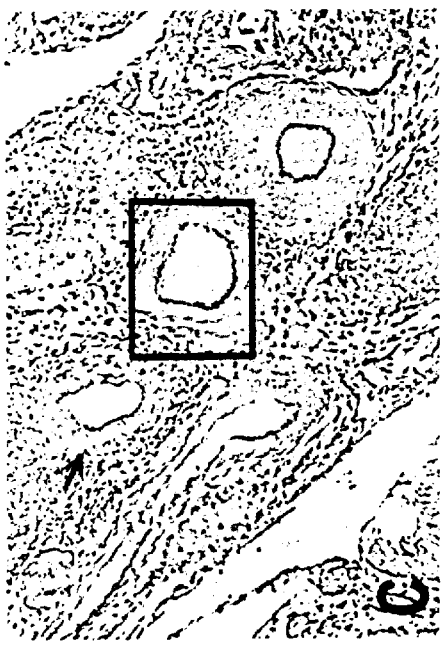

A 6.7 kb Notch4 transcript was detected by Northern hybridization in RNA isolated from day 12.5 p.c. mouse embryos (data not shown and Sarkar et al., 1994). To determine the spatial and temporal pattern of Notch4 transcript accumulation during development, mouse embryo tissue sections from 9.0 days p.c. to birth was examined using in situ hybridization. Throughout embryonic development, as well as in postnatal tissues (data not shown), Notch4 is highly expressed in endothelial cells. Intense labeling for Notch4 is observed in embryonic blood vessels at 9.0 days p.c. (FIG. 6A, B). As shown in FIG. 6 (panel C and D) strong labeling is observed over the dorsal aorta, the aortic tract, and the pulmonary artery in a 13.5 days p.c. embryo, while no labeling is detected in the epithelial cells lining the gut (red arrow). At higher magnification, it is noted that labeling is restricted to the endothelial cells lining the embryonic vessels (FIG. 6 D, E) and no labeling is detected in the red blood cells in the vessel. A weak and transient signal is also detectable in the developing nervous system from 9.0 days p.c. embryos. As shown in FIG. 6 (panel A and B), a light diffuse labeling is detected in the developing nervous system, and a more distinct signal is observed at the tip of the neural folds. Notch4 transcripts in the nervous system are still detectable at 11.5 days p.c., but by 13.5 days p.c. no labeling for Notch4 is detectable in the nervous system (data not shown). In situ hybridization on adult lung and kidney sections was performed to determine the cell types responsible for Notch4 expression (data not shown) and Notch4 transcripts were solely found in the endothelial compartment of these tissues. The endothelial specific expression likely underlies the abundance of Notch4 transcripts found by Northern blot analysis of highly vascularized adult tissues (lung, heart, and kidney in FIG. 4).

Discussion

It is reported here the identification of a novel mouse gene that exhibits structural homology with the vertebrate Notch protein family. This gene has been named Notch4, as it is the fourth murine Notch gene identified. Notch4 contains all the conserved domains characteristic of Notch proteins (FIGS. 1 and 2). However, Notch4 contains only 29 EGF-like repeats within its extracellular domain as compared to the 36 repeats found in Notch1 and Notch2. In addition, the C-terminal tail of Notch4, beyond the ankyrin/cdc10 repeats, is shorter and unique when compared to all other Notch proteins, however, little is known of the function of this region in Notch proteins. Notch4 also contains a distinct EGF-like repeat 11 which has been proposed to be crucial for ligand binding. Structural variation in this repeat, and differences in the number of EGF-like repeats between murine Notch proteins, may be important for ligand specificity among the different possible Notch ligands. It must be noted that Notch/lin-12 proteins of varying structure have been demonstrated to be functionally interchangeable; *C. elegans* glp-1 can fully substitute for lin-12 (Fitzgerald et al., 1993) for instance. Therefore, Notch4 may be functionally interchangeable with other murine Notch proteins despite structural differences between these Notch proteins.

Notch4 is distinct from other Notch family proteins based on its expression pattern during embryonic development and in the adult mouse. In situ hybridization demonstrates endothelial-specific embryonic expression of Notch4. This endothelial-specific expression of Notch4 remains in the adult mouse. A weak and transient labeling is seen in the neural tube between day 9 p.c. and 11.5 p.c., with a more intense labeling at the tips of neural folds. This region of the neural tube is a highly plastic area where cells will probably participate in the fusion process of the neural tube and/or migrate as neural crest. The Notch4 expression pattern is in sharp contrast to the expression patterns of Notch1, 2, and 3. These Notch genes are expressed in a variety of different embryonic tissues such as the developing brain and spinal cord, presomitic and somitic mesoderm, and a variety of epithelial cells and mesenchymal derived tissues (Weinmaster et al., 1991; Williams et al., 1995). Notch1 is the only other Notch gene reported to be expressed in endothelial cells (Reaume et al., 1992). Endothelial expression has not been reported for Jagged and Dll-1, two putative mammalian Notch ligands (Bettenhausen et al., 1995; Lindsell et al., 1995) Expression of Notch1 and 4 in endothelial cells might reflect either redundancy of function or distinct biological functions in endothelial development.

Since Notch proteins have been implicated in binary cell fate specification regulating how equivalent cells can give rise to cells with different fates, a putative biological function of Notch4 might be to govern the cell fate decisions during endothelial growth and development. In amniotes, endothelial and hematopoietic cells appear synchronously in the blood islands. In zebra fish, lineage data have shown that individual cells of the early blastula can give rise to both endothelial and blood cells, suggesting a common embryonic precursor which has been referred to as the "hemangioblast." The occurrence of binary cell fate decision events in the hemangioblast is supported by analysis of the endothelial and/or hematopoietic cell lineages. Cloche, bloodless, and spadetail are mutants isolated in zebra fish that display phenotypes defective in either the hematopoietic development or both hematopoietic and endothelial development (Stainier et al., 1995). In the mouse, the Flk-1 and the Flt-1 genes encode receptor tyrosine kinases that are expressed in embryonic endothelium (Shalaby et al., 1995, Fong et al., 1995). Null mutants for the Flk-1 gene are defective in endothelial and blood cell development (Shalaby et al., 1995), whereas null mutants for the Flt-1 gene display only hematopoietic cell development defects (Fong et al., 1995). Mutational analysis of the Notch4 gene in whole animals would help to define the role of Notch4 in endothelial cell growth and development.

Alterations in stem cell fate decisions as a result of activated Notch proteins have been proposed to contribute to mitogenic growth of tumor cells. Blocked cell differentiation of fated daughter cells by activated Notch proteins may lead to an increase in the number of cells undergoing cell division or a prolonged life of the cell. In these cells, the probability of secondary oncogenic mutations that contribute to neoplastic transformation would be enhanced. Although little is known about the nature of stem cells in the mammary epithelium, Notch4 might regulate the fate decisions of mammary epithelial cells. This hypothetical model may explain the phenotype that is observed in int-3 transgenic mice, which display blocked development of the mammary gland and develop mammary carcinomas at high frequency.

The signal transduction pathways by which Notch proteins function are becoming understood through genetic studies in Drosophila. Deltex and Suppresser of Hairless (Su(H)) have been demonstrated to bind to the cdc10 repeats of the intracellular domain of Drosophila Notch (Diederich et al., 1994; Fortini and Artavanis-Tsakonas, 1994; Matsuno et al., 1995). More recently the mammalian Su(H) orthologue RBP-Jk, a transcription factor, has been shown to bind to the intracellular domain of Notch 1 (Jarriault et al., 1995). Since Notch4 contains the canonical ankyrin/cdc10 repeats, RBP-Jk or RBP-Jk homologues and mammalian Deltex homologues may interact with the cdc10/ankyrin repeats of Notch4. It has been proposed that upon activation of the Notch receptors, Su(H) or RBP-Jk are activated and translocate to the nucleus where they may regulate transcription of target genes (Goodbourn, 1995). In fact, activated Notch proteins encoding the intracellular domain have been reported to localize to the nucleus (Kopan et al., 1994; Struhl et al., 1993) suggesting a nuclear function for this domain. It was found that an epitope-tagged version of the int-3 oncoprotein is also localized to the nucleus when expressed in cultured 293T cells, as determined by immunofluorescence (unpublished data). This finding may indicate that int-3 can bind to cytoplasmic proteins that are then translocated to the nucleus.

It is shown here that the int-3 gene encodes a truncated Notch4 protein with the extracellular domain deleted (EGF-like repeats and Notch/lin-12 repeats), providing the first comparison of a naturally-activated murine Notch protein and its normal counterpart. In MMTV-induced mouse mammary tumors with an activated Notch4, as described in Robbins et al. (1992), the oncogenic affects are likely the result of both over expression or ectopic expression of Notch4 mRNA as well as functional activation of the Notch4 protein. A structural comparison of the mutant int-3 protein to the normal Notch4 protein is reminiscent of the structural alterations reported to activate the effector function of Drosophila Notch and C. elegans lin-12 proteins (Greenwald, 1994) or oncogenic activation of TAN-1. Thus, loss of the extracellular domain likely leads loss of the regulatory controls provided by the ligand binding domain believed to reside in the EGF-like repeats of Notch4.

REFERENCES CORRESPONDING TO FIRST SERIES OF EXPERIMENTS

Artavanis-Tsakonas, S. and Simpson, P. (1991). Choosing a cell fate: a view from the Notch locus. [Review]. *Trends in Genetics* 7, 403–408.

Artavanis-Tsakonas, S., Matsuno, K. and Fortini, M. E. (1995). Notch signaling. [Review]. *Science* 268, 225–232.

Bettenhausen, B., Hrabe de Angelis, M., Simon, D., Guenet, J.-L. and Gossler, A. (1995). Transient and restricted expression during mouse embryogenesis of Dll, a murine gene closely related to *Drosophila Delta*. *Development* 121, 2407–2418.

Coffman, C. R., Skoglund, P., Harris, W. A. and Kintner, C. R. (1993). Expression of an extracellular deletion of Xotch diverts cell fate in Xenopus Embryos. *Cell* 73, 659–671.

Conlon, R. A., Reaume, A. G. and Reascend, J. (1995). Notch1 is required for the coordinate segmentation of somites. *Development* 121, 1533–1545.

Davies, O. P. and Willison, K. R. (1993). Molecular mechanisms of differentiation in mammalian spermatogenesis. *Developmental Biology* 3, 179–188.

Diederich, R. J., Matsuno, K., Hing, H. and Artavanis-Tsakonas, S. (1994). Cytosolic interaction between deltex and Notch ankyrin repeats implicates deltex in the Notch signaling pathway. *Development* 120, 473–481.

Ellisen, L. W., Bird, J., West, D. C., Soreng, A. L., Reynolds, T. C., Smith, S. D. and Sklar, J. (1991). TAN-1, the human homolog of the Drosophila notch gene, is broken by chromosomal translocations in T lymphoblastic neoplasms. *Cell* 66, 649–661.

Fitzgerald, K., Wilkinson, H. A. and Greenwald, I. (1993). glp-1 can substitute for lin-12 in specifying cell fate decisions in Caenorhabditis elegans. *Development* 119, 1019–1027.

Fleming, R. J., Scottgale, T. N., Diederich, R. J. and Artavanis-Tsakonas, S. (1990). The gene Serrate encodes a putative EGF-like transmembrane protein essential for proper ectodermal development in Drosophila melanogaster. *Genes & Development* 4, 2188–2201.

Fong, G., Reascend, J., Gertsenstein, M. and Breitman, M. L. (1995). Role of the Flt-1 receptor tyrosine kinase in regulating the assembly of vascular endothelium. *Nature* 376, 66–70.

Fortini, M. E., Rebay, I., Caron, L. A. and Artavanis-Tsakonas, S. (1993). An activated Notch receptor blocks cell-fate commitment in the developing Drosophila eye. *Nature* 365, 555–557.

Fortini, M. E. and Artavanis-Tsakonas, S. (1994). The suppresser of hairless protein participates in notch receptor signaling. *Cell* 79, 273–282.

Franco Del Amo, F., Gendron-Maguire, M., Swiatek, P. J., Jenkins, N. A., Copeland, N. G. and Gridley, T. (1993). Cloning, analysis, and chromosomal localization of Notch-1, a Mouse homolog of Drosophila Notch. *Genomics* 15, 259–264.

Gallahan, D. and Callahan, R. (1987). Mammary tumorigenesis in feral mice: identification of a new int locus in mouse mammary tumor virus (Czech II)-induced mammary tumors. *J. Virol.* 61, 66–74.

Goodbourn, S. (1995) Notch takes a short cut. *Nature* 377, 288–289.

Greenwald, I. (1985). lin-12, a nematode homeotic gene, is homologues to a set of mammalian proteins that includes epidermal growth factor. *Cell* 43, 583–590.

Greenwald, I. and Seydoux, G. (1990). Analysis of gain-of-function mutations of the lin-12 gene of *Caenorhabditis elegans*. *Nature* 346, 197–199.

Greenwald, I. and Rubin, G. M. (1992). Making a difference: the role of cell-cell interactions in establishing separate identities for equivalent cells. [Review]. *Cell* 68, 271–281.

Greenwald, I. (1994). Structure/function studies of lin-12/Notch proteins. [Review]. *Current Opinion in Genetics & Development* 4, 556–562.

Handford, P. A., Mayhew, M., Baron, M., Winship, P. R., Campbell, I. D. and Brownlee, G. G. (1991). Key residues involved in calcium-binding motifs in EGF-like repeats. *Nature* 351, 164–167.

Henderson, S. T., Gao, D., Lambie, E. J. and Kimble, J. (1994). lag-2 may encode a signaling ligand for the GLP-1 and LIN-12 receptors of *C. elegans*. *Development* 120, 2913–2924.

Jarriault, S., Brou, C., Logeat, F., Schroeter, E. H., Kopan, R. and Israel, A. (1995). Signaling downstream of activated mammalian Notch. *Nature* 377, 355–358.

Jhappan, C., Gallahan, D., Stahle, C., Chu, E., Smith, G. H., Merline, G. and Callahan, R. (1992). Expression of an activated Notch-related int-3 transgene interferes with cell differentiation and induces neoplastic transformation in mammary and salivary glands. *Genes Devel.* 6, 345–355.

Kopan, R., Nye, J. S. and Weintraub, H. (1994). The intracellular domain of mouse Notch: a constitutively activated repressor of myogenesis directed at the basic helix-loop-helix region of MyoD. *Development* 120, 2385–2396.

Lardelli, M. and Lendahl, U. (1993). Motch A and Motch B-two mouse Notch homologues coexpressed in a wide variety of tissues. *Exp. Cell Res.* 204, 364–372.

Lardelli, M., Dahlstrand, J. and Lendahl, U. (1994). The novel Notch homologue mouse Notch3 lacks specific epidermal growth factor-repeats and is expressed in proliferating neuroepithelium. *Mechanism of Development* 46, 123–136.

Lindsell, C. E., Shawber, C. J., Boulter, J. and Weinmaster, G. (1995). Jagged: a mammalian ligand that activates Notch1. *Cell* 80, 909–917.

Maine, E. M., Lissemore, J. L. and Starmer, W. T. (1995). A phylogenetic analysis of vertebrate and invertebrate Notch-related genes. *Molecular Phylogenetics and Evolution* 4, 139–149.

Marazzi, G. and Buckley, K. M. (1993). Accumulation of mRNAs encoding synaptic vesicle-specific proteins precedes neurite extension during early neuronal development. *Developmental Dynamics* 197, 115–124.

Matsuno, K., Diederich, R. J., Go, M. J., Blaumeueller, C. M. and Artavanis-Tsakonas, S. (1995). Deltex acts as a positive regulator of Notch signaling through interactions with the Notch ankyrin repeats. *Development* 121, 2633–2644.

Mello, C. C., Draper, B. W. and Priess, J. R. (1994). The maternal genes apx-1 and glp-1 and establishment of dorsal-ventral polarity in the early *C. elegans* embryo. *Cell* 77, 95–106.

Michaely, P. and Bennett, V. (1992). The ANK repeat: a ubiquitous motif involved in macromolecular recognition. *Trends Cell Biol.* 2, 127–129.

Mintz, B. and Russell, E. S. (1957). Gene-induced embryological modifications of primordial germ cell in the mouse. *J. Exp. Zool.* 134, 207–230.

Nebel, B. R., Amarose, A. P. and Hackett, E. M. (1961). Calendar of gametogenic development in the prepuberal male mouse. *Science* 134, 832–833.

Reaume, A. G., Conlon, R. A., Zirngibl, R., Yamaguchi, T. P. and Reascend, J. (1992). Expression analysis of a Notch homologue in the mouse embryo. *J. Dev. Biol.* 154, 377–387.

Rebay, I., Fleming, R. J., Fehon, R. G., Cherbas, L., Cherbas, P. and Artavanis-Tsakonas, S. (1991). Specific EGF repeats of Notch mediate interactions with Delta and Serrate: implications for Notch as a multi-functional receptor. *Cell* 67, 687–699.

Rebay, I., Fehon, R. G. and Artavanis-Tsakonas, S. (1993). Specific truncations of Drosophila Notch define dominant activated and dominant negative forms of the receptor. *Cell* 74, 319–329.

Robbins, J., Blondel, B. J., Gallahan, D. and Callahan, R. (1992). Mouse mammary tumor gene int-3, a member of the notch gene family transforms mammary epithelial cells. *J. Virol.* 66, 2594–2599.

Rogers, S., Wells, R. and Rechsteiner, M. (1986). Amino acid sequences common to rapidly degrade proteins: The PEST hypothesis. *Science* 234, 364–368.

Sarkar, N. H., Haga, S., Lehner, A. F., Zhao, W., Imai, S. and Moriwaki, K. (1994). Insertional mutation of int protooncogenes in the mammary tumors of a new strain of mice derived from the wild in China: normal- and tumor-tissue-specific expression of int-3 transcripts. *Virology* 203, 52–62.

Sassoon, D. and Rosenthal, N. (1993). Detection of messenger RNA by in situ hybridization. *Methods Enzymol*; Wassereman, P. M. and DePamphilis, M. L. (eds) V225, 384–404.

Shalaby, F., Reascend, J., Yamaguchi, T. P., Gertsenstein, M., Wu, X., Breitman, M. L. and Schuh, A. C. (1995). Failure of blood-island formation and vasculogenesis in FLK-1-deficient mice. *Nature* 376, 62–66.

Smith, G. H., Gallahan, D., Diella, F., Jhappan, C., Merlino, G. and Callahan, R. (1995). Constitutive expression of a truncated INT-3 gene in mouse mammary epithelium impairs differentiation and functional development. *Cell Growth & Differentiation* 6, 563–577.

Stainier, D. Y. R., Weinstein, B. W., Detrich, H. W., Zon, L. I. and Fishman, M. C. (1995). cloche, an early acting zebra fish gene, is required by both the endothelial and hematopoietic lineages. *Development* 121, 3141–3150.

Stifani, S., Blaumueller, C. M., Redhead, N. J., Hill, R. E. and Artavanis-Tsakonas, S. (1992). Human homologs of a Drosophila Enhancer of split gene product define a novel family of nuclear proteins [published erratum appears in Nat Genet 1992 Dec;2(4):343]. *Nature Genetics* 2, 119–127.

Struhl, G., Fitzgerald, K. and Greenwald, I. (1993). Intrinsic activity of the Lin-12 and Notch intracellular domains in vivo. *Cell* 74, 331–345.

Sugaya, K., Fukagawa, T., Matsumoto, K., Mita, K., Takahashi, E., Ando, A., Inoko, H. and Ikemura, T. (1994). Three genes in the human MHC class III region near the junction with the class II: gene for receptor of advanced glycosylation end products, PBX2 homeobox gene and a notch homolog, human counterpart of mouse mammary tumor gene int-3. *Genomics* 23, 408–419.

Swiatek, P. J., Lindsell, C. E., Franco del Amo, F., Weinmaster, G. and Gridley, T. (1994). Notch 1 is essential for postimplantation development in mice. *Genes & Development* 8, 707–719.

Tax, F. E., Yeargers, J. J. and Thomas, J. H. (1994). Sequence of C. elegans lag-2 reveals a cell-signaling domain shared with Delta and Serrate of Drosophila. *Nature* 368, 150–154.

Vassin, H., Bremer, K. A., Knust, E. and Campos-Ortega, J. A. (1987). The neurogenic gene Delta of Drosophila melanogaster is expressed in neurogenic territories and encodes for a putative transmembrane protein with EGF-like repeats. *EMBO J.* 6, 3431–3440.

Weinmaster, G., Roberts, V. J. and Lemke, G. A. (1991). A homolog of Drosophila Notch expressed during mammalian development. *Development* 113, 199–205.

Weinmaster, G., Roberts, V. J. and Lemke, G. (1992). Notch 2: a second mammalian Notch gene. *Development* 116, 931–941.

Williams, R., Lendahl, U. and Lardelli, M. (1995). Complementary and combinatorial patterns of Notch gene family expression during early mouse development. *Mechanisms of Development* 53, 357–368.

Yochem, J. and Greenwald, I. (1989). glp-1 and lin-12, genes implicated in distinct cell-cell interactions in *C. elegans,* encode similar transmembrane proteins. *Cell* 58, 553–563.

Second Series of Experiments

Material and Methods

Reagents

Recombinant human basic fibroblast growth factor (bFGF) was kindly provided by Dr. Anthony Belve (Columbia University, New York). Rat tail collagen solution was obtained from Upstate Biotechnology Inc. (Lake Placid, N.Y.). Anti-HA monoclonal antibody (12CA5) was obtained from Berkeley Antibody Co. (Richmond, Calif.) and horseradish peroxidase-conjugated sheep anti-mouse immunoglobulin G from Amersham (Arlington Heights, Ill.). All restriction and DNA modifying enzymes were purchased from New England Biolab Inc. (Beverly, Mass.).

The murine int-3 cDNA corresponds to a truncated Notch4 cDNA as described previously. The int-3 nucleotide sequence corresponds to nucleotide 4551 to nucleotide 6244 of Notch4. An oligonucleotide sequence encoding the haemagglutinin (HA) antigenic determinant was appended to the 3' end of the int-3 and Notch4 cDNA's. These eighteen codons specified the amino acid sequence SMA YPYDVPDYASLGPGP (SEQ ID NO:9), including the nine amino acid-long HA epitope, as underlined. HA-tagged int-3 and Notch4 cDNAs were created by subcloning each cDNA into Bluescript KS (Stratagene®) that contained the coding region of the HA epitope situated downstream of the newly inserted cDNA, separated from it by polylinker sequence. These two sequences were made co-linear by the "loop-out" mutagenesis procedure using oligonucleotides designed to eliminate the stop codon and non-coding 3' sequence of the int-3 and Notch4 cDNAs and flanking polylinker sequence. The sequence of the oligonucleotides used to loop out int-3 and Notch4 specific sequences are CGG TTG TAA GAA ATC TGA ACTCCA TGG CCT ACC CAT ATG (SEQ ID NO:10). The 5' end of each oligonucleotide is complimentary to the C-terminus of int-3 or Notch4 cDNA and their 3' ends anneal to the beginning of the HA epitope-encoding sequence (underlined in oligonucleotide). Mutagenesis was accomplished using the Muta-Gene phagemid in vitro mutagenesis kit (Bio Rad, Richmond, Calif.). The presence of each fusion was confirmed by DNA sequencing. The JaggedHA cDNA, HA-tagged at the carboxy terminus, was obtained from Dr. Gerry Weinmaster (UCSF, California).

Cell Cultures

Rat Brain Microvessel endothelial cells (RBE4) cells were obtained from Dr. Francoise Roux (INSERM U26, Hopital F. Widal, Paris) and were routinely plated on collagen coated dishes and maintained in Alpha MEM/Ham's F10 (1:1) supplemented with 2 mM glutamine, 10% fetal calf serum, 1ng/ml basic fibroblast growth factor (bFGF), and penicilline/streptomycin in humidified 5% $CO_2$/95% air at 37 C. Medium was changed twice a week, and cells were passaged at a split ratio of 1:4.

Cell Lines

HA-tagged cDNAs (int-3HA, JaggedHA, and Notch4HA) were inserted into the retroviral vector pLHTCX wherein hygromycin-resistance/thymidine kinase fusion gene phosphotransferase gene expression is controlled by the murine leukemia virus (MLV) long terminal repeat (LTR), and cDNA transcription is controlled by an internal cytomegalovirus (CMV) enhancer/promoter. Distinct populations of RBE4 cells, each expressing an HA-tagged int3 or Jagged cDNA, were prepared by retroviral infection. Recombinant retroviruses were generated by transiently transfecting pLHTCX constructs into the BOSC 23 packaging cell line by calcium phosphate co-precipitation. Retroviral infection of RBE4 cells was accomplished by culturing these cells in the presence of viral supernatants obtained from the transfected packaging cells two day post-transfection. Infections were carried out in the presence of 4 µg/ml polybrene for 12 hours after which the medium was replaced to regular medium. One day post-infection the culture medium was replaced to regular medium containing 100 µg/ml hygromycin B (Sigma Chemical Co.). Colonies appeared 5 days later and were pooled into medium containing 100 µg/ml hygromycin B. These resultant populations, each comprised of at least 50 clones, were used in cellular and biochemical assays described below. Distinct populations of RBE4 cells expressing an HA-tagged Notch4 cDNA were prepared by calcium phosphate transfection directly into the RBE4 cells. Selection and pooling of resistant colonies was done as described above.

Immunoblot Analysis

HA epitope tagged int-3, Jagged and Notch4 proteins from lysates of RBE4 cell populations were analyzed by immunoblotting. To maximize protein expression, RBE4 cells were treated with 2 mM sodium butyrate for 16 hours prior to lysis. Cells were washed twice with cold PBS and, subsequently, removed from the dish in 1.5 ml PBS using a rubber policeman. Cells were pelleted by centrifugation at 2,000×g at 4° C. for 5 min. and lysed in 90 µl TENT buffer (20 mM Tris, pH 8.0, 2 mM EDTA, 150 mM NaCl, 1% Triton-×100) containing 1 mM phenylmethylsulfonyl fluoride, 10 mg/ml aprotinin, 2 mg/ml leupeptin, 1 mg/ml pepstatin, at 4° C. for 30 min. Lysates were clarified by centrifugation at 10,000×g at 4° C. for 10 min., and protein contents were determined using the BioRad Protein determination kit. Lysates containing 20 µg protein were electrophoresed in 9% SDS-polyacrylamide gels. Proteins were transferred from gels onto nitrocellulose filters by electroblotting, and subsequently, blocked overnight at 4° C. in TBST(10 mM Tris, pH 8.0, 150 mM NaCl, 0.2% Tween-20) containing 1% bovine serum albumin (fraction V). Blots were then incubated in anti-HA monoclonal antibody (12CA5) diluted 1:200 in TBST at room temperature. After four hours, the primary antibody was removed by washing three times for 5 min. each in TBST at temperatures identical to the primary antibody incubation. Blots were exposed to a 1:16,000 dilution of horseradish peroxidase-conjugated sheep anti-mouse immunoglobulin G. Excess secondary antibody was removed in the same manner as the primary antibody. Blots were then incubated 1–2 min. in enhanced chemiluminescence detection reagents (Amersham Inc, Arlington Heights, Ill.) and exposed to X-ray film (Fujifilm, Fuji Photo Film Co., LTD., Tokyo)

Angiogenesis Assay

RBE4 cell lines were harvested using trypsin-EDTA, centrifuged, and plated on collagen coated dishes at equal cell densities (50% confluence at plating) with or without bFGF (5 ng/ml) RBE4 cell culture was done in the absence of 2 mM Sodium Butyrate. After 3 to 5 days, cell cultures were photographed with a Nikon ELWD 0.3 phase contrast microscope on Kodak T-Max film (100×magnification).

Results

Generation of RBE4 Cell Lines

RBE4 cell lines programmed to express the int-3, Jagged, and Notch4 proteins were generated using either the retroviral vector pLHTCX which drives expression from the CMV promoter, or by direct transfection of the cDNA in target RBE4 cells. In order to detect the int-3, and Notch4 proteins, the int-3, Jagged and Notch4 cDNA were fused at the carboxy termini to the haemagglutinin-epitope (HA), allowing us to detect int-3, Jagged and Notch4 proteins in immunoblot analysis using the anti-HA monoclonal antibody. As expected, all 3 recombinant proteins migrate with an expected molecular weight (70 kd for int-3HA, 150 kd for JaggedHA, and 220 kd for Notch4HA). Moderate levels of recombinant protein expression is detected in the RBE4 cell lines generated. This expression level can be significantly increased by treating all RBE4 cell line with Sodium Butyrate (2 mM) which enhances transcription of the CMV promoter. Addition of Sodium Butyrate to the RBE4 angiogenic assay did not alter or enhance the observed phenotype described below, and therefor Sodium Butyrate was omitted from all RBE4 cell biological assays. As a control, RBE4 cells were generated that were programmed to express LacZ.

Morphological Heterogeneity of RBE4 Cell Lines

RBE4 cells programmed to express LacZ or Notch4HA have an identical cell morphology when compared to wild type RBE4 cells (FIG. 8). When RBE4 cells programmed to express either LacZ or Notch4 are grown in high concentrations of bFGF, they exhibit a spindle shape morphology and form modest sprouting and capillaries, a phenotype that is indistinguishable with wild type RBE4 cells grown under identical conditions (data not shown).

RBE4 cells programmed to express JaggedHA display a modest spindle shape morphology when grown in the absence of bFGF (see FIG. 8). RBE4 cells programmed to express int-3HA display a striking spindle shape morphology when grown in the absence of bFGF (FIG. 8). Thus, RBE4 cells programmed to express either JaggedHA or int-3 HA exhibit a morphology in the absence of bFGF that is similar (although more extensive) to the bFGF induced morphological change of wild type RBE4 cells, or RBE4 cells programmed to express either LacZ or Notch4. When RBE4 cells programmed to express Jagged or int-3 are grown in the presence of high concentrations of bFGF, the spindle shape morphology of the cells becomes even more accentuated (data not shown).

Induction of Angiogenesis by Activated Notch4 and Jagged

RBE4 cells programmed to express LacZ or Notch4HA growth arrest at confluency and in the absence of bFGF do not develop any three dimensional structures (FIG. 8). This phenotype is identical to confluent wild type RBE4 cells grown in the absence of bFGF. When confluent RBE4 cells programmed to express either LacZ or Notch4 are grown in high concentrations of bFGF (5 ng/ml), they form modest sprouts and capillaries, a phenotype that is indistinguishable with wild type RBE4 cells grown under identical conditions (data not shown). RBE4 cells programmed to express JaggedHA develop sprouts and three-dimensional capillary-like structures when grown in the absence of bFGF (see FIG. 8). The capillary structures formed by RBE4 cells programmed to express Jagged either float (although originating from a mount formed on the tissue culture plate) in the cell culture medium or are attached to the tissue culture plate. There is a bias in the photographs depicted in FIG. 8, in favor of taking photographs of these structures that are attached to the tissue culture, plate since these are easier to focus on then on the floating capillaries that are difficult to visualize in one plain. RBE4 cells programmed to express int-3HA develop similar three-dimensional structures when grown in the absence of bFGF (FIG. 8), however the extent is even greater then when compared to RBE4 cells programmed to express Jagged. Thus, RBE4 cells programmed to express either JaggedHA or int-3 HA exhibit a morphology in the absence of bFGF that is similar (although more extensive) to the bFGF induced morphological change of wild type RBE4 cells, or RBE4 cells programmed to express either LacZ or Notch4. When RBE4 cells programmed to express Jagged or int-3 are grown in the presence of high concentrations of bFGF, the development of the three dimensional capillary structures becomes even more accentuated (data not shown).

Discussion

Several conclusions of the above described experiments can be made.

This data demonstrates that int-3 (an activated Notch4) and Jagged contain a biological activity on RBE4 cells that is similar to the known angiogenic agent bFGF, suggesting that this activity is an angiogenic activity.

This data suggests that RBE4 cells express an endogenous Notch, since RBE4 cells that are programmed to express Jagged (a mammalian Notch ligand) have a similar phenotype when compared to RBE4 cells that express a constitutive activated Notch (int-3). This is consistent with our previously published data that Notch4 is expressed in endothelial cells in vivo.

This data also suggest that RBE4 cells do not express the Notch4 ligand since RBE4 cells programmed to express Notch4 do not exhibit a spindle form morphology when grown in the absence of bFGF.

This data also demonstrates that over expression of Notch4 in RBE4 cells does not result in activation of the Notch4 receptor, because otherwise one would expect that these cells would have a similar phenotype to those cells that express a constitutive activated form of the Notch4 receptor.

This data demonstrates that Jagged or activated Notch4 induced activity can synergize or cooperate with bFGF.

REFERENCES CORRESPONDING TO THE SECOND SERIES OF EXPERIMENTS

Roux, et al. (1994) J. Cell Physiol. 159:101–13.

Zimrin, et al. An Antisense Oligonucleotide to the Notch Ligand Jagged Enhances Fibroblast Growth Factor-induced Angiogenesis in Vitro (1996) J. Biol. Chem. No. 51 271:32499–32502.

Third Series of Experiments

Notch4 and Jagged-1 Induce Microvessel Differentiation Of Rat Brain Endothelial Cells Introduction The mouse Notch4 gene is expressed specifically in endothelial cells. Notch4/int-3, a truncated form of Notch4, acts as a constitutive activated Notch receptor. We used Rat brain miscrovessel endothelial cells (RBE4) as a model system to study the role of Notch4 and Jagged-1 in endothelial cell differentiation. Both Notch4/int-3 and Jagged-1 were able to induce cellular structures with morphological and biochemical properties of endothelial microvessels. Ectopic expression of full length Notch4 did not have any discernible effect in RBE4 cells. Activation of the notch signal transduction pathway was measured by the induction of endogenous Notch4 and Jagged-1 genes. The observed morphological changes to RBE4 cells correlated with endogenous Notch4 and Jagged-1 gene activation, demonstrating a link between Notch signaling and biological activity. Our observations demonstrate that Notch signaling can promote endothelial cell differentiation.

Notch4 is a member of the Notch/lin-12 family of transmembrane receptors that are involved in cell fate determination (1,2). Like other Notch proteins, Notch4 extracellular domain is characterized by both Epidermal Growth Factor (EGF)—like repeats and lin-12/Notch repeats (LNR), and the intracellular domain contains ankyrin/cdc10 repeats (3). Analysis of invertebrate Notch/lin-12 mutants support a function for Notch/lin-12 receptors in intercellular signaling events that control cell fate. Mutants that delete the extracellular domain of C. elegans lin-12 or Drosophila Notch result in dominant gain-of-function phenotypes. The int-3 form of Notch4, Notch4/int-3, was identified based on its oncogenic effects in the mouse mammary gland and encodes only the transmembrane and intracellular domain of Notch4 (3–5). Notch4/int-3 behaves as a constitutively activated receptor (6–8). Similar activating mutations in the Notch1 gene have been identified in T lymphoblastic leukemia and can lead to neoplastic transformation in vitro (9,10).

Drosphila Delta (11) and Serrate (12) and C. elegans Lad-2 (13) and Apx-1 (14) encode a family Notch/lin-12 ligands that are transmembrane proteins whose extracellular domains contain EGF-like repeats and a DSL domain (Delta-Serrate-Lag-2). Based on homology to the Drosophila ligands, Notch ligands have also been identified in vertebrates. Jagged-1, a rat homologue of Drosophila Serrate, contains the hallmarks of a Notch ligand (15). Other putative mouse Notch ligands Delta-like 1 (16) and Delta-like 3 (17) have been identified and are closely related to Drosophila Delta. More recently, a human Jagged-2 gene has been identified (18). Although several Notch ligands and Notch receptors have been identified in mammals, it is not clear if ligands display distinct specificities towards different receptors.

Several genes encoding Notch ligands or receptors are expressed in the endothelium. Notch4 is expressed primarily in endothelial cells of the vasculature of mouse embryos and adult tissues (3, 19). Notch1 and Jagged-1 are also expressed in the endothelium, as well as a variety of other tissues (20–23). Recently, Jagged-1 was identified as gene induced during angiogenesis in vitro (24). A role of Notch in vascular development is suggested by analysis of mice with targeted disruption of genes encoding Notch ligands or Notch regulatory components. Mice deficient in either Delta like-1 (DII1) (25,26) or Jagged-1 develop severe hemorrhages (T. Gridley and G. Weinmaster, unpublished. data). Mice with targeted disruption of the Presenilin1 gene(26, 27), which facilitates Notch activity, display a loss of expression of Notch1, DII1 and exhibit hemorrhages in the brain and spinal cord. Evidence for involvement of Notch genes in vascular disorders has come from an analysis of a human hereditary adult onset condition causing stroke and dementia. CADASIL (cerebral autosomal dominant arteriopathy with subcortical infarcts and leukoenchepelopathy) is a human disorder manifested by stroke and dementia and characterized by non-amyloid and non-artherogenic angiopathy of cerebral arterioles (28). The CADASIL locus maps to the human Notch3 gene and mutations in Notch3 have been defined in CADASIL patients (29). Thus, alterations in Notch signaling may disrupt development and integrity of the vasculature.

As Notch functions in cell fate regulation in Drosophila and C. elegans, Notch receptors and their ligands expressed in endothelium may similarly control cell fate decisions during vascular development. We used the Rat brain endothelial cell line, FBE4, to study the role of Notch in endothelial cell differentiation. Ectopic expression of an activated Notch4/int-3 or of Jagged-1 in RBE4 cells induced cellular structures with morphological and biochemical properties of endothelial microvessels. Thus, activation of the Notch signaling pathway can promote endothelial differentiation.

Material and Methods

Immunohistochemistry

Frozen mouse kidney sections were fixed in 100% acetone and rinsed in 0.1% Triton X-100 in PBS (PBST) . Tissue sections were incubated in blocking solution (5% goat serum, 3% BSA in PBS) for 1 hour. Sections were covered with 1° antibody in dilution solution (1% goat serum, 3% BSA in PBS) for 12 hours at 40° C. The anti-PECAM) antibody (PharMingen) was used at a concentration of 3 $\mu$g/ml, the anti-mouse Notch4 immune-serum and pre-immune serum were diluted 500×. Tissue sections were rinsed in PBST and 2° antibodies (biotinylated goat anti-rat IgG and goat anti-rabbit IgG. labeled to alkaline phosphatase, both at 1:2000 dilutions) were applied in dilution buffer for 2 hours. Biotinylated goat anti-rat IgG was detected by the peroxidase technique (Vectastain Elite ABC kit, Vector Laboratories), and alkaline phosphatase labeled goat anti-rabbit IgG was detected as previously described (30). Sections for alkaline phosphatase staining were counter stained with eosine.

cDNA's

The Notch4/int-3 cDNA corresponds to a truncated Notch4 cDNA as described previously (3). An oligonucleotide sequence encoding the haemagglutinin (HA) eptope was appended to the 3' end of the Notch4/int-3 and Notch4 cDNA's as previously described (6). The presence of each fusion was confirmed by DNA sequencing. Similarly, a Jagged-1 cDNA was modified to encode an HA-tag at the carboxy terminus.

Cell Cultures and RBE4 Microvessel Outgrowth Assay

RBE4 cells were maintained in Alpha MEM/Ham's F10 (1:1) supplemented with 2 mM glutamine, 10% fetal calf serum and penicillin/streptomycin. For microvessel outgrowth assay, RBE4 cell lines were plated at equal cell densities (50% confluence). After 3 to 5 days, cell cultures were photographed (100× or 40×magnification).

Cell Lines

HA-tagged cDNAs were inserted into the retroviral vector pLHTCX wherein hygromycin-resistance gene is controlled by the murine leukemia virus (MLV) long terminal repeat (LTR), and cDNA transcription is controlled by an internal cytomegalovirus (CMV) promoter. Distinct populations of RBE4 cells,. either expressing Notch4/int-3 or Jagged-1 cDNA, were prepared by retroviral infection as described previously (6). The resultant populations, each comprised of at least 50 clones, were used in cellular and biochemical assays described below. Notch4 expressing cell lines were established by transfecting RBE4 cells directly by calcium phosphate transfection.

Immunoblot Analysis

HA epitope-tagged or non-tagged Notch4/int-3, Jagged-1 and Notch4 proteins from lysates of RBE4 cells were analyzed by immunoblotting as described previously (6). Lysates containing 20 μg protein were electophoresed and transferred to nitrocellulose filters, and subsequently, blocked in TBST (10 mM Tris, pH 8.0, 150 mM NaCl, 0.02% Tween-20) containing 1% BSA (TBST-BSA). Blots were then incubated with 1° antibody diluted (1:100 for 12CA5 (Berkeley Antibody Co.); 1:2000 for anti-Notch4) in TBST-BSA for 4 hours, washed in TBST, and incubated with 2° antibody in TBST-BSA for 1 hour. After 3 washes, the signal was visualized by chemiluminescence (Amersham, ECL).

Histochemical Enzyme Assay

Gamma-glutamyl transpeptidase (GTP) activity was demonstrated histochemically in cell cultures fixed in acetone, as described previously (31) : L-gamma-glutamyl-4methoxy-2-naphthylamide was used as substrate and glycyl-glycine as acceptor. In a simultaneous azo coupling reaction with Fastblue BB, a red azo dye is produced. Alkaline phosphatase (ALP) activity was determined in cell cultures fixed in citrate-buffered acetone, using the reaction mixture Sigma Kit N85, with naphtol ASMX phosphate as substrate and fast blue RR salt as diazonium salt, as previously described (31).

Northern Blot Analysis

Total RNA was isolated from RBE4 cell and Northern blot analysis was performed as described previously (3). $^{32}$P-radio labeled riboprobes were transcribed (Maxiscript, Ambion) from Notch1, Notch3, Notch4 and Jagged-1 cDNA's. Comparable amounts and integrity of the RNA were tested by hybridization with a B-actin probe.

Results

Notch4 Expression in Kidney Endothelial Cells

We previously described endothelial cell specific expression of Notch4 mRNA in mouse embryos and adult mouse lung, as analyzed in situ hybridization (3). To define the pattern of Notch4 protein expression, we generated an anti-Notch4 rabbit antiserum directed against a GST fusion protein containing the carboxy-terminus of Notch4 (32). The presence of endogenous Notch4 protein was analyzed in mouse kidney sections, as the kidney contains characteristic glomeruli with endothelial cell clusters in the renal cortex. We first analyzed Platelet Endothelial Cell Adhesion Molecule-1 (PECAM), an extracellular protein specifically expressed in endothelial and platelet cells. Antibodies against PECAM were used as a positive control in these experiments as they stained glomeruli (FIG. 1B). As shown in FIG. 1D, anti-Notch4 antibody specifically detects glomeruli in the kidney cortex in a similar pattern as the anti-PECAM antibody (FIG. 1B). Thus, data presented here demonstrates endothelial expression of Notch4 protein in the kidney.

The anti-Notch4 antibody was used to detect ectopically expressed Notch4 and Notch4/int-3 proteins by immunoblot analysis (FIG. 2C). Transiently transfected 293 cells expressed either HA epitope-tagged or non-epitope-tagged versions of Notch4 and Notch4/int-3. Immunoblot analysis of extracts from these cells displayed the full length Notch4 and Notch4/int-3 proteins which migrate with an approximate molecular weight of 220 and 70 kD respectively (FIG. 2B and C).

RBE4 Microvessel Outgrowth is Induced by Activated Notch4 and Jagged-1

Previous work has shown that the RBE4 cell line grown on collagen coated plates display a cobblestone morphology (31). When cultured in the presence of basic Fibroblast Growth Factor (bFGF), RBE4 cells change to a spindly morphology. When grown post-confluence, bFGF induces RBE4 cells to develop multi-cellular aggregates that arise from the monolayer. These three-dimensional aggregates consist of sprouts that extend above the monolayer and organize into curvilinear and bifurcating structures, resembling microvessels. bFGF-induced RBE4 microvessels contain high activity of alkaline phosphatase (ALP) and gamma glutamyl transpeptidase (GTP), which are specific enzymatic markers for differentiated endothelium and brain capillaries respectively (31).

RBE4 cell lines were programmed to express the HA-tagged Notch4/int-3, Jagged-1 and LacZ proteins using the retroviral vector pLHTCX. RBE4 cell lines programmed to express Notch4 were generated by direct transfection of the HA-tagged Notch4 cDNA. All three recombinant proteins were detected by immunoblot analysis of the respective RBE4 cell lines and migrated with their predicted molecular weight (220 kD for Notch4, 70 kD for Notch4/int-3, 150 kD for Jagged-1, see FIG. 2D).

The consequences of activating the Notch signaling pathway by ectopic expression of ligand (Jagged-1) or an activated receptor (Notch4/int-3) was analyzed in RBE4 cells. Control RBE4 cells expressing LacA (RBE-LacZ) growth arrest at confluence and do not develop three dimensional structures (FIG. 3A). When confluent RBE-LacZ cells were grown with bFGF (5 ng/ml), they form modest sprouts and microvessels (date not shown). RBE-LacZ were indistinguishable from wild type RBE4 cells grown under identical conditions. RBE4 cells programmed to express either Jagged-1 (RBE-Jagged-1) or Notch4/int-3 (RBE-Notch4/int-3) develop sprouts and three dimensional capillary-like structures (FIG. 3C and D) . These structures were not dependent on the presence of bFGF. These microvessel structures either float in the cell culture medium (although originating from a mount formed on the tissue culture plate) or are attached to the tissue culture plate. The extent of microvessel induction by Notch4/int-3 is far greater when compared to Jagged-1, as demonstrated in FIG. 3E and F. RBE4 cells programmed to express Notch4 (RBE-Notch4) do not form any microvessel structures (FIG. 3B). RBE-Notch4/int-3 or RBE-Jagged-1 cells displayed a more spindle shape morphology and do not form any microvessel structures (FIG. 3B). RBE-Notch4/int-3 or RBE-Jagged-1 cells displayed a more spindle shape morphology and no not form the cobblestone monolayer, as observed in RBE-LacZ or RBE-Notch4 (compare FIG. 3C and D with A or B). This morphological change is similar to when wild type RBE4 cells are treated with bFGF (31).

Microvessel structures induced by Jagged-1 and Notch4/int-3 in RBE4 cells were analyzed histochemically for the activities of two blood-brain barrier-associated enzymes, GTP and ALP. These enzymes are specifically expressed in the brain vasculature, and their expression is induced by bFGF treatment of RBE4 cells (31). ALP activity was detected in microvessel structures induced by either Notch4/int-3 (FIG. 4B) or by Jagged-1 (data not shown) GTP activity was also detected in both RBE-Jagged-1 (FIG. 4C) and RBE-Notch4/int-3 (data not shown). The detection of both ALP and GTP activities was specific for microvessel structures and not found in surrounding monolayer cells. RBE4 cell lines that did not exhibit microvessels, RBE-LacZ and RBE-Notch4, did not display ALP or GTP activities (data not shown).

Activation of the Notch Signal Transduction Pathway in RBE4 Cells

Jagged-1 and Notch4/int-3 expression resulted in similar phenotypes in RBE4 cells, thus we hypothesized that RBE4 cells must express endogenous Notch receptors that can be activated by Jagged-1. Northern Blot analysis demonstrated endogenous expression of Notch1, Notch3 and Notch4 transcripts (FIG. 5A). We also found that RBE4 cells express endogenous Jagged-1 transcripts (FIG. 5A). We could not make a statement about the relative levels of expression of Notch and Jagged transcripts as each lane in FIG. 5A utilized a different riboprobe.

Activation of Notch signaling has been reported to induce endogenous genes encoding Notch receptors and ligands (18). This induction can serve as a measure of signal activation and may lead to positive feedback control of Notch. genes by their ligands (33). To measure Notch signaling output in RBE4 cells, we assessed the level of endogenous Notch receptor and Notch ligand gene transcripts by northern blot analysis (FIG. 5B). RBE-Notch4/int-3 have increased levels of endogenous Notch4 (6.7 kb) and Jagged-1 transcripts (5.9 kb) (FIG. 5B, lane 2). The Notch4-specific riboprobe corresponds to the carboxy-terminal domain of Notch4, and can detect both ectopic Notch4/int-3 transcripts (1.8 kb) and endogenous Notch4 transcripts (6.7 kb). Notch4/int-3 expression in RBE cells specifically led to increased levels of endogenous Notch4 transcripts (FIG. 5B, lane 2) and not endogenous Notch1 (FIG. 5B, lane 2) or Notch3 transcripts (data not shown). RBE-Jagged-1 cells also have increased levels of endogenous Notch4 transcripts (FIG. 5B, lane 4). Again this activation is restricted to the endogenous Notch4 gene since the levels of Notch1 (FIG. 5B lane 4) and Notch3 (data not shown) transcripts remain unchanged. We were not able to ascertain if Jagged-1 expressing RBE4 cells up-regulated endogenous Jagged-1, since both the ectopic and endogenous Jagged-1 transcripts migrate with a similar molecular size (5.9 kb). RBE-Notch4 cells do not have increased levels of Notch1 (FIG. 5B, lane 3), Notch3 (data not shown) or Jagged-1 transcripts (FIG. 5B, lane 3). The level of Notch4 transcripts in these cells could not be evaluated since we can not distinguish by size between endogenous and ectopic Notch4 transcripts.

RBE4 cell lines were generated with retroviral vectors designed to express genes via an internal CMV promoter; however, gene expression may also be driven by the retroviral LTR leading to expression of two different sized transcripts. CMV-driven transcripts correspond to 1.8 kb for Notch4/int-3 6.7 kb for Notch 4 and 5.9 kb for Jagged-1 (FIG. 5B). Larger transcripts encompassing the complete retroviral genome originate from the LTF resulting in transcripts that are 3.5 kb larger than the CMV-driven transcripts. The LTR-driven transcripts are denoted in FIG. 5B (LTR) and correspond to 5.3 kb for Notch4/int-3, 10.2 kb for Notch4 and 9.4 kb for Jagged-1 (FIG. 5B). To clearly distinguish between the activated endogenous Notch4 transcripts (6.7 kb) and the LTR-driven Notch4/int-3 transcript (5.3 kb) a short exposure of a different northern blot from RBE-Notch4/int-3 cells is shown in FIG. 5B (lane 5 and 6). FIG. 5B lanes 2 and 6 both demonstrate that Notch4/int-3 activities expression of the endogenous Notch4 gene (6.7 kb).

Discussion

To investigate the role of Notch4 and Jagged-1 in endothelial cell differentiation we used an angiogenic in vitro model system, the RBE4 cell line. Previous studies have demonstrated that bFGF, a well characterized angiogenic factor, induces microvessel formation and the expression of markers specific for either differentiated endothelium (ALP) or the blood-brain barrier (GTP) (31). Ectopic expression of either Notch4/int-3 or Jagged-1 in RBE4 cells also results in the induction of microvessel structures that express both ALP and GTP. Full length Notch4 expression did not elicit any observable phenotype.

These studies suggest that Notch4/int-3 and Jagged-1 induce a biological activity in RBE4 cells that is similar to that induced by a known angiogenic agent bFGF. Thus, in rat brain endothelial cells, Notch activation results in an angiogenic response characterized by microvessel formation. Thus, Notch activation may regulate the angiogenic process in endothelium where Notch4 is found to be expressed, such as the vasculature of the adult kidney and lung.

Our data support the concept that Notch4/int-3 is a constitutive activated Notch allele as it induces a phenotype that is identical to when endogenous Notch receptors are activated by Jagged-1. We also note that ectopic expression of full length Notch4 in RBE4 cells does not result in Notch signal activation, thus receptor over expression does not lead to constitutive receptor activation. It may also suggest that RBE4 cells do not express a Notch4 ligand. Alternately RBE4 cells may not express Notch4 ligands at levels sufficient to activate the ectopically expressed Notch receptor. The induction of microvessel structures by Notch4/int-3 appears to be more robust when compared to the induction by Jagged-1 suggesting that a constitutive activated form of the Notch4 receptor is more potent in its activity than a Notch ligand (Jagged-1).

Since Jagged-1 is able to induce a biological activity that is similar to Notch4/int-3, we hypothesize that RBE4 cells must express endogenous Notch receptors which can be activated by Jagged-1. Northern blot analysis demonstrated that the Notch1, Notch3 and Notch4 genes are expressed in RBE4 cells. Notch1 and Notch4 are known to be expressed in endothelium in vivo (3, 19–23) and Notch3 may function in the vasculature (29). RBE4 cells also express Jagged-1 when analyzed by Northern blot. Thus, although RBE4 cells express endogenous transcripts that encode for both Notch proteins and one of their ligands, they do not spontaneously form microvessel structures. This observation may suggest that the levels of Notch proteins or ligands in RBE4 cells are insufficient to activate the Notch pathway.

We demonstrated that the Notch signal transduction pathway is activated in RBE4 cells expressing either Notch4/int-3 or Jagged-1. Activation of Notch signaling results in up-regulation of the endogenous Notch4 and Jagged-1 transcripts. Thus, the observed microvessel induction of RBE4 cells correlated with Notch signal activation. Both Jagged-1 and Notch4/int-3 expression resulted in a similar up-regulation of the endogenous Notch4 gene but neither altered the levels of Notch1 and Notch3 transcripts. Activation of a particular Notch signaling pathway, in this case Notch4, led to transcriptional activation events that are specific for distinct endogenous Notch genes. The observation that Jagged-1 results in an identical transcriptional activation pattern as activated Notch4/int-3 may suggest that Jagged-1 is a Notch4 ligand.

Previous work has demonstrated that activation of the Notch signal transduction pathway in mammalian cells inhibits differentiative or morphogenetic events. For instance, activated Notch1 and Notch2 are able to inhibit myogenic differentiation (15,34), and myeloid differentiation (35), and activated Notch4 (Notch4/int-3) is able to inhibit branching morphogenesis of mammary epithelial cells (6). In contrast, we found that activated Notch4/int-3 promoted the differentiation of RBE4 cells. Cell fate determination may involve either inhibition or promotion of differentiative steps. Our data is thus a clear demonstration that Notch signal activation can regulate cell fate decisions that involve the promotion of differentiation in mammalian cells.

Cell fate and cell differentiation decisions likely play important roles during vascular development. Although some factors have been identified that regulate vascular growth, little is known about how these or other factors may regulate cell fate decisions (36). Our data suggest that Notch proteins and their ligands can promote differentiation and may be important in regulating cell fate decisions in the developing vasculature.

We thank Iva Greenwald, Sam Silverstein, Cissy Young, and Stefan Pukatzki for critically reading the manuscript. This work was supported by a grant to J.K. from the U.S. Army Medical Research and Material Command (USAMRMC)under grant DAMD17-94-J-4410, by a predoctoral fellowships from the USAMRMC to H.U. under grant DAMD17-94-J-4153 and G.W. under grant DAMD17-97-1-7291.

REFERENCES CORRESPONDING TO THE THIRD SERIES OF EXPERIMENTS

1. Artavanis-Tsakonas, S., Matsuno, K. & Fortini, M. E. (1995) Science 268, 225–232.
2. Baudrimont, M., Dubas, F., Joutel, A., Tournier-Lasserve, E. & Bousser, M. G. (1993) Stroke 24, 122–125.
3. Bettenhausen, B., Hrabe de Angelis, M., Simon, D., Guenet, J. L.& Gossler, A. (1995) Development 121, 2407–2418.
4. Bigas, A., Martin, D. & Milner, L. (1998) Mol. Cell. Biol. 18, 2324–2333.
5. Capobianco, A. J., Zagouras, P., Blaumueller, C. M., Artavanis-Tsakonas, S. & Bishop, J. M. (1997) Mol Cell Biol 17, 6265–6273.
6. Dunwoodie, S. L., Henrique, D., Harrison, S. M. & Beddington, R. S. (1997) Development 124, 3065–3076.
7. Ellisen, L. W., Bird, J., West, D. C., Soreng, A. L., Reynolds, T. C., Smith, S. D. & Sklar, J. (1991) Cell 66, 649–661.
8. Fleming, R. J., Scottgale, T. N., Diederich, R. J. & Artavinis-Tsakonas, S. (1990) Genes Dev. 4, 2188–2201.
9. Foux, F., Durieu-Trautmann, O., Chaverot, N., Claire, M., Mailly, P., Bourre, J. M., Strosberg, A. D. & Couraud, P. O. (1994) J. Cell. Physiol. 159, 101–113.
10. Franco Del Amo, F., Smith, D. E., Swiatek, P. J., Gendron-Maguire, M., Greenspan, R. J., McMahon, A. P. & Gridley, T. (1992) Development 115, 737–744.
11. Gallahan, D. & Callahan, R. (1997) Oncogene 14, 1883–1890.
12. Gallahan, D., Jhappan, C., Robinson, G., Hennighausen, L., Sharp, R., Kordon, E., Callahan, R., Merlino, G. & Smith, G. H. (1996) Cancer Res. 56, 1775–1785.
13. Gallahan, D., Kozak, C. & Callahan, R. (1987) J. Virol. 61, 218–220.
14. Greenwald, I. (1994) Curr. Opin. Genet. Dev. 4, 556–562.
15. Hanahan, D. (1997) Science 277, 48–50.
16. Hrabe de Angelis, M., McIntyre II, J. & A., G. (1997) Nature 386, 717–721.
17. Hsieh, J. J., Nofziger, D. E., Weinmaster, G. & Hayward, S. D. (1997) J. Virol 71, 1938–1945.
18. Hubbard, E. J, A., Wu, G., Kitajewski, J. & Greenwald, I. (1997) Genes Dev. 11, 3182–3193.
19. Jhappan, C., Gallahan, D., Stahle, C., Chu, E., Smith, G. H., Merline, G. & Callahan, R. (1992) Genes Dev. 6, 345–355.
20. Joutel, A., Corpechot, C., Ducros, A., Vahedi, K., Chabriat, H., Mouton, P., Alamowitch, S., Domenga, V., Cecillion, M., Marechal, E., Maciazek, J., Vayssiere, C., Cruaud, C., Cabanis, E. A., Ruchoux, M. M., Weissenbach, J., Bach, J. F., Bousser, M. G. & Tournier-Lasserve, E. (1996) Nature 383, 707–710.
21. Lindsell, C. E., Boulter, J., diSibio, G., Gossler, A. & Weinmaster, G. (1996) Molecular & Cellular Neurosciences 8, 14–27.
22. Lindsell, C. E., Shawber, C. J., Boulter, J. & Weinmaster, G. (1995) Cell 80, 909–917.
23. Luo, B., Aster, J. C., Hasserjian, R. P., Kuo, F. & Sklar, J. (1997) Mol Cell Biol 17, 6057–6067.
24. Mello, C. C., Draper, B. W. & Priess, J. R. (1994) Cell 77, 95–106.
25. Myat, A., Henrique, D., Ish-Horowicz, D. & Lewis, J. (1996) Dev. Biol. 174, 233–247.
26. Reaume, A. G., Conlon, R. A., Zirngibl, R., yamaguchi, T. P. & Rossant, J. (1992) J. Dev. Biol. 154, 377–387.
27. Shen, J., Bronson, R. T., Chen, D. F., Xia, W., Selkoe, D. J. & Tonegawa, S. (1997) Cell 89, 629–639.
28. Sirayoshi, Y., Yuasa, Y., Suzuki, T., Sugaya, K., Kawase, E., Ikemura, T. & Nakatsuki, N. (1997) Genes Cells 2, 213–224.
29. Tax, F. E., Yeargers, J. J. & Thomas, J. H. (1994) Nature 368, 150–154.
30. Uyttendaele, H., Marazzi, G., Wu, G., Yan, Q., Sassoon, D. & Kitajewski, J. (1996) Development 122, 2251–2259.
31. Uyttendaele, H., Soriano, J. V., Montesano, F. & Kitajewski, J. (1998) Dev. Biol. 196, in press.
32. Vassin, H., Bremer, K. A, Knust, E. & Campos-Ortega, J. A. (1987) EMBO J. 6, 3431–3440.
33. Wilkinson, H. A., Fitzgerald, K. & Greenwald, I. (1994) Cell 79, 1187–1198.
34. Wong, P. C., Zheng, H., Chen, H., Becher, M. W., Siringathsinghji, D. J. S., Trumbauer, M. E., H. Y., C., Price, D. L., Van der Ploeg, L. H. T. & Sisodia, S. S. (1997) Nature 387, 288–292.
35. Zhang, Q, Ahuja, H. S., Zakeri, Z. F. & Wolgemuth, D. J. (1997) Dev. Biol 183, 222–233.
36. Zimrin, A. B., Pepper, M. S., McMahon, G. A., Nguyen, F., Montesano, R. & Maciag, T. (1996) J. Biol. Chem. 271, 32499–32502.

What is claimed is:

1. An isolated nucleic acid encoding a protein having the amino acid sequence shown in FIGS. 1A and 1B (SEQ ID NO:1).

2. The isolated nucleic acid of claim 1, wherein the nucleic acid is DNA or RNA.

3. The isolated nucleic acid of claim 2, wherein the DNA is selected from the group consisting of cDNA and synthetic DNA.

4. The isolated nucleic acid of claim 2, comprising the sequence set forth in FIG. 9 (SEQ ID NO:6).

5. An isolated nucleic acid encoding a protein having the cytosolic portion of the amino acid sequence shown in FIGS. 1A and 1B (SEQ ID NO:1).

6. The isolated nucleic acid of claim 5, wherein the nucleic acid is DNA or RNA.

7. The isolated nucleic acid of claim 5, wherein the DNA is selected from the group consisting of genomic DNA, cDNA and synthetic DNA.

8. A vector which comprises the isolated nucleic acid of claim 1 or 5.

9. The vector of claim 8, wherein the isolated nucleic acid is operatively linked to a regulatory element.

10. The vector of claim 8, wherein the vector is a plasmid.

11. The vector of claim 9 designated pBS-Notch4 and found in the cell line hating ATCC Designation No. 209121.

12. A host vector system for the production of a protein comprising the vector of claim 9 in a host cell.

13. The host vector system of claim 12, wherein the host cell is a prokaryotic or eukaryotic cell.

14. A method of transforming a host cell comprising transfecting the host cell with the vector of claim 9.

15. A transformed host cell produced by the method of claim 14.

16. The transformed host cell of claim 15, wherein the host cell, when not transformed, does not express the protein encoded by the transforming vector.

17. The transformed host cell of claim 15 which expresses the protein encoded by the transforming vector.

18. The host vector system of claim 12, wherein the host cell is a bacterial, yeast, plant, or animal cell.

19. A method of producing a protein comprising culturing the host vector system of claim 12 under conditions permitting production of the protein encoded by the vector therein, and recovering the protein so produced.

* * * * *

SEQUENCE LISTING

<160> NUMBER OF SEQ ID NOS: 10

<210> SEQ ID NO 1
<211> LENGTH: 1964
<212> TYPE: PRT
<213> ORGANISM: mouse

<400> SEQUENCE: 1

Met Gln Pro Gln Leu Leu Leu Leu Leu Leu Leu Pro Leu Asn Phe Pro

-continued

```
  1                   5                  10                  15
Val Ile Leu Thr Arg Glu Leu Leu Cys Gly Gly Ser Pro Glu Pro Cys
                    20                  25                  30

Ala Asn Gly Gly Thr Cys Leu Arg Leu Ser Arg Gly Gln Gly Ile Cys
             35                  40                  45

Gln Cys Ala Pro Gly Phe Leu Gly Glu Thr Cys Gln Phe Pro Asp Pro
     50                  55                  60

Cys Arg Asp Thr Gln Leu Cys Lys Asn Gly Gly Ser Cys Gln Ala Leu
 65                  70                  75                  80

Leu Pro Thr Pro Pro Ser Ser Arg Ser Pro Thr Ser Pro Leu Thr Pro
                 85                  90                  95

His Phe Ser Cys Thr Cys Pro Ser Gly Phe Thr Gly Asp Arg Cys Gln
             100                 105                 110

Thr His Leu Glu Glu Leu Cys Pro Pro Ser Phe Cys Ser Asn Gly Gly
         115                 120                 125

His Cys Tyr Val Gln Ala Ser Gly Arg Pro Gln Cys Ser Cys Glu Pro
     130                 135                 140

Gly Trp Thr Gly Glu Gln Cys Gln Leu Arg Asp Phe Cys Ser Ala Asn
145                 150                 155                 160

Pro Cys Ala Asn Gly Gly Val Cys Leu Ala Thr Tyr Pro Gln Ile Gln
                 165                 170                 175

Cys Arg Cys Pro Pro Gly Phe Glu Gly His Thr Cys Glu Arg Asp Ile
             180                 185                 190

Asn Glu Cys Phe Leu Glu Pro Gly Pro Cys Pro Gln Gly Thr Ser Cys
         195                 200                 205

His Asn Thr Leu Gly Ser Tyr Gln Cys Leu Cys Pro Val Gly Gln Glu
     210                 215                 220

Gly Pro Gln Cys Lys Leu Arg Lys Gly Ala Cys Pro Pro Gly Ser Cys
225                 230                 235                 240

Leu Asn Gly Gly Thr Cys Gln Leu Val Pro Glu Gly His Ser Thr Phe
                 245                 250                 255

His Leu Cys Leu Cys Pro Pro Gly Phe Thr Gly Leu Asp Cys Glu Met
             260                 265                 270

Asn Pro Asp Asp Cys Val Arg His Gln Cys Gln Asn Gly Ala Thr Cys
         275                 280                 285

Leu Asp Gly Leu Asp Thr Tyr Thr Cys Pro Cys Pro Lys Thr Trp Lys
     290                 295                 300

Gly Trp Asp Cys Ser Glu Asp Ile Asp Glu Cys Glu Ala Arg Gly Pro
305                 310                 315                 320

Pro Arg Cys Arg Asn Gly Gly Thr Cys Gln Asn Thr Ala Gly Ser Phe
                 325                 330                 335

His Cys Val Cys Val Ser Gly Trp Gly Gly Ala Gly Cys Glu Glu Asn
             340                 345                 350

Leu Asp Asp Cys Ala Ala Ala Thr Cys Ala Pro Gly Ser Thr Cys Ile
         355                 360                 365

Asp Arg Val Gly Ser Phe Ser Cys Leu Cys Pro Pro Gly Arg Thr Gly
     370                 375                 380

Leu Leu Cys His Leu Glu Asp Met Cys Leu Ser Gln Pro Cys His Val
385                 390                 395                 400

Asn Ala Gln Cys Ser Thr Asn Pro Leu Thr Gly Ser Thr Leu Cys Ile
                 405                 410                 415

Cys Gln Pro Gly Tyr Ser Gly Ser Thr Cys His Gln Asp Leu Asp Glu
             420                 425                 430
```

```
Cys Gln Met Ala Gln Gly Pro Ser Pro Cys Glu His Gly Gly Ser
        435                 440                 445

Cys Ile Asn Thr Pro Gly Ser Phe Asn Cys Leu Cys Leu Pro Gly Tyr
        450                 455                 460

Thr Gly Ser Arg Cys Glu Ala Asp His Asn Glu Cys Leu Ser Gln Pro
465                 470                 475                 480

Cys His Pro Gly Ser Thr Cys Leu Asp Leu Leu Ala Thr Phe His Cys
                485                 490                 495

Leu Cys Pro Pro Gly Leu Glu Gly Arg Leu Cys Glu Val Glu Val Asn
            500                 505                 510

Glu Cys Thr Ser Asn Pro Cys Leu Asn Gln Ala Ala Cys His Asp Leu
        515                 520                 525

Leu Asn Gly Phe Gln Cys Leu Cys Leu Pro Gly Phe Thr Gly Ala Arg
        530                 535                 540

Cys Glu Lys Asp Met Asp Glu Cys Ser Ser Thr Pro Cys Ala Asn Gly
545                 550                 555                 560

Gly Arg Cys Arg Asp Gln Pro Gly Ala Phe Tyr Cys Glu Cys Leu Pro
                565                 570                 575

Gly Phe Glu Gly Pro His Cys Glu Lys Glu Val Asp Glu Cys Leu Ser
            580                 585                 590

Asp Pro Cys Pro Val Gly Ala Ser Cys Leu Asp Leu Pro Gly Ala Phe
        595                 600                 605

Phe Cys Leu Cys Arg Pro Gly Phe Thr Gly Gln Leu Cys Glu Val Pro
        610                 615                 620

Leu Cys Thr Pro Asn Met Cys Gln Pro Gly Gln Gln Cys Gln Gly Gln
625                 630                 635                 640

Glu His Arg Ala Pro Cys Leu Cys Pro Asp Gly Ser Pro Gly Cys Val
                645                 650                 655

Pro Ala Glu Asp Asn Cys Pro Cys His His Gly His Cys Gln Arg Ser
            660                 665                 670

Leu Cys Val Cys Asp Glu Gly Trp Thr Gly Pro Glu Cys Glu Thr Glu
        675                 680                 685

Leu Gly Gly Cys Ile Ser Thr Pro Cys Ala His Gly Gly Thr Cys His
        690                 695                 700

Pro Gln Pro Ser Gly Tyr Asn Cys Thr Cys Pro Ala Gly Tyr Met Gly
705                 710                 715                 720

Leu Thr Cys Ser Glu Glu Val Thr Ala Cys His Ser Gly Pro Cys Leu
                725                 730                 735

Asn Gly Gly Ser Cys Ser Ile Arg Pro Glu Gly Tyr Ser Cys Thr Cys
            740                 745                 750

Leu Pro Ser His Thr Gly Arg His Cys Gln Thr Ala Val Asp His Cys
        755                 760                 765

Val Ser Ala Ser Cys Leu Asn Gly Gly Thr Cys Val Asn Lys Pro Gly
        770                 775                 780

Thr Phe Phe Cys Leu Cys Ala Thr Gly Phe Gln Gly Leu His Cys Glu
785                 790                 795                 800

Glu Lys Thr Asn Pro Ser Cys Ala Asp Ser Pro Cys Arg Asn Lys Ala
                805                 810                 815

Thr Cys Gln Asp Thr Pro Arg Gly Ala Arg Cys Leu Cys Ser Pro Gly
            820                 825                 830

Tyr Thr Gly Ser Ser Cys Gln Thr Leu Ile Asp Leu Cys Ala Arg Lys
        835                 840                 845
```

-continued

Pro Cys Pro His Thr Ala Arg Cys Leu Gln Ser Gly Pro Ser Phe Gln
850                 855                 860

Cys Leu Cys Leu Gln Gly Trp Thr Gly Ala Leu Cys Asp Phe Pro Leu
865                 870                 875                 880

Ser Cys Gln Lys Ala Ala Met Ser Gln Gly Ile Glu Ile Ser Gly Leu
            885                 890                 895

Cys Gln Asn Gly Gly Leu Cys Ile Asp Thr Gly Ser Ser Tyr Phe Cys
            900                 905                 910

Arg Cys Pro Pro Gly Phe Gln Gly Lys Leu Cys Gln Asp Asn Val Asn
            915                 920                 925

Pro Cys Glu Pro Asn Pro Cys His His Gly Ser Thr Cys Val Pro Gln
930                 935                 940

Pro Ser Gly Tyr Val Cys Gln Cys Ala Pro Gly Tyr Glu Gly Gln Asn
945                 950                 955                 960

Cys Ser Lys Val Leu Asp Ala Cys Gln Ser Gln Pro Cys His Asn His
                965                 970                 975

Gly Thr Cys Thr Ser Arg Pro Gly Gly Phe His Cys Ala Cys Pro Pro
            980                 985                 990

Gly Phe Val Gly Leu Arg Cys Glu Gly Asp Val Asp Glu Cys Leu Asp
            995                 1000                1005

Arg Pro Cys His Pro Ser Gly Thr Ala Ala Cys His Ser Leu Ala Asn
    1010                1015                1020

Ala Phe Tyr Cys Gln Cys Leu Pro Gly His Thr Gly Gln Arg Cys Glu
1025                1030                1035                1040

Val Glu Met Asp Leu Cys Gln Ser Gln Pro Cys Ser Asn Gly Gly Ser
                1045                1050                1055

Cys Glu Ile Thr Thr Gly Pro Pro Gly Phe Thr Cys His Cys Pro
            1060                1065                1070

Lys Gly Phe Glu Gly Pro Thr Cys Ser His Lys Ala Leu Ser Cys Gly
    1075                1080                1085

Ile His His Cys His Asn Gly Gly Leu Cys Leu Pro Ser Pro Lys Pro
    1090                1095                1100

Gly Ser Pro Pro Leu Cys Ala Cys Leu Ser Gly Phe Gly Gly Pro Asp
1105                1110                1115                1120

Cys Leu Thr Pro Pro Ala Pro Pro Gly Cys Gly Pro Pro Ser Pro Cys
            1125                1130                1135

Leu His Asn Gly Thr Cys Thr Glu Thr Pro Gly Leu Gly Asn Pro Gly
            1140                1145                1150

Phe Gln Cys Thr Cys Pro Pro Asp Ser Pro Gly Pro Arg Cys Gln Arg
            1155                1160                1165

Pro Gly Ala Ser Gly Cys Glu Gly Arg Gly Gly Asp Gly Thr Cys Asp
1170                1175                1180

Ala Gly Cys Ser Gly Pro Gly Gly Asp Trp Asp Gly Gly Asp Cys Ser
1185                1190                1195                1200

Leu Gly Val Pro Asp Pro Trp Lys Gly Cys Pro Pro His Ser Gln Cys
            1205                1210                1215

Trp Leu Leu Phe Arg Asp Gly Arg Cys His Pro Gln Cys Asp Ser Glu
            1220                1225                1230

Glu Cys Leu Phe Asp Gly Tyr Asp Cys Glu Ile Pro Pro Thr Cys Ile
    1235                1240                1245

Pro Ala Tyr Asp Gln Tyr Cys Arg Asp His Phe His Asn Gly His Cys
    1250                1255                1260

Glu Lys Gly Cys Asn Asn Ala Glu Cys Gly Trp Asp Gly Gly Asp Cys

-continued

```
1265                1270                1275                1280

Arg Pro Glu Gly Glu Asp Ser Glu Gly Arg Pro Ser Leu Ala Leu Leu
                1285                1290                1295

Val Val Leu Arg Pro Pro Ala Leu Asp Gln Gln Leu Leu Ala Leu Ala
            1300                1305                1310

Arg Val Leu Ser Leu Thr Leu Arg Val Gly Leu Trp Val Arg Lys Asp
        1315                1320                1325

Ser Glu Gly Arg Asn Met Val Phe Pro Tyr Pro Gly Thr Arg Ala Lys
    1330                1335                1340

Glu Glu Leu Ser Gly Ala Arg Asp Ser Ser Ser Trp Glu Arg Gln Ala
1345                1350                1355                1360

Pro Pro Thr Gln Pro Leu Gly Lys Glu Thr Glu Ser Leu Gly Ala Gly
                1365                1370                1375

Phe Val Val Met Gly Val Asp Leu Ser Arg Cys Gly Pro Glu His
            1380                1385                1390

Pro Ala Ser Arg Cys Pro Trp Asp Ser Gly Leu Leu Leu Arg Phe Leu
        1395                1400                1405

Ala Ala Met Ala Ala Val Gly Ala Leu Glu Pro Leu Leu Pro Gly Pro
    1410                1415                1420

Leu Leu Ala Ala His Pro Gln Ala Gly Thr Arg Pro Pro Ala Asn Gln
1425                1430                1435                1440

Leu Pro Trp Pro Ile Leu Cys Ser Pro Val Val Gly Val Leu Leu Leu
                1445                1450                1455

Ala Leu Gly Ala Leu Leu Val Leu Gln Leu Ile Arg Arg Arg Arg Arg
            1460                1465                1470

Glu His Gly Ala Leu Trp Leu Pro Pro Gly Phe Ile Arg Arg Pro Gln
        1475                1480                1485

Thr Gln Gln Ala Pro His Arg Arg Arg Pro Pro Leu Gly Glu Asp Asn
    1490                1495                1500

Ile Gly Leu Lys Ala Leu Lys Pro Glu Ala Glu Val Asp Glu Asp Gly
1505                1510                1515                1520

Val Ala Met Cys Ser Gly Pro Glu Glu Gly Glu Ala Glu Glu Thr Ala
                1525                1530                1535

Ser Ala Ser Arg Cys Gln Leu Trp Pro Leu Asn Ser Gly Cys Gly Glu
            1540                1545                1550

Leu Pro Gln Ala Ala Met Leu Thr Pro Pro Gln Glu Cys Glu Ser Glu
        1555                1560                1565

Val Leu Asp Val Asp Thr Cys Gly Pro Asp Gly Val Thr Pro Leu Met
    1570                1575                1580

Ser Ala Val Phe Cys Gly Gly Val Gln Ser Thr Thr Gly Ala Ser Pro
1585                1590                1595                1600

Gln Arg Leu Gly Leu Gly Asn Leu Glu Pro Trp Glu Pro Leu Leu Asp
                1605                1610                1615

Arg Gly Ala Cys Pro Gln Ala His Thr Val Gly Thr Gly Glu Thr Pro
            1620                1625                1630

Leu His Leu Ala Ala Arg Phe Ser Arg Pro Thr Ala Ala Arg Arg Leu
        1635                1640                1645

Leu Glu Ala Gly Ala Asn Pro Asn Gln Pro Asp Arg Ala Gly Arg Thr
    1650                1655                1660

Pro Leu His Thr Ala Val Ala Ala Asp Ala Arg Glu Val Cys Gln Leu
1665                1670                1675                1680

Leu Leu Ala Ser Arg Gln Thr Thr Val Asp Ala Arg Thr Glu Asp Gly
                1685                1690                1695
```

-continued

```
Thr Thr Pro Leu Met Leu Ala Ala Arg Leu Ala Val Glu Asp Leu Val
        1700                1705                1710
Glu Glu Leu Ile Ala Ala Arg Ala Asp Val Gly Ala Arg Asp Lys Arg
    1715                1720                1725
Gly Lys Thr Ala Leu His Trp Ala Ala Ala Val Asn Asn Ala Arg Ala
    1730                1735                1740
Ala Arg Ser Leu Leu Gln Ala Gly Ala Asp Lys Asp Ala Gln Asp Ser
1745                1750                1755                1760
Arg Glu Gln Thr Pro Leu Phe Leu Ala Ala Arg Glu Gly Ala Val Glu
            1765                1770                1775
Val Ala Gln Leu Leu Leu Glu Leu Gly Ala Ala Arg Gly Leu Arg Asp
        1780                1785                1790
Gln Ala Gly Leu Ala Pro Gly Asp Val Ala Arg Gln Arg Ser His Trp
        1795                1800                1805
Asp Leu Leu Thr Leu Leu Glu Gly Ala Gly Pro Thr Thr Gln Glu Ala
        1810                1815                1820
Arg Ala His Ala Arg Thr Thr Pro Gly Gly Gly Ser Ala Pro Arg Cys
1825                1830                1835                1840
Arg Thr Leu Ser Ala Gly Ala Arg Pro Arg Gly Gly Gly Ala Cys Leu
            1845                1850                1855
Gln Ala Arg Thr Trp Ser Val Asp Leu Gly Ala Arg Gly Gly Lys Val
            1860                1865                1870
Tyr Ala Arg Cys Arg Ser Arg Ser Gly Ser Cys Gly Gly Pro Thr Thr
        1875                1880                1885
Arg Gly Arg Arg Phe Ser Ala Gly Ser Arg Gly Arg Gly Ala Arg
        1890                1895                1900
Ala Ser Gln Asp Asp Trp Pro Arg Asp Trp Val Ala Leu Glu Ala Cys
1905                1910                1915                1920
Gly Ser Ala Cys Ser Ala Pro Ile Pro Pro Ser Leu Thr Pro Ser
            1925                1930                1935
Pro Glu Arg Gly Ser Pro Gln Val Ala Trp Gly Leu Pro Val His Gln
            1940                1945                1950
Glu Ile Pro Leu Asn Ser Val Val Arg Asn Leu Asn
        1955                1960

<210> SEQ ID NO 2
<211> LENGTH: 40
<212> TYPE: PRT
<213> ORGANISM: mouse

<400> SEQUENCE: 2

Gln Asp Val Asp Glu Cys Asp Leu Gly Ala Asn Arg Cys Glu His Ala
1               5                   10                  15
Gly Lys Cys Leu Asn Thr Leu Gly Ser Phe Glu Cys Gln Cys Leu Gln
            20                  25                  30
Gly Tyr Thr Gly Pro Gly Cys Glu
        35                  40

<210> SEQ ID NO 3
<211> LENGTH: 41
<212> TYPE: PRT
<213> ORGANISM: mouse

<400> SEQUENCE: 3

Glu Asp Val Asp Glu Cys Ala Met Ala Asn Ser Asn Pro Cys Glu His
1               5                   10                  15
```

```
Ala Gly Lys Cys Val Asn Thr Asp Gly Ala Phe His Cys Glu Cys Leu
            20                  25                  30

Lys Gly Tyr Ala Gly Pro Arg Cys Glu
        35                  40

<210> SEQ ID NO 4
<211> LENGTH: 39
<212> TYPE: PRT
<213> ORGANISM: mouse

<400> SEQUENCE: 4

Gln Asp Val Asp Glu Cys Ser Ile Gly Ala Asn Pro Cys Glu His Leu
 1               5                  10                  15

Gly Arg Cys Val Thr Gln Gly Ser Phe Leu Cys Gln Cys Gly Arg Gly
            20                  25                  30

Tyr Thr Gly Pro Arg Cys Glu
        35

<210> SEQ ID NO 5
<211> LENGTH: 43
<212> TYPE: PRT
<213> ORGANISM: mouse

<400> SEQUENCE: 5

Gln Asp Leu Asp Glu Cys Gln Met Ala Gln Gln Gly Pro Ser Pro Cys
 1               5                  10                  15

Glu His Gly Gly Ser Cys Ile Asn Thr Pro Gly Ser Phe Asn Cys Leu
            20                  25                  30

Cys Leu Pro Gly Tyr Thr Gly Ser Arg Cys Glu
        35                  40

<210> SEQ ID NO 6
<211> LENGTH: 6677
<212> TYPE: DNA
<213> ORGANISM: mouse

<400> SEQUENCE: 6
gggaaaacag gtgtgtttct gccttttact tctaacttgg aataccttac ccaatcccag     60
ttcttcatct cctctgagaa gttatagggt taaaaatatt gtcttcttac atcagcagat    120
atatgacaag ggaagagatc ctttggtcag ctctagtaat ctggctttgt ccccttaggg   180
gaatagactt tggcctgagg gaacagctca gactgaggcg tgcagcaggc tcaggaggaa    240
gaagggcggt agaagcagag gaagtggcct tgcctggcca caagggctct gagggtccct    300
gcctgaagag ggagaggaga tccgggccag ggcaggtgc tctggaatgc agccccagtt     360
gctgctgctg ctgctcttgc cactcaattt ccctgtcatc ctgaccagag agcttctgtg    420
tggaggatcc ccagagccct gtgccaacgg aggcacctgc tgaggctat ctcggggaca    480 agggatctgc cagtgtgccc ctggatttct gggtgagact tgccagtttc ctgaccctg    540 cagggatacc caactctgca agaatggtgg cagctgccaa gccctgctcc ccacaccccc    600
aagctcccgt agtcctactt ctccactgac ccctcacttc tcctgcacct gcccctctgg    660
cttcaccggt gatcgatgcc aaacccatct ggaagagctc tgtccacctt ctttctgttc    720
caacgggggt cactgctatg ttcaggcctc aggccgccca cagtgctcct gcgagcctgg   780
gtggacaggt gagcaatgcc agctccgaga cttctgctca gccaacccct gtgccaacgg    840
aggcgtgtgc ctggccacat accccagat ccagtgccgc tgtccacctg ggttcgaggg    900
```

-continued

```
tcacacctgt gaacgcgaca tcaacgagtg cttcctggag ccgggaccct gccctcaggg    960
cacctcctgc cataacacct tgggttccta ccagtgtctc tgccctgtgg ggcaggaagg   1020
tccccagtgc aagctcagga agggagcctg ccctcctgga agctgtctca atgggggcac   1080
ctgccagctg gtcccagagg gacactccac ctttcatctc tgcctctgtc ccccaggttt   1140
cacggggctg gactgtgaga tgaacccaga tgactgtgtc aggcaccagt gtcagaacgg   1200
ggccacctgt ctggatgggc tggatatccta cacctgcccc tgccccaaga catggaaggg   1260
ctgggactgc tctgaagata tagatgaatg tgaagcccgg ggtcccccte gctgcaggaa   1320 cggtggcacc tgccagaaca cagctggcag ctttcactgt gtgtgcgtga gtggctgggg   1380
aggtgcaggc tgtgaggaga acctggatga ctgtgcagct gccacctgtg ccccgggatc   1440
cacctgcatc gaccgtgtgg gctctttctc ctgcctctgc ccacctggac gcacaggcct   1500
cctgtgccac ctggaagaca tgtgtttgag tcagccgtgc cacgtgaatg cccagtgcag   1560
caccaaccct ctgacaggct ccaccctctg catatgccag cctggctact caggatccac   1620
ctgtcaccaa gatctggatg agtgccaaat ggcccagcaa ggacccagtc cctgcgaaca   1680 tgggggtcc tgcatcaaca cccctggctc cttcaactgc ctctgcctgc ctggttacac   1740
gggctcccgc tgtgaagctg accacaatga gtgcctgtca cagccctgcc acccaggcag   1800
cacctgcctg gacctgcttg caaggttcca ctgcctctgc ccaccaggct tggaagggag   1860
actctgtgag gtggaggtca atgagtgcac ctctaatccc tgcctgaacc aagctgcctg   1920
ccatgacctg ctcaacggct tccagtgcct ctgccttcct ggattcaccg cgccccgatg   1980
tgagaaagac atggacgagt gtagcagcac cccctgtgcc aatggggggc gctgccgaga   2040
ccagcctgga gccttctact gcgagtgtct cccaggcttt gaagggccac actgtgagaa   2100
agaagtggac gaatgtctga gtgacccctg tccegtggga gccagctgtc ttgatctccc   2160
cggagcattc ttctgtctct gccgtcctgg tttcacaggt caactttgtg aggttccctt   2220
gtgcaccccc aacatgtgcc aacctggaca gcaatgccaa ggtcaggaac acagagcccc   2280
ctgcctctgc cctgacggaa gtcctggctg tgttcctgcc gaggacaact gcccctgtca   2340
ccatggccat tgccagagat ccttgtgtgt gtgtgatgag ggctggactg gaccagaatg   2400
cgagacagaa ctgggtggct gcatctccac accctgtgcc catgggggga cctgccaccc   2460
acagccatct ggctacaact gtacctgccc tgcaggctac atggggttga cctgtagtga   2520
ggaggtgaca gcttgtcact cagggccctg tctcaatggt ggctcctgca gcatccgtcc   2580
tgagggctat tcctgcacct gccttccaag tcacacaggt cgccactgcc agactgccgt   2640
ggaccactgt gtgtctgcct cgtgcctcaa tgggggtacc tgtgtgaaca gcctggcac   2700 tttcttctgc ctctgtgcca ctggcttcca ggggctgcac tgtgaggaga agactaaccc   2760
cagctgtgca gacagcccct gcaggaacaa ggcaacctgc caagacacac ctcgaggggc   2820
ccgctgcctc tgcagccctg gctatacagg aagcagctgc cagactctga tagacttgtg   2880
tgcccggaag ccctgtccac acactgctcg atgcctccag agtgggccct cgttccagtg   2940
cctgtgcctc cagggatgga cagggctct ctgtgacttc ccactgtcct gccagaaggc   3000
cgcgatgagc caaggcatag agatctctgg cctgtgccag aatggaggcc tctgtattga   3060
cacgggctcc tcctatttct gccgctgccc tcctggattc aaggcaagt tatgccagga   3120 taatgtgaac cctgcgagc caatccctg ccatcacggg tctacctgtg tgcctcagcc   3180
cagtggctat gtctgccagt gtgccccagg ctatgaggga cagaactgct caaaagtact   3240
tgacgcttgt cagtcccagc cctgccacaa ccacggaacc tgtacctcca ggcctggagg   3300
```

-continued

```
cttccactgt gcctgccctc caggcttcgt gggactgcgc tgtgagggag atgtggatga    3360
gtgtctggac cggccctgtc acccctcggg cactgcagct tgccactctt tagccaacgc    3420
cttctactgc cagtgtctgc ctgggcacac aggccagcgt tgtgaggtgg agatggacct    3480
ctgtcagagc caaccctgct ccaatggagg atcctgtgag atcacaacag ggccacccccc   3540 tggcttcacc tgtcactgcc caagggtttt tgaaggcccc acctgcagcc acaaagccct    3600
ttcctgcggc atccatcact gccacaatgg aggcctatgt ctgccctccc ctaagccagg    3660
gtcaccaccg ctctgtgcct gcctcagtgg tttttggggc cctgactgtc tgacacctcc    3720
agctccaccg ggctgcggtc ccccctcacc ctgcctgcac aatggtacct gcactgagac    3780
ccctgggttg ggcaacccgg gctttcaatg cacctgccct cctgactctc cagggccccg    3840
gtgtcaaagg ccaggggcaa gtgggtgtga gggccgaggt ggtgatggga cctgcgatgc    3900
tggctgcagt ggcccaggag gagactggga tggagggac tgttccctgg gggtcccaga     3960
cccctggaag ggctgtcccc cgcattccca gtgctggctt ctgttccggg acggacggtg    4020
tcacccgcag tgtgactctg aggagtgtct ctttgatggc tacgactgtg aaatccctcc    4080
aacctgcatc ccagcctatg accagtactg ccgagatcac ttccacaacg ggcactgtga    4140
gaaaggctgc aataacgctg aatgtggctg gacgggggga gactgcagac cagaagggga    4200
agactcagag gggaggccct ccctggccct gctggtggtg ctgaggcccc cagccctgga    4260
tcagcagctg cttgccctgg cacgagtgct gtccctgact ctgagggtcg gtctctgggt    4320
gaggaaggac agtgaaggca ggaacatggt gttccctat cctgggaccc gggccaaaga     4380
ggagctgagt ggagctaggg attcctcttc atgggaaaga caagcccctc ccactcagcc    4440
cctgggcaag gagacagagt ctcttggtgc agggtttgtg gtagtgatgg gagtggatct    4500
gtcccgctgt ggtccggaac atcctgcgtc ccgctgcccc tgggactctg gactcctgct    4560
gcgcttcctt gcagcaatgg cagcagtggg agctctggag ccctgctgc ctggacccctt    4620 gctggcggct caccctcaag cagggaccag gccccctgcc aaccagcttc cctgcccat     4680 tctatgttca ccagtggttg gggtgcttct cctggcccctt ggggcccttc tcgtcctcca    4740
gctcattcgg cgacggcgac gagaacatgg ggccctgtgg ctgcccctg gtttcattcg     4800 aaggcctcag acacagcagg cacccaccg gcggaggccc ccactgggcg aggacaacat     4860
tggtcttaag gcactgaagc cagaggccga agtggatgag gatggagtgg ccatgtgctc    4920
gggccctgaa gagggagagg ctgaagaaac agcctcagcc tccaggtgcc agctttggcc    4980
gctcaacagc ggctgtggag agctccccca ggcagccatg ctgacccctc ctcaggagtg    5040
tgaatcggag gttctggatg tggacacctg tggacctgat ggggtgacac ccctgatgtc    5100
agccgtcttc tgtggggag tgcagtccac gactggggct agtccacaga gactggggct    5160
aggaaatctg gaaccctggg aaccactgct ggatagaggg gcctgccccc aggctcacac    5220
tgtgggcact ggagagacgc ctctgcacct agctgccaga ttctctcggc caaccgctgc    5280
ccgccgcctc cttgaggctg gagccaaccc caaccagcca gaccgcgctg ggcgcacccc    5340
acttcacact gctgtggctg ccgacgctcg ggaggtttgc cagctcctat tggccagcag    5400
acagactacg tgacgcccc gcacagagga cgggactaca cctttgatgc tggctgccag    5460
gctggccgtg gaggacctgg ttgaagaatt gatcgcagcc cgagcagatg taggagccag    5520
ggataaaagg ggaaaactg cactgcactg ggccgctgct gtgaacaacg cccgagccgc     5580
ccgctctctc ctccaggctg gagcggataa agatgcccag gacagtaggg aacagacgcc    5640
```

-continued

```
gcttttcctg gcagcgcgcg aaggagccgt ggaggtggcg cagctgttgc tggagctcgg      5700
ggcggcccgg ggactgcgag accaggccgg gctggcccca ggagatgtgg cccgccagcg      5760
cagtcactgg gacctgctaa cgctgctgga aggggctgga ccgactacgc aggaggcccg      5820
tgcgcacgca cgcaccacgc cggggggcgg gtccgccccg cgctgccgga cgctgtctgc      5880
gggagcgcgc ccgcgcgggg gcggagcctg tctgcaggct cgcacttggt cggtggactt      5940
gggagagcgc ggagggaagg tgtatgctcg ctgccggagc cgatctggaa gctgcggagg      6000
ccccaccacg cgcggccgca ggttctccgc gggctcccgt ggacgacgcg gggctagggc      6060
atcacaggat gactggcctc gcgactgggt ggccctggaa gcctgcggct ccgcctgcag      6120
tgcgccgatc ccgcctccca gcctgacccc gtccccagaa cgtggatccc ctcaagttgc      6180
ctggggtctt ccagttcacc aagagattcc cttaaactcg gttgtaagaa atctgaacta      6240
ggcagctgcg tggaaggaag gaagcgcacg gtacgagtct ggaagactcc ggacttttaa      6300
ggccaaaata accgttaagc tcacttgtct cccccataga gtatgcacag caatgggaag      6360
agggtttagg atgtccggtt gagatagacc gtgattttcc tggaaaatag gcagcttca      6420 agaggacaaa gttgatttcg agaatcccta aactctggaa ccaagaactg tgggcgaatt      6480
gggtgtaaaa tgtttcttgt gtatggtttc ccaaaaggag cctctgctat ctactgccca      6540
caagtagctg gcaactattt attaagcacc tacgatgtgc cgggtgttgt gtagatgaac      6600
agtaagtaac cagtggccca tccagctgat gactccttgc cctctctctg cctccccaca      6660
aggacactgg tgcaggg                                                    6677
```

<210> SEQ ID NO 7
<211> LENGTH: 22
<212> TYPE: DNA
<213> ORGANISM: mouse

<400> SEQUENCE: 7
cgtcctgctg cgcttccttg ca                                                22

<210> SEQ ID NO 8
<211> LENGTH: 24
<212> TYPE: DNA
<213> ORGANISM: mouse

<400> SEQUENCE: 8
ccggtgccta gttcagattt ctta                                              24

<210> SEQ ID NO 9
<211> LENGTH: 18
<212> TYPE: PRT
<213> ORGANISM: mouse

<400> SEQUENCE: 9

Ser Met Ala Tyr Pro Tyr Asp Val Pro Asp Tyr Ala Ser Leu Gly Pro
 1               5                  10                  15

Gly Pro

<210> SEQ ID NO 10
<211> LENGTH: 39
<212> TYPE: DNA
<213> ORGANISM: mouse

<400> SEQUENCE: 10
cggttgtaag aaatctgaac tccatggcct acccatatg                              39